(12) United States Patent
Fink et al.

(10) Patent No.: US 7,125,903 B1
(45) Date of Patent: Oct. 24, 2006

(54) THIENOISOXAZOLYL-AND THIENYLPYRRAZOLYL-PHENOXY SUBSTITUTED PROPYL DERIVATIVES USEFUL AS $D_4$ ANTAGONISTS

(75) Inventors: David M. Fink, Lebanon, NJ (US); Brian S. Freed, Phillipsburg, NJ (US); Nicholas J. Hrib, Hillsborough, NJ (US); Raymond W. Kosley, Jr., Bridgewater, NJ (US); George E. Lee, Somerville, NJ (US); Gregory H. Merriman, Phillipsburg, NJ (US); Barbara S. Rauckman, Flemington, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 10/088,250

(22) PCT Filed: Sep. 13, 2000

(86) PCT No.: PCT/US00/24962

§ 371 (c)(1),
(2), (4) Date: Dec. 23, 2002

(87) PCT Pub. No.: WO01/19833

PCT Pub. Date: Mar. 22, 2001

Related U.S. Application Data

(60) Provisional application No. 60/229,355, filed on Sep. 14, 1999.

(51) Int. Cl.
 A61K 31/42 (2006.01)
 A61K 31/415 (2006.01)
 C07D 261/00 (2006.01)
 C07D 231/00 (2006.01)

(52) U.S. Cl. .................. 514/379; 548/241; 548/360.1; 549/59; 514/406; 514/444

(58) Field of Classification Search ................ 548/241, 548/360.1; 549/59; 514/379, 406, 444
See application file for complete search history.

(56) References Cited

U.S. PATENT DOCUMENTS

| | | | |
|---|---|---|---|
| 4,075,227 A | 2/1978 | Jones et al. | |
| 4,085,114 A | 4/1978 | Adachi et al. | |
| 4,355,037 A | 10/1982 | Strupczewski et al. | |
| 4,408,053 A | 10/1983 | Strupczewski et al. | |
| 4,408,054 A | 10/1983 | Strupczewski et al. | |
| 4,427,691 A | 1/1984 | Shutske et al. | |
| 4,452,804 A | 6/1984 | Shutske et al. | |
| 4,469,869 A | 9/1984 | Strupczewski et al. | |
| 4,504,669 A | 3/1985 | Shutske et al. | |
| 4,528,376 A | 7/1985 | Strupczewski et al. | |
| 4,644,064 A | 2/1987 | Shutske et al. | |
| 4,728,651 A * | 3/1988 | Ong et al. | 514/254.04 |
| 4,769,472 A * | 9/1988 | Ong et al. | 548/242 |
| 5,114,936 A | 5/1992 | Wettlaufer et al. | |
| 5,143,923 A | 9/1992 | Hrib et al. | |
| 5,177,088 A | 1/1993 | Effland et al. | |
| 5,180,834 A | 1/1993 | Wettlaufer et al. | |
| 5,225,412 A | 7/1993 | Hrib et al. | |
| 5,225,414 A | 7/1993 | Henning et al. | |
| 5,254,595 A | 10/1993 | Guzzi et al. | |
| 5,256,672 A | 10/1993 | Wettlaufer et al. | |
| 5,321,037 A | 6/1994 | Nagano et al. | |
| 5,328,920 A | 7/1994 | Effland et al. | |
| 5,340,833 A | 8/1994 | Bridges et al. | |
| 5,576,319 A | 11/1996 | Baker et al. | |
| 5,593,994 A | 1/1997 | Batt et al. | |
| 5,696,113 A | 12/1997 | Palermo et al. | |
| 5,780,474 A | 7/1998 | Peglion et al. | |
| 5,843,940 A | 12/1998 | Cullinan et al. | |
| 5,852,022 A | 12/1998 | Palermo et al. | |
| 5,856,503 A | 1/1999 | Aebi et al. | |
| 5,932,586 A | 8/1999 | Batt et al. | |
| 5,965,554 A | 10/1999 | Palermo et al. | |
| 6,008,348 A | 12/1999 | Palermo et al. | |
| 6,022,880 A | 2/2000 | Effland et al. | |
| 6,103,724 A | 8/2000 | Laszlovszky et al. | |
| 6,121,293 A | 9/2000 | Cullinan et al. | |

FOREIGN PATENT DOCUMENTS

| | | |
|---|---|---|
| EP | 0058977 | 9/1982 |
| EP | 0221414 | 5/1987 |
| EP | 0729955 | 9/1996 |
| GB | 1269776 | 4/1972 |
| JP | 10095770 | 4/1998 |
| WO | WO 92/08718 | 5/1992 |
| WO | WO 97/23482 | 7/1997 |
| WO | WO 97/28115 | 8/1997 |
| WO | WO 97/40027 | 10/1997 |
| WO | WO 99/40067 | 8/1999 |
| WO | WO 01/19833 | 3/2001 |

OTHER PUBLICATIONS

Ong et al (1987): STN International CAPLUS database, Columbus (Ohio), Accession No.,1987:598314.*

* cited by examiner

*Primary Examiner*—Golam M. M. Shameem
(74) *Attorney, Agent, or Firm*—Barbara E. Kurys

(57) ABSTRACT

The compounds are of the class thienoisoxazolyl- and thienylpyrrazolyl-phenoxy substituted propyl derivatives, useful as $D_4$ antagonists. Said compounds are useful for the treatment of medical conditions mediated by inhibition of $D_4$ receptor. These conditions comprise, for example, Attention Deficit Hyperactivity Disorder, Obsessive-Compulsive Disorder, Psychoses, Substance Abuse, Substance Dependence, Parkinson's Disease, Parkinsonism, Tardive Diskinesia, Gilles de la Tourette Syndrome, Conduct Disorder, and Oppositional Defiant Disorder. A further aspect of the invention is to provide a pharmaceutical composition, intermediates, and a method of making said class of compounds.

28 Claims, No Drawings

THIENOISOXAZOLYL-AND THIENYLPYRRAZOLYL-PHENOXY SUBSTITUTED PROPYL DERIVATIVES USEFUL AS D₄ ANTAGONISTS

This application is a 371 of PCT/US00/24962, Filed Sep. 13, 2000, and claims the benefit of U.S. Provisional No. 60/229,355, Filed Sep. 14, 1999.

FIELD OF THE INVENTION

The present invention comprises compounds of Formula I useful as therapeutic agents for conditions treated by antagonizing $D_4$ receptor stimulation, e.g., Attention Deficit Hyperactivity Disorder, Obsessive Compulsive Disorder and Psychoses. Intermediates, method of making the compounds and methods of using the compounds are also claimed.

BACKGROUND OF THE INVENTION

The relatively new science of molecular biology has allowed new insights into the mechanisms of CNS diseases via the isolation and cloning of receptor subtypes. Thus, while earlier functional studies had distinguished only two subtypes of dopamine receptor, to date five distinct subtypes have been identified. The dopamine $D_4$ receptor was first cloned in 1991 by Van Tol, Seeman, Civelli, et al. and shown to be localized in the limbic regions of the brain, areas associated with cognitive and emotional behaviors (Van Tol, H. H. M.; Bunzow, J. R.; Guan, H-C.; Sunahara, R. K.; P. Seeman, Niznik, H. B.; Civelli, O.; Cloning of the gene for a human dopamine $D_4$ receptor with high affinity for the antipsychotic clozapine. Nature 1991, 350, 610.)

The $D_4$ receptor was also localized to the frontal cortex implying a role in cognition and executive function. Furthermore, it has been reported that the selective $D_4$ antagonist NGD-94-1 caused improvement in performance retention in a passive avoidance test in rodents and improved performance in a spatial water maze task. (Tallman, J. NGD-94-1; A Specific Dopamine $D_4$ Antagonist. Catecholamines-Bridging Basic Science with Clinical Medicine. Goldstein, D. S.; Eisenhofer, G.; McCarty, R., Eds.; Academic Press: New York, 1997). The effects of this compound in these assays are consistent with the anatomical localization of the $D_4$ receptor in the cortex, hippocampus and thalamus.

Genetic linkage and association studies using polymorphism have been carried out to obtain insights into the possible roles for this receptor in disease. It has been reported that there is a positive association between the repeat polymorphism of seven repeat units and a number of clinical conditions which have a high degree of comorbidity such as Attention Deficit Hyperactivity Disorder and Obsessive Compulsive Disorder-tics (Cruz, C. et al., Increased prevalence of the seven-repeat variant of the dopamine $D_4$ receptor gene in patients with obsessive-compulsive disorder with tics. Neurosci. Lett. 1997, 231, 1. Van Tol, H. H. M. (1995) Clin Neuropharmacol. 18: S143–153).

One of the most remarkable polymorphisms in the human dopamine $D_4$ receptor is a variable number of 48 bp tandem repeats in the third cytoplasmic loop. Individuals with 2–10 tandem repeat units have been identified. Interestingly, this polymorphism appears to be primate-specific and has not been observed in rodents suggesting that these polymorphisms are evolutionarily recent events (Asghari, V. et al., Dopamine $D_4$ receptor repeat: analysis of different native and mutant forms of the human and rat genes (1994) Mol. Pharm. 46: 364–373).

The human $D_4$ receptor with seven repeat units has a number of unique characteristics which distinguish it from the other $D_4$ polymorphisms. This D4.7 variant has displayed a two- to threefold lower potency for the endogenous ligand dopamine than did the D4.2 variant ($EC_{50}$=40 nM vs 15 nM) however, the functional implications of this lower affinity are not yet resolved.

Attention Deficit Hyperactivity Disorder (hereinafter ADHD)

Attention deficit hyperactivity disorder (ADHD) is a disease which affects 3–5% of school age children. It is highly prevalent, making up to 50% of child psychiatry populations. The disease can also persist into adulthood, affecting 1-3% of adults. The diagnosis of ADHD revolve around three basic criteria: inattention, hyperactivity, and impulsivity. Approximately 50–70% of school-age children with the diagnosis of ADHD continue to manifest symptoms through middle adolescence, and almost one third will show some signs of the disorder in adulthood.

It has been shown that dopamine $D_4$ receptor gene polymorphism is associated with ADHD. Patients suffering from ADHD had a significant increase in the prevalence of 7-fold repeat form of the $D_4$ receptor, a variant which is unique for primates (LaHoste, G. J.; Swanson, J. M.; Wigal, S. B.; Glabe, C.; Wigal, T.; King, N.; Kennedy, J. L.; Dopamine $D_4$ receptor gene polymorphism is associated with attention deficit hyperactivity disorder. Mol. Psychiatry 1996, 1, 121). Interestingly, an excess of the D4.7 allele has also been associated with the personality trait of "novelty-seeking"; individuals scoring higher than average on this scale are characterized as impulsive, exploratory, fickle, excitable, quick-tempered and extravagant (Ebstein, R. P. et al.; Dopamine $D_4$ receptor ($D_4DR$) exon III polymorphism associated with the human personality trait of Novelty Seeking. Nature Genetics. 1996, 12, 78 and Benjamin, J. et al.; Population and familial association between the $D_4$ dopamine receptor gene and measures of Novelty Seeking. Nature Genetics. 1996, 12, 81).

This variant of the $D_4$ receptor may have a dysregulated response to dopamine, perhaps suggesting a gain of function for this receptor (Van Tol, H. H. M.; Wu, C. M.; Guan, H-C.; Ohara, K.; Bunzow, J. R.; Civelli, O.; Kennedy, J.; Seeman, P.; Niznik, H. B.; Jovanovic, V.; Multiple dopamine $D_4$ receptor variants in the human population. Nature 1992, 352, 149. b) Van Tol, H. H. M.; Structural and Functional characteristics of the Dopamine $D_4$ Receptor. In Catecholamines Bridging Basic Science with Clinical Medicine. Goldstein, D. S.; Eisenhofer, G.; McCarty, R., Eds.; Academic Press: New York, 1997). Therefore, these data suggest that a $D_4$ antagonist may be efficacious in the treatment of ADHD without the side effect liability seen with current drug therapies.

Patients with ADHD also have markedly increased incidence of Conduct Disorder and Oppositional Defiant Disorder. Conduct Disorder is a disorder wherein the patient exhibits a repetitive and persistent pattern of behavior in which the basic rights of others or major age-appropriate societal norms or rules are violated. These behaviors fall into four main groupings: aggressive conduct that causes or threatens physical harm to other people or animals, nonaggressive conduct that causes property loss or damage, deceitfulness or theft, and serious violations of rules. Oppositional Defiant Disorder is a disorder wherein the patient exhibits some of the patterns of behavior observed in Conduct Disorder (e.g., disobedience and opposition to authority figures), however it does not include the persistent pattern of the more serious forms of behavior in which either the basic rights of others or age-appropriate societal norms or rules are violated. Although children with ADHD often exhibit hyperactive and impulsive behavior that may be disruptive, this behavior does not by itself violate age-appropriate societal norms and therefore does not usually meet criteria for Conduct Disorder. No specific data regarding gene frequency is available for these conditions, which are relatively refractory to available pharmacotherapy. If abnormalities of the $D_4$ neurotransmission involved in the pathogenesis of ADHD, it would be likely that $D_4$ abnormalities would also play a role in these conditions.

Obsessive-Compulsive Disorder (hereinafter OCD)

Obsessive-compulsive disorder is a neurosis characterized by the presence of recurrent ideas and fantasies (obsessions) and repetitive impulses or actions (compulsions) that patients recognize as morbid and toward which they feel a strong inner resistance. In the US it is estimated that approximately four million patients are afflicted with OCD; however, fewer than half are diagnosed and treated.

The same seven-repeat variant of the dopamine $D_4$ receptor gene has been found to show increased prevalence in patients suffering from obsessive-compulsive disorder with tics (Cruz, C. et al., Increased prevalence of the seven-repeat variant of the dopamine $D_4$ receptor gene in patients with obsessive-compulsive disorder with tics. Neurosci. Lett. 1997, 231, 1. Van Tol, H. H. M. (1995) Clin Neuropharmacol. 18: S143–153). It has also been reported that adolescents with OCD plus tics are more prone to show violent and aggressive obsessions than those without tics (Cruz, C. et al., Increased prevalence of the seven-repeat variant of the dopamine $D_4$ receptor gene in patients with obsessive-compulsive disorder with tics. Neurosci. Lett. 1997, 231, 1. Van Tol, H. H. M. (1995) Clin Neuropharmacol. 18: S143–153). As mentioned before, this $D_4$ variant has been shown to have a dysregulated response to dopamine. Thus OCD may also be a disorder associated with a gain of function at the $D_4$ receptor, which would respond to treatment with selective $D_4$ antagonists.

Schizophrenia

Schizophrenia is a severe mental illness affecting an estimated 1% of the world's population. The disease has an uncertain pathophysiology possibly leading to disruption of dopaminergic neural systems through poorly understood interactions of atomic, metabolic and genetic abnormalities. The schizophrenic patient suffers from psychotic symptoms broadly categorized as positive, negative or cognitive. The positive symptoms include delusions, hallucinations, irrational fears, and disorganization of thought. Negative or deficit symptoms include social withdrawal, impairment in role functioning, diminished or inappropriate affect, poverty of speech, marked lack of initiative or energy and the inability to experience pleasure. Cognitive symptoms comprise impairment of attention, verbal fluency, recall memory or executive function. Since the discovery of the clinical antipsychotic activity of chlorpromazine in the 1950s, the pharmacological antagonism of central dopamine receptors remains the only proven means for treating schizophrenia. This is evidenced by the number of agents with varied chemical structures that have been found to share the property of dopamine $D_2$ receptor antagonism and to have clinical benefit.

Recently using molecular biological techniques two families of dopamine receptors have been discovered namely the dopamine $D_1$ family ($D_1$ and $D_5$ receptor subtype) and the dopamine $D_2$ family ($D_2$, $D_3$, and $D_4$ receptor subtype). All clinically effective antipsychotic agents have been shown to bind to these receptor subtypes with varying affinities (Corbett, R. et al., 1997; Iloperidone: Preclinical Profile and early clinical evaluation. CNS Drugs Reviews 3(2): 120–147). A number of the recently introduced antipsychotic drugs with a profile for reduced extrapyramidal side effect liability have been shown to have greater affinity for the dopamine $D_4$ receptor subtype when compared to the dopamine $D_2$ receptor subtype. This greater affinity for the $D_4$ receptor compared to the $D_2$ receptor may contribute to these drugs having greater efficacy and less side effect liability than the traditional typical antipsychotic drugs (Seeman, P., Corbett, R. and Van Tol H. H. M. (1997) Atypical neuroleptics have low affinity for dopamine $D_2$ receptors or are selective for $D_4$ receptors. Neuropsychopharmacology 16 (2): 93–135.). Therefore, compounds with selective $D_4$ affinity may have efficacy against schizophrenia without causing the side effects associated with $D_2$ receptor blockade.

Substance Abuse/Substance Dependence

Repeated administration of psychostimulants such as d-amphetamine to rodents produces a progressive and long-lasting increase in behaviors such as locomotor activity, a phenomenon known as "behavioral sensitization" or "reverse tolerance". This enduring hypersensitivity to psychostimulants is also observed in humans and is thought to underlie drug addiction (Robinson, T. E. and Berridge, K. C. 1993 The neural basis of drug craving: an incentive sensitization theory of addiction Brain Research Reviews 18: 247–291). The mesolimbic dopamine system plays a critical role in the development of drug addiction. The development of behavioral sensitization to amphetamine is thought to reflect neuroadaptive biochemical and genomic responses triggered by the first exposure to the psychostimulant. Postsynaptic neuroplasticity results in alterations in dopamine receptor number and sensitivity. The function of the dopamine $D_2$ receptor family ($D_2$, $D_3$, and $D_4$ receptor subtypes) are all altered by the administration of amphetamine. The chronic administration of a selective dopamine $D_4$ receptor antagonist to rodents has been demonstrated to stop the development of behavioral sensitization to the administration of d-amphetamine indicating that selective dopamine $D_4$ antagonists may have efficacy for the treatment of drug abuse (Feldpausch D. L et al., 1998 The role of Dopamine $D_4$ receptor in the induction of behavioral sensitization to amphetamine and accompanying biochemical and molecular adaptations. Journal of Pharmacology and Experimental Therapeutics 266: 497–508).

A role for the $D_4$ receptor in substance abuse and substance dependence is supported by reports of an excess of long alleles (chiefly 7-repeat) of the $D_4$ exon 3 polymorphism in opiate and possibly alcohol abusers (Ebstein R P, Belmaker R H. 1997 Saga of an adventure gene: novelty seeking, substance abuse and the dopamine $D_4$ receptor ($D_4DR$) exon III repeat polymorphism. Mol Psychiatr 2:381–4; Kotler M, Cohen H, Segman R, et al. 1997 Excess dopamine $D_4$ receptor ($D_4DR$) exon III seven repeat allele in opioid-dependent subjects. Mol Psychiatr 2:251–4; Mel H, Horowitz R, Ohel N, et al. 1998 Additional evidence for an association between the dopamine D$_4$ receptor (D$_4$DR) exon III seven-repeat allele and substance abuse in opioid dependent subjects: Relationship of treatment retention to genotype and personality. Addiction Biology 3:473–81). Long alleles of the D$_4$ exon 3 polymorphism may also be associated with increased difficulty in quitting smoking, which may be related to nicotine addiction (Shields P G, Lerman C, Audrain J, et al. 1998 Dopamine D$_4$ receptors and the risk of cigarette smoking in African-Americans and Caucasians. Cancer Epidemiology, Biomarkers & Prevention 7:453–8).

Parkinson's Disease/Parkinsonism

Parkinson's disease is a progressive disorder of movement, characterized by tremor, rigidity, and bradykinesia. Other manifestations include depression, dementia (especially in advanced disease), and psychosis (especially as a complication of dopaminergic therapy). Parkinson's disease affects approximately 0.1% of the population, usually beginning after age 50. The major pathology is loss of dopaminergic neurons of the zona compacta in the substantia nigra. The major treatment is administration of dopamine precursors or agonists, but these are incompletely effective and are associated with side effects including dyskinesias, psychosis, and hypotension. Anticholinergic drugs are occasionally used, but are of limited efficacy and poorly tolerated.

Traditional antipsychotic drugs (neuroleptics) block the dopamine D$_2$ receptor and commonly produce symptoms of Parkinson's disease "Parkinsonism" in a dose-dependent manner corresponding to the potency of their D$_2$-blockade.

Dopamine synthesis in mouse dorsal striatum is increased in D$_4$ knockout mice (Rubinstein M, Phillips T J, Bunzow J R, et al. 1997 Mice lacking dopamine D$_4$ receptors are supersensitive to ethanol, cocaine, and methamphetamine. Cell 90:991–1001.). This suggests that a D$_4$ antagonist might have efficacy in treating Parkinson's disease, both in the treatment of the primary symptoms and in the treatment of both psychiatric and movement side-effects of standard dopaminergic therapies.

Several studies have suggested benefit of the atypical antipsychotic clozapine not only for treatment levodopa induced psychosis, but also for treatment of Parkinsonian symptoms themselves, especially tremor. These findings were reviewed by Factor and Friedman (Factor S A, Friedman J H. 1997 The emerging role of clozapine in the treatment of movement disorders. Movement Disorders 12:483–96). Clozapine, in addition to prominent D$_4$ blockade, has activity at multiple other receptors, notably serotonin 5-HT$_2$ and acetylcholine muscarinic. It is unlikely that anticholinergic effects account for clozapine's efficacy, as anticholinergic non-responders have responded dramatically to clozapine. While this may be due in part to 5-HT$_2$ antagonism; replacement of clozapine by olanzapine, a potent antagonist of 5-HT$_2$ (albeit with greater dopamine D$_2$ affinity than clozapine), was associated with increased Parkinsonian symptoms in a study of patients with Parkinson's disease (Friedman J H, Goldstein S, Jacques C. 1998 Substituting clozapine for olanzapine in psychiatrically stable parkinson's disease patients: Results of an open label pilot study. Clin Neuropharmacol 21:285–8). Dyskinesias and dystonia, associated with the use of levodopa, have also been reported to improve with clozapine (Factor S A, Friedman J H. 1997 The emerging role of clozapine in the treatment of movement disorders. Movement Disorders 12:483–96).

Further support for the potential role of the D$_4$ receptor in Parkinson's disease comes from a report of increased incidence of long ($\geq 6$ repeats) alleles of the D$_4$ exon 3 polymorphism in Parkinson's disease (Ricketts M H, Hamer R M, Manowitz P, et al. 1998 Association of long variants of the dopamine D$_4$ receptor exon 3 repeat polymorphism with Parkinsons-disease. Clinical Genetics 54:33–8).

Tardive Dyskinesia (hereinafter TD)

Tardive dyskinesia is a movement disorder, consisting of involuntary choreiform, athetoid, or rhythmic movements of the tongue, jaw or extremities which develops as a result of (usually chronic) administration of neuroleptics and typically persists even after these drugs are discontinued. The overall prevalence of Neuroleptic-Induced Tardive Dyskinesia in patients who have received long-term neuroleptic treatment is estimated at 20–30% (American Psychiatric Association: Diagnostic and Statistical Manual of Mental Disorders, Fourth edition. Washington, D.C., American Psychiatric Association, 1994).

Increased concentrations of D$_4$ receptor have been reported in some postmortem studies of schizophrenics (usually treated for extended periods with traditional neuroleptics) (Lahti R A, Roberts R C, Cochrane E V, et al. 1998 Direct determination of dopamine D$_4$ receptors in normal and schizophrenic postmortem brain tissue: A ($^3$H)NGD-94-1 study. Mol Psychiatr 3:528–33; Seeman P, Guan H C, Van Tol H H. 1995 Schizophrenia: elevation of dopamine D$_4$-like sites, using [$^3$H]nemonapride and [$^{125}$I]epidepride. Eur J Pharmacol 286:R3–5). An up-regulation of the D$_2$ receptor has been seen with chronic administration of the neuroleptic haloperidol in both animal and human studies (Schroder J, Silvestri S, Bubeck B, et al. 1998 D$_2$ dopamine receptor up-regulation, treatment response, neurological soft signs, and extrapyramidal side effects in schizophrenia: a follow-up study with $^{123}$I-iodobenzamide single photon emission computed tomography in the drug-naive state and after neuroleptic treatment. Biol Psychiatry 43:660–5). Use of these drugs might also be responsible for up-regulation of the D$_4$ receptor.

Improvement in TD has been seen with clozapine (Bassift D P, Louza-Neto M R. 1998 Clozapine efficacy in tardive dyskinesia in schizophrenic patients. European Archives of Psychiatry & Clinical Neuroscience 248:209–11) a drug with prominent D$_4$ antagonism. While clozapine has other pharmacologic actions, notably 5HT$_2$ receptor blockade, an effect on T.D. has not to date been established for 5HT$_2$/D$_2$ receptor antagonists such as risperidone or olanzapine. The concern might be raised that chronic D$_4$ blockade might also cause tardive dyskinesia, however this complication has been exceedingly rare in patients treated with clozapine.

Gilles de la Tourette Syndrome (hereinafter TS)

Gilles de la Tourette syndrome, a condition manifest by motor and vocal tics, with a prevalence of approximately 0.5% (most common in adolescents), is seen with increased frequency in patients with ADHD and/or OCD, and in family members of patients with those conditions. Use of stimulant drugs (which increase synaptic dopamine concentrations) in patients with ADHD has been associated with an increased incidence of tics and possibly TS (Erenberg G, Cruse R P, Rothner A D. 1985 Gille de la Tourette's syndrome: Effects of stimulant drugs. Neurology 35:1346–8). An increased incidence of the D4.7 allele has been reported in TS (Grice D E, Leckman J F, Pauls D L, et al. 1996 Linkage disequilibrium between an allele at the dopamine D$_4$ receptor locus and Tourette syndrome, by the transmission-disequilibrium test. American Journal of Human Genetics 59:644–52), and haloperidol (a $D_2/D_4$ dopamine antagonist) is effective at controlling tics.

SUMMARY OF THE INVENTION

According to one aspect of the present invention, there is provided a compound of formula I:

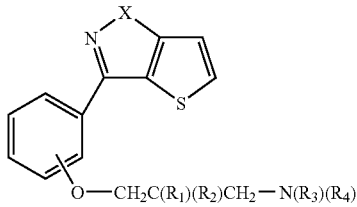

Formula I a pharmaceutically acceptable salt or stereoisomer thereof, wherein

X is $N(CH_3)$ or O;

$R_1$ is OH or $C_{1-6}$ alkoxy;

$R_2$ is H or $C_{1-6}$ alkyl;

$R_3$ is $(CH_2)_n$ Q, $CH_2CH(OH)Q$, $CH(CH_3)Q$, 1,2,3,4-tetrahydronaphthyl, indanyl, or adamantyl, wherein Q is thienyl, phenyl, furanyl, naphthyl, pyridyl, indolyl, indazolyl, cyclohexyl, 1,2-methylenedioxyphenyl, cyclohexenyl, 1H-pyrazolo[4,3-c]pyridyl; and Q is optionally substituted with one or two moieties independently selected from halo, $C_{1-6}$ alkyl, $C_{1-6}$ alkoxy, hydroxy, $S(O)_2NH_2$, trifluoromethyl, or cyano, and n is 1 or 2;

$R_4$ is H or $C_{1-6}$ alkyl; or $R_3$ and $R_4$, together with the nitrogen atom to which $R_3$ and $R_4$ are attached, form 1,4-dioxa-8-azo-spiro[4.5] decanyl, piperazinyl, morpholinyl, piperidinyl, pyrrolidinyl, azocanyl, 1,2,3,4-tetrahydroisoquinolinyl, 1,2,3,4-tetrahydro-β-carbolinyl, 4,5,6,7-tetrahydrothienyl[3,2-c]pyridyl, or 8-aza-bicyclo[3.2.1.]octane, each of which may be mono- or independently di-substituted with halo, $C_{1-6}$ alkyl, $C_{1-6}$ alkoxy, C(O)phenyl, OH, CN, O-phenyl or $(CH_2)_mZ$, Z is benzisoxazolyl, indazolyl, benzisothiazolyl, benzothienyl, pyrimidinyl, pyridyl, 1,2-methylenedioxyphenyl, or phenyl, and Z, CH(OH)phenyl or O-phenyl are optionally substituted with one or two moieties independently selected from halo, $C_{1-6}$ alkyl, $C_{1-6}$ alkoxy, hydroxy, trifluoromethyl, $S(O)_2NH_2$, or cyano, and m is 0 or 1;

provided that when $R_1$ is OH, $R_2$ is H:

(1) $R_4$ is H, and $R_3$ is $(CH_2)_nQ$, where n is 1 or 2, then Q cannot be indolyl or phenyl; or (2) $R_3$ and $R_4$ form piperazinyl substituted with $(CH_2)_mZ$, when m is 1, then Z cannot be phenyl.

Another aspect of the invention is to provide a pharmaceutical composition comprising a compound of formula I in an amount effective to antagonize $D_4$ receptor stimulation and a pharmaceutically acceptable carrier.

In yet another of its aspects, the invention provides the use of compounds of Formula I as $D_4$ receptor antagonists for the treatment of medical conditions mediated by inhibition of $D_4$ receptor. These conditions comprise, for example, Attention Deficit Hyperactivity Disorder, Obsessive-Compulsive Disorder, Psychoses, Substance Abuse, Substance Dependence, Parkinson's Disease, Parkinsonism, Tardive Diskinesia, Gilles de la Tourette Syndrome, Conduct Disorder, and Oppositional Defiant Disorder.

A further aspect of the invention is to provide intermediates and a method of making compounds of the formula II:

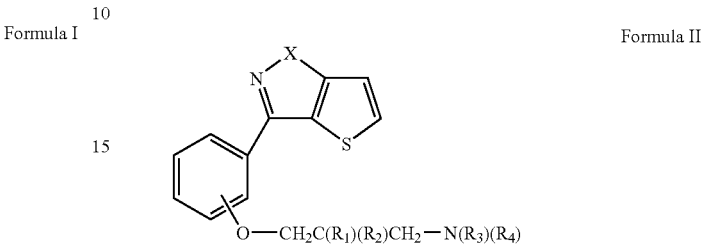

Formula II a pharmaceutically acceptable salt or stereoisomer thereof, wherein

X is $N(CH_3)$ or O;

$R_1$ is OH or $C_{1-6}$ alkoxy;

$R_2$ is H or $C_{1-6}$ alkyl;

$R_3$ is $(CH_2)_n$ Q, $CH_2CH(OH)Q$, $CH(CH_3)Q$, 1,2,3,4-tetrahydronaphthyl, indanyl, or adamantyl, wherein Q is thienyl, phenyl, furanyl, naphthyl, pyridyl, indolyl, indazolyl, cyclohexyl, 1,2-methylenedioxyphenyl, cyclohexenyl, 1H-pyrazolo[4,3-c]pyridyl; and Q is optionally substituted with one or two moieties independently selected from halo, $C_{1-6}$ alkyl, $C_{1-6}$ alkoxy, hydroxy, $S(O)_2NH_2$, trifluoromethyl, or cyano, and n is 1 or 2;

$R_4$ is H or $C_{1-6}$ alkyl; or $R_3$ and $R_4$, together with the nitrogen atom to which $R_3$ and $R_4$ are attached, form 1,4-dioxa-8-azo-spiro[4.5] decanyl, piperazinyl, morpholinyl, piperidinyl, pyrrolidinyl, azocanyl, 1,2,3,4-tetrahydroisoquinolinyl, 1,2,3,4-tetrahydro-β-carbolinyl, 4,5,6,7-tetrahydrothienyl[3,2-c]pyridyl, or 8-aza-bicyclo[3.2.1.]octane, each of which may be mono- or independently di-substituted with halo, $C_{1-6}$ alkyl, $C_{1-6}$ alkoxy, C(O)phenyl, OH, CN, O-phenyl or $(CH_2)_mZ$, Z is benzisoxazolyl, indazolyl, benzisothiazolyl, benzothienyl, pyrimidinyl, pyridyl, 1,2-methylenedioxyphenyl, or phenyl, and Z, CH(OH)phenyl or O-phenyl are optionally substituted with one or two moieties independently selected from halo, $C_{1-6}$ alkyl, $C_{1-6}$ alkoxy, hydroxy, trifluoromethyl, $S(O)_2NH_2$, or cyano, and m is 0 or 1.

DETAILED DESCRIPTION OF THE PRESENT INVENTION

Terms used herein have the following meanings:

a) "Pharmaceutically acceptable salts" means either an acid addition salt or a basic addition salt which is compatible with the treatment of patients for the intended use.

"Pharmaceutically acceptable acid addition salt" is any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid, and sulfonic acids such as methanesulfonic acid, naphthalene sulfonic acid, and 2-hydroxyethanesulfonic acid. Either the mono- or di-acid salts can be formed, and such salts can exist in either a hydrated. solvated or substantially anhydrous form. In general, the acid addition salts of these compounds are more soluble in water and various hydrophilic organic solvents. Furthermore, in comparison to their free base forms, the acid addition salts generally demonstrate higher melting points.

"Pharmaceutically acceptable basic addition salts" means non-toxic organic or inorganic basic addition salts of the compounds of Formula (I) or any of its intermediates. Examples are alkali metal or alkaline-earth metal hydroxides such as sodium, potassium, calcium, magnesium or barium hydroxides; ammonia, and aliphatic, alicyclic, or aromatic organic amines such as methylamine, trimethylamine and picoline. The selection criteria for the appropriate salt will be known to one skilled in the art.

b) "Stereoisomers" is a general term for all isomers of the individual molecules that differ only in the orientation of their atoms in space. It includes mirror image isomers (enantiomers), geometric (cis/trans) isomers, and isomers of compounds with more than one chiral center that are not mirror images of one another (diastereoisomers).

c) "Alkyl" as used herein means a branched or straight chain alkyl (monovalent) or alkylene (divalent) hydrocarbon radical, as is appropriate to the formula, specified by the amount of carbons in the alkyl, e.g., $C_{1-6}$ alkyl means a one, two, three, four, five or six carbon branched or straight chain alkyl or alkylene, as the case may be, or any ranges thereof, for example, but not limited to $C_{1-2}$, $C_{1-3}$, $C_{1-4}$, $C_{1-5}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$, $C_{5-6}$, etc.

d) "Patient" means a warm blooded animal, such as for example rat, mice, dogs, cats, guinea pigs, and primates such as humans.

e) "Treat" or "treating" means to alleviate symptoms, eliminate the causation of the symptoms either on a temporary or permanent basis, or to prevent or slow the appearance of symptoms of the named disorder or condition.

f) "Therapeutically effective amount" means a quantity of the compound which is effective in treating the named disorder or condition.

g) "Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

h) "Psychoses" means conditions wherein the patient experiences a major mental disorder of organic and/or emotional origin characterized by derangement of the personality and loss of contact with reality, often with delusions, hallucinations or illusions. Representative examples of psychotic illnesses include schizophrenia, schizophreniform disorder, schizoaffective disorder, delusional disorder, brief psychotic disorder, shared psychotic disorder, psychotic disorder not otherwise specified, and substance-induced psychotic disorder. See Diagnostic and Statistical Manual of Mental Disorders, 4th ed., American Psychiatric Association, incorporated herein by reference.

i) "Attention-Deficit/Hyperactivity Disorder" or "ADHD" means a condition wherein the patient exhibits a persistent pattern of inattention and/or hyperactivity-impulsivity that is more frequent and severe than is typically observed in individuals at a comparable level of development. It includes ADHD Combined Type, ADHD Predominantly Inattentive Type, and ADHD Predominantly hyperactive-impulsive Type.

j) "Conduct Disorder" means a disorder wherein the patient exhibits a repetitive and persistent pattern of behavior in which the basic rights of others or major age-appropriate societal norms or rules are violated. These behaviors fall into four main groupings: aggressive conduct that causes or threatens physical harm to other people or animals, nonaggressive conduct that causes property loss or damage, deceitfulness or theft, and serious violations of rules.

k) "Oppositional Defiant Disorder" means a disorder wherein the patient exhibits some of the patterns of behavior observed in Conduct Disorder (e.g., disobedience and opposition to authority figures), however it does not include the persistent pattern of the more serious forms of behavior in which either the basic rights of others or age-appropriate societal norms or rules are violated.

l) "Obsessive-Compulsive Disorder" or "OCD" means a condition wherein the patient exhibits recurrent obsessions or compulsions that are severe enough to be time consuming (i.e., take more than an hour a day) or cause marked distress or significant impairment. Obsessions are persistent ideas, thoughts, impulses, or images that are experienced as intrusive and inappropriate and that cause marked anxiety or distress. Compulsions are repetitive behaviors (e.g, hand washing, ordering, checking) or mental acts (e.g., praying, counting, repeating words silently) the goal of which is to prevent or reduce anxiety or distress, not to provide pleasure or gratification.

m) "Substance Dependence" means a condition wherein the patient exhibits a maladaptive pattern of substance use, leading to clinically significant impairment or distress. There is a pattern of repeated self-administration that usually results in tolerance, withdrawal, and compulsive drug-taking.

n) "Substance Abuse" means a condition wherein the patient exhibits a maladaptive pattern of substance use manifested by recurrent and significant adverse consequences related to the repeated use of substances. There may be repeated failure to fulfill major role obligations, repeated use in situations in which it is physically hazardous, multiple legal problems, and recurrent social and interpersonal problems. Unlike the criteria for Substance Dependence, the criteria for Substance Abuse do not include tolerance, withdrawal, or a pattern of compulsive use and instead only include the harmful consequences of repeated use.

o) "Parkinson's Disease" means a slowly progressive neurological condition, characterized by tremor, rigidity, bradykinesia, and postural instability. Other manifestations include depression and dementia.

p) "Parkinsonism" means a condition where the patient exhibits parkinsonian signs or symptoms (i.e. tremor, muscular rigidity, or akinesia) that develop in association with the use of neuroleptic medication.

q) "Neuroleptic-Induced Tardive Dyskinesia" means a disorder characterized by involuntary movements of the tongue, jaw, trunk, or extremities which have developed in association with the use of neuroleptic medication. The involuntary movements may be choreiform, athetoid or rhythmic.

r) "Gilles de la Tourette Syndrome" means a condition manifested by motor and vocal tics. (A tic is a sudden, rapid, recurrent, non-rhythmic, stereotyped motor movement or vocalization.) The disturbance causes marked distress or significant impairment in social, occupational, or other important areas of functioning. The onset is before age eighteen years and the disturbance is not due to the physiological effects of a substance or general medical condition.

s) Unless otherwise specified, "halo" or "halogen" means Cl, Br, F and I.

t) "Aryl sulfonyl" means the radical:

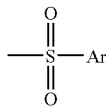

wherein Ar is phenyl optionally substituted one or more moieties from the group consisting of halogen, nitro, or $C_1$–$C_6$alkyl. "Brosyl" means the radical wherein Ar is p-bromobenzene. "Nosyl" means the radical wherein Ar is p-nitrobenzene. "Tosyl" means the radical wherein Ar is p-toluene.

"Alkyl sulfonyl" means the radical:

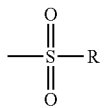

wherein R is $C_1$–$C_6$alkyl. "Mesyl" means the radical wherein R is $CH_3$.

u) "Sulfonic ester" means the radical:

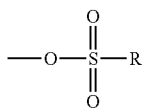

wherein R is $C_1$–$C_6$alkyl or phenyl optionally substituted with one or more moieties from the group consisting of halogen, nitro, or $C_1$–$C_6$alkyl. "Sulfonic esters" are, for example, brosylate, nosylate, tosylate, and mesylate.

v) "Parallel Synthesis" is a term used to describe the simultaneous synthesis of tens to millions of compounds in solution or on a solid phase. The key characteristic that distinguishes this approach from serial techniques is that it does not utilize mixtures.

As used herein, the terms used to describe specific chemical moieties are defined by the corresponding chemical drawings which are set forth on the following page:

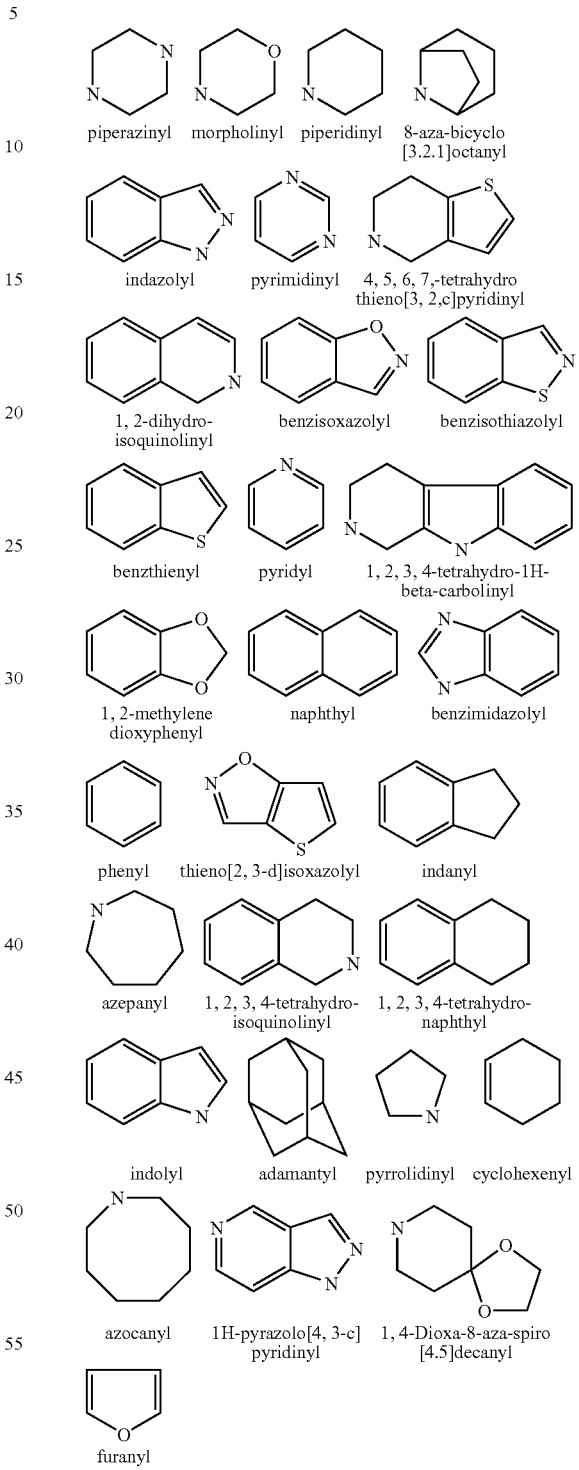

Specific embodiments of the invention are those compounds of Formula I set forth in Table 1.

A preferred embodiment of the invention is the compound according to Formula I wherein $R_3$ is $(CH_2)_nQ$, $CH_2CH(OH)Q$, $CH(CH_3)Q$, indanyl, adamantyl, or 1,2,3,4-tetrahydronaphthyl, wherein Q is thienyl, pyridyl, phenyl, furanyl, naphthyl, cyclohexyl, or benzimidazolyl; or wherein $R_3$ and $R_4$, together with the nitrogen atom to which $R_3$ and $R_4$ are attached, form piperidinyl, piperazinyl, 1,2,3,4-tetrahydroisoquinolinyl, 1,2,3,4-tetrahydro-β-carbolinyl, 4,5,6,7-tetrahydrothieno[3,2-c]pyridinyl, and 8-aza-bicyclo[3.2.1.]octane.

A more preferred embodiment of the invention is a compound according to Formula I wherein $R_1$ is OH; $R_2$ is H; $R_3$ is $(CH_2)_nQ$, wherein n is 1 and Q is thienyl or pyridyl; or $R_3$ and $R_4$, together with the nitrogen atom to which $R_3$ and $R_4$ are attached, form piperidinyl.

Most preferred embodiments of the invention are those compounds of Formula I set forth in Table 1 that exhibit enhanced $D_4$ potency.

Acid addition salts of the compound of Formula I and II are most suitably formed from pharmaceutically acceptable acids, and include for example those formed with inorganic acids, e.g. hydrochloric, sulphuric, or phosphoric acids, and organic acids, e.g. succinic, maleic, acetic or fumaric acid.

Other non-pharmaceutically acceptable salts, e.g. oxalates, may be used for example in the isolation of compounds of Formula I for laboratory use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base, e.g. sodium carbonate or potassium hydroxide, to liberate the free base which is then extracted into an appropriate solvent, such as ether. The free base is then separated from the aqueous portion, dried, and treated with the requisite acid to give the desired salt.

The compounds of the present invention can be prepared by processes analogous to those known in the art. Schemes I, II, and III illustrate methods for the synthesis of compounds of Formula I.

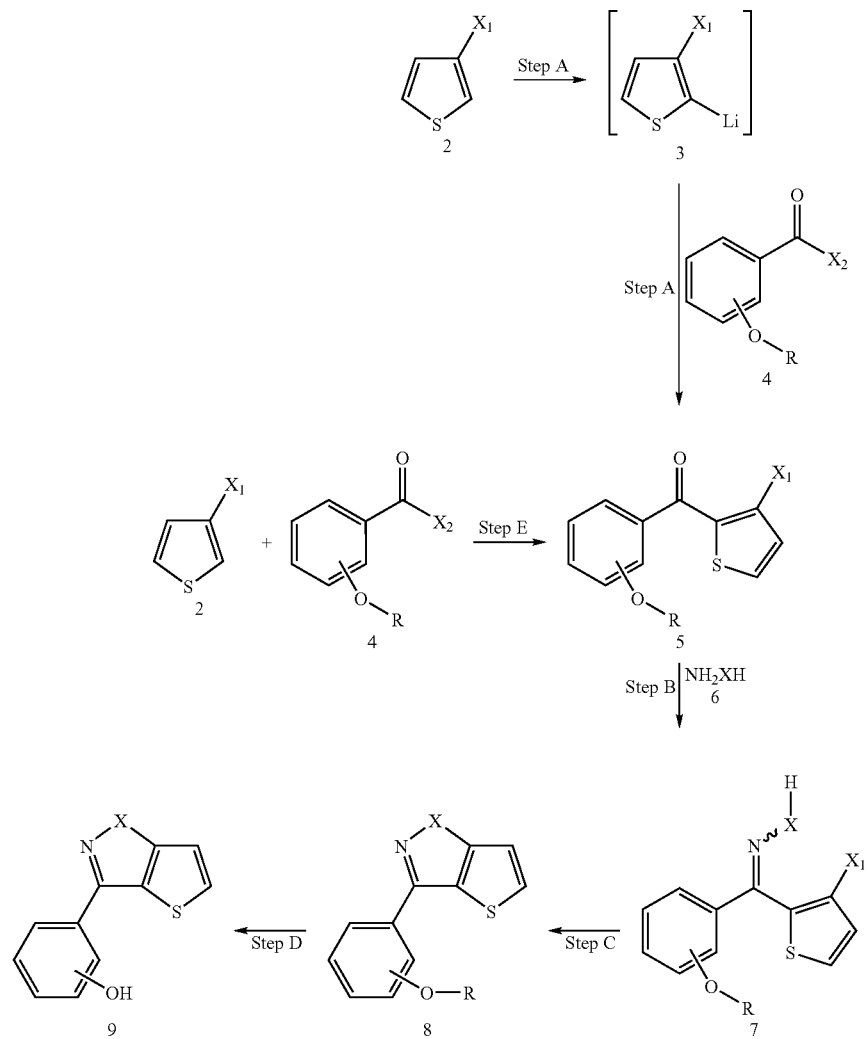

Scheme I $X_1$ = halo, preferably Br; $X_2$ = Br, Cl, or I, preferably Cl;
$X$ = O, N(CH$_3$); R = C$_1$–C$_6$alkyl;

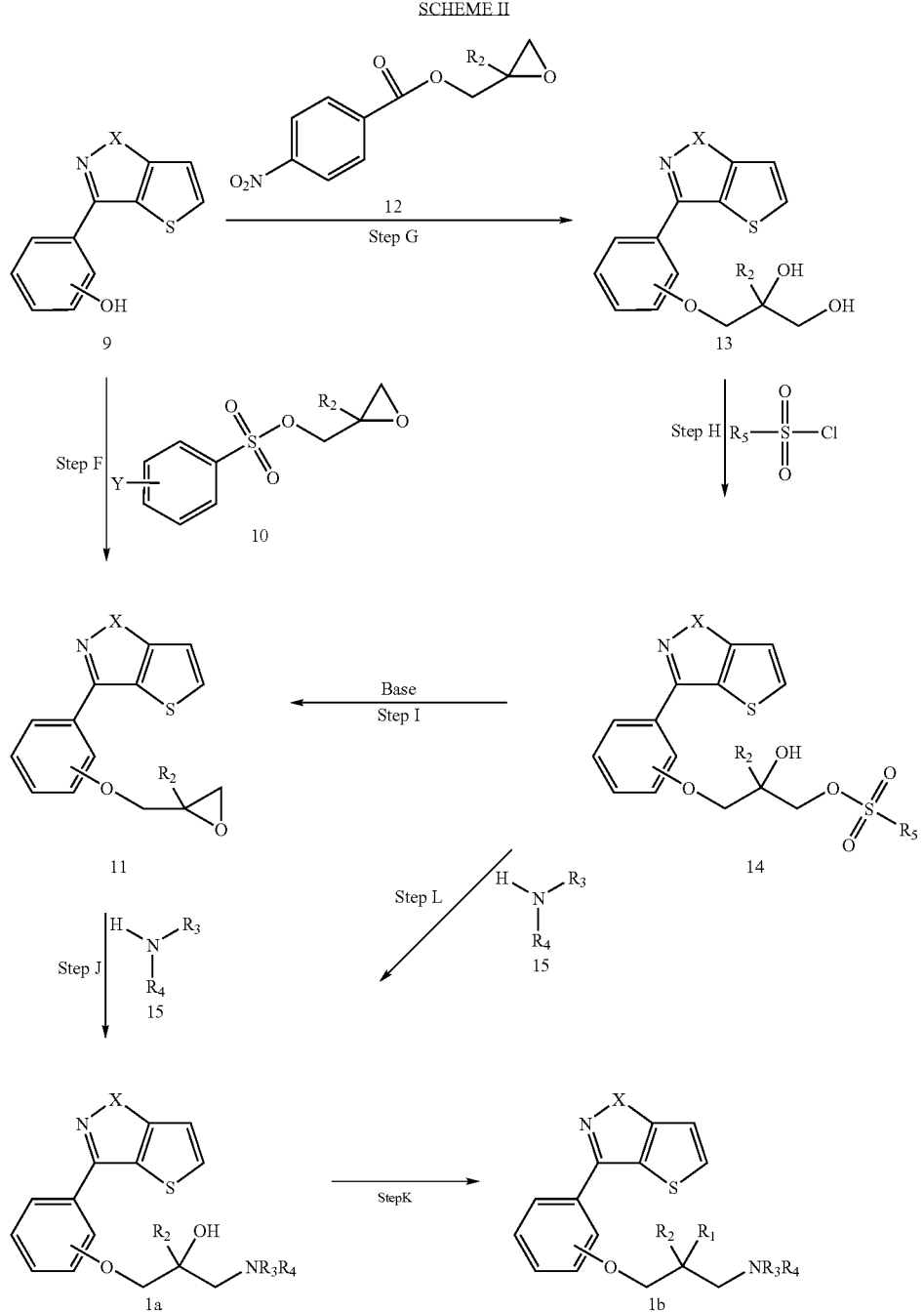

SCHEME II

X = O, N(CH$_3$); Y = 4-CH$_3$, 3-NO$_2$; R$_1$ = C$_{1-6}$alkoxy; R$_2$ = H or C$_{1-6}$alkyl; R$_3$ = (CH$_2$)$_n$Q, CH$_2$CH(OH)Q, CH(CH$_3$)Q, 1, 2, 3, 4-tetrahydronaphthyl, indanyl, or adamantyl; Q is thienyl, phenyl, furanyl, naphthyl, pyridyl, indolyl, indazolyl, cyclohexyl, 1, 2-methylenedioxyphenyl, cyclohexenyl, benzimidizolyl, 1H-pyrazolo[4, 3-c]pyridyl; and Q is optionally substituted with one or two moieties independently selected from halo, C$_{1-6}$alkyl, C$_{1-6}$alkoxy, hydroxy, S(O)$_2$NH$_2$, trifluoromethyl, or cyano and n is 1 or 2; R$_4$ = H or C$_{1-6}$alkyl; or R$_3$ and R$_4$, together with the nitrogen atom to which R$_3$ and R$_4$ are attached, from 1, 4-dioxa-8-azospiro[4.5]decanyl, piperazinyl, morpholinyl, piperidinyl, pyrrolidinyl, azocanyl, 1, 2, 3, 4-tetrahydroisoquinolinyl, 1, 2, 3, 4-tetrahydro- β-carbolinyl, 4, 5, 6, 7-tetrahydrothienyl[3, 2-c]pyridyl, or 8-azabicyclo[3.2.1]octane, each of which may be mono- or independently di-substituted with halo, C$_{1-6}$alkyl, C$_{1-6}$alkoxy, C(O)phenyl, OH, CN, O-phenyl or (CH$_2$)$_m$Z; Z is benzisoxazolyl, indazolyl, benzothiazolyl, benzothienyl, pyrimidinyl, pyridyl, 1, 2-methylenedioxyphenyl, or phenyl; R$_5$ = CH$_3$, CF$_3$, F, p-bromobenzene, p-nitrobenzene, or p-methylbenzene; and Z, CH(OH)phenyl or O-phenyl are optionally substituted with one or two moieties independently selected from halo, C$_{1-6}$alkyl, C$_{1-6}$alkoxy, hydroxy, trifluoromethyl, S(O)$_2$NH$_2$, or cyano, and m is 0 or 1.

Scheme III

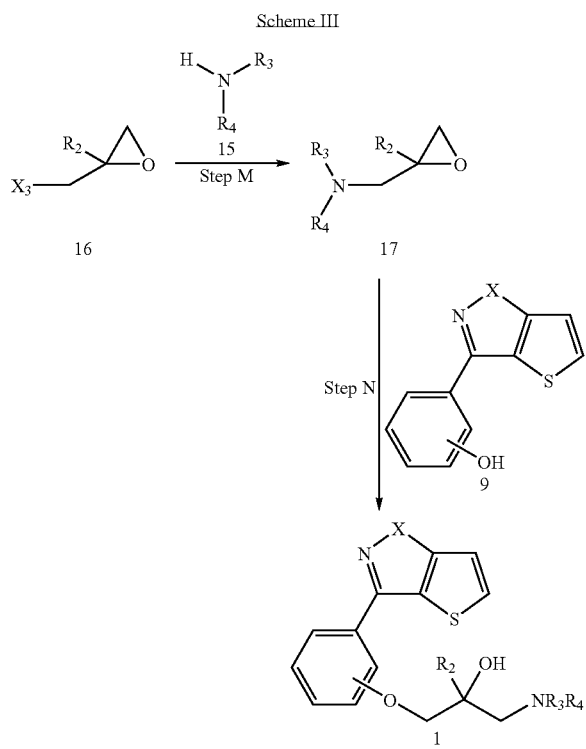

X = O, N(CH$_3$); X$_3$ = halo, p-toluenesulfonyloxy, 3-nitrobenzenesulfonyloxy; R$_2$ = H or C$_{1-6}$alkyl; R$_3$ = (CH$_2$)$_n$Q, CH$_2$CH(OH)Q, CH(CH$_3$)Q,
1, 2, 3, 4-tetrahydronaphthyl, indanyl, or adamantyl; Q is thienyl, phenyl, furanyl, naphthyl, pyridyl, indolyl,
indazolyl, cyclohexyl, 1, 2-methylenedioxyphenyl, cyclohexenyl, benzimidizolyl, 1H-pyrazolo[4, 3-c]pyridyl;
Q is optionally substituted with one or two moieties independently selected from halo, C$_{1-6}$alkyl,
C$_{1-6}$alkoxy, hydroxy, S(O)$_2$NH$_2$, trifluoromethyl, or cyano and n is 1 or 2; R$_4$ = H or C$_{1-6}$alkyl; or R$_3$ and R$_4$,
together with the nitrogen atom to which R$_3$ and R$_4$ are attached, from 1, 4-dioxa-8-azospiro[4.5]decanyl,
piperazinyl, morpholinyl, piperidinyl, pyrrolidinyl, azocanyl, 1, 2, 3, 4-tetrahydroisoquinolinyl,
1, 2, 3, 4-tetrahydro- β-carbolinyl, 4, 5, 6, 7-tetrahydrothienyl[3, 2-c]pyridyl, or 8-azabicyclo[3.2.1]octane, each of
which may be mono- or independently di-substituted with halo, C$_{1-6}$alkyl, C$_{1-6}$alkoxy,
C(O)phenyl, OH, CN,
O-phenyl or (CH$_2$)$_m$Z; Z is benzisoxazolyl, indazolyl, benzisothiazolyl, benzothienyl, pyrimidinyl, pyridyl,
1, 2-methylenedioxyphenyl, or phenyl; and Z, CH(OH)phenyl or O-phenyl are optionally substituted with one or two moieties
independently selected from halo, C$_{1-6}$alkyl, C$_{1-6}$alkoxy, hydroxy, trifluoromethyl, S(O)$_2$NH$_2$, or cyano, and m is 0 or 1.

In Scheme I, step A, diarylketone (5) is prepared by reacting an appropriate alkoxy-substituted benzoyl halide (4) with the anion of a 3-halothiophene (3) using techniques and procedures well known to one or ordinary skill in the art.

For example, a solution of phenyllithium in cyclohexane-ether can be reacted with the halothiophene of structure 2 such as 3-bromothiophene, at 5° C., to form a lithiated intermediate (3). The lithiated intermediate may then be added dropwise over a period of time of about 3 hours to a solution of an alkoxy-substituted benzoyl halide of structure (4) such as 3-methoxybenzoyl chloride and a suitable aprotic anhydrous solvent such as tetrahydrofuran at about −70° C. The resulting ketone of structure (5) may be recovered from the reaction mixture by extractive methods as is well known in the art. Purification of the ketone of structure (5) may be done by alumina column chromatography eluting with a suitable solvent, such as hexane, or a mixture of solvents, such as a mixture of ether and hexane. Further purification may be done by vacuum distillation and/or recrystallization.

In step E, an appropriately substituted diarylketone (5) may be also prepared by treating a solution of a 3-halothiophene (2) such as 3-bromothiophene in a suitable solvent such as dichloromethane with a solution of titanium tetrachloride in a suitable solvent such as dichloromethane at about 5° C. A solution of an appropriately substituted alkoxybenzoyl halide (4) such as 4-methoxybenzoylchloride in a suitable solvent such a dichloromethane is added at such a rate as to maintain the temperature at about or below 5° C. The reaction is quenched with an aqueous acid such as hydrochloric acid and the diarylketone (5) may be recovered by extractive methods and purified by methods well known in the art.

In step B, the oxime derivative (7) (X═O) of diarylketone (5) is prepared by reacting diarylketone (5) and hydroxylamine hydrochloride (6) (X is O).

For example, a diarylketone (5) such as (3-bromothiophen-2-yl)-(3-methoxyphenyl)methanone and hydroxylamine hydrochloride can be reacted in a suitable solvent aprotic solvent, such as pyridine. The reactants are typically stirred together at room temperature for a period of time, typically overnight, followed by heating at a temperature of from about 100° C. to about 105° C. for about 4 hours. The resulting oxime of structure (7) may be recovered from the reaction mixture by extractive methods as is known in the art. The crude oxime of structure (7) may then be purified by recrystallization.

In step C, the oxime of structure (7) (X═O) is cyclized with the appropriate reagents to give the corresponding thieno[2,3-d]isoxazole of structure (8) (X═O).

For example, an oxime of structure (7) such as (3-bromothiophen-2-yl)-(3-methoxyphenyl)methanone oxime can be treated with a suitable base, such as potassium hydroxide in a protic solvent, such as 2-methoxyethanol. The reactants are typically stirred and heated together at a temperature of from about 105° C. to about 110° C., under a nitrogen atmosphere, for a period of time of about one hour. The mixture may then be treated with an appropriate catalyst such as copper chloride and the reaction heated for about four hours. The reaction is quenched with hydrochloric acid, filtered, and the resulting thieno[2,3-d]isoxazole of structure (8) may be recovered from the reaction mixture by extractive methods as is known in the art. The crude thieno[2,3-d]isoxazole of structure (8) may then be purified by chromatography.

In steps B and C, the thieno[3,2-c]pyrazole (8) (X═N—CH$_3$) may be prepared by reacting diarylketone (5) and methylhydrazine (6) (X is N).

For example, a mixture of diarylketone (5) such as (3-bromothiophen-2-yl)-(3-methoxyphenyl)methanone, methylhydrazine and a suitable solvent such as ethylene glycol are heated at a temperature of from about 120° C. to about 130° C. for about 2.5 hours. The reaction is quenched with water and the resulting thieno[3,2-c]pyrazole of structure (8) (X═N—CH$_3$) may be recovered from the reaction mixture by extractive methods and purified by methods well known in the art.

In step D, the thieno[2,3-d]isoxazole compound of structure (8) (X═O) is dealkylated with the appropriate reagents to give the corresponding phenol (9) (X═O).

For example, the thieno[2,3-d]isoxazole of structure (8) such as 3-(4-methoxyphenyl)thieno[2,3-d]isoxazole can be treated with a suitable reagent, such as aluminum chloride or boron tribromide, in a suitable solvent, such as 1,2-dichloroethane or trichloromethane, to cleave the alkoxy moiety.

The reactants are typically stirred and heated together at a temperature of about 70° C. for a period of time of about 1.5 hours. The resulting thieno[2,3-d]isoxazole of structure (9) may be recovered from the reaction mixture by filtration and extractive methods as is known in the art. The crude thieno[2,3-d]isoxazole of structure (9) (X=O) may then be purified by chromatography.

In step D, the thieno[3,2-c]pyrazole of structure (8) (X=N—CH$_3$) is O-dealkylated with the appropriate reagents to give the corresponding phenol (9) (X=N—CH$_3$).

For example, a solution of a thieno[3,2-c]pyrazole of structure (8) such as 3-(3-methoxyphenyl)-1-methyl-1H-thieno[3,2-c]pyrazole and a suitable solvent such as dichloromethane is treated dropwise under nitrogen with a solution of boron tribromide in dichloromethane and stirred at room temperature for about 2.5 hours. The reaction is quenched with water and the resulting thieno[3,2-c]pyrazole of structure (9) (X=N—CH$_3$) may be recovered from the reaction mixture by extractive methods as is known in the art. The crude thieno[3,2-c]pyrazole of structure (9) may then be purified by chromatography.

In Scheme II, step F, thieno[2,3-d]isoxazole-epoxide (11) (X=O) is prepared by condensing the appropriately substituted thieno[2,3-d]isoxazole (9) with an appropriate glycidyl sulfonyl ester (10).

For example, a solution of a thieno[2,3-d]isoxazole (9) such as 3-(4-hydroxyphenyl)thieno[2,3-d]isoxazole in an appropriate aprotic solvent such as dimethylformamide is treated with a suitable base such as sodium hydride, and the resultant anion is treated with a solution of a glycidyl sulfonyl ester (10) such as (2R)-(−)glycidyl tosylate at ambient temperature. The resulting thieno[2,3-d]isoxazole-epoxide (11) may be recovered from the reaction mixture by aqueous quenching and extractive methods as is known in the art. The crude thieno[2,3-d]isoxazole-epoxide (11) may then be purified by chromatography.

In step F, thieno[3,2-c]pyrazole-epoxide (11) (X=N—CH$_3$) is prepared by condensing thieno[3,2-c]pyrazole (9) with an appropriate glycidyl sulfonyl ester (10).

For example, a solution of a thieno[3,2-c]pyrazole (9) such as 3-(1-methyl-1 H-thieno[3,2-c]pyrazol-3-yl)phenol in an appropriate aprotic solvent such as dimethylformamide is treated with a suitable base such as sodium hydride, and the resultant anion is treated with a solution of a glycidyl sulfonyl ester (10) such as (2R)-(−)glycidyl tosylate at ambient temperature. The resulting thieno[3,2-c]pyrazole-epoxide (11) may be recovered from the reaction mixture by aqueous quenching and extractive methods as is known in the art. The crude thieno[3,2-c]pyrazole-epoxide (11) may then be purified by chromatography.

Alternatively, in steps G, H, and I, the thieno[2,3-d] isoxazole-epoxide of structure (11) (X=O) may be prepared by condensing thieno[2,3-d]isoxazole (9) with a glycidyl benzoyl ester (12), conversion of the intermediate thieno[2,3-d]isoxazole-diol (13) to the monosulfonylester (14), and base-induced ring closure of the monosulfonylester (14) to the epoxide (11).

For example, step G, a solution of a thieno[2,3-d]isoxazole (9) such as 3-thieno[2,3-d]isoxazol-3-yl-phenol in a suitable aprotic solvent such as dimethylformamide is treated with a suitable base such as potassium t-butoxide at about room temperature. The resulting anion is treated with a solution of a glycidyl benzoyl ester (12) such as (2S)-(+)-2-methylglycidyl-4-nitrobenzoate at room temperature and then warming at about 50° C. for about two hours. The resulting thieno[2,3-d]isoxazole-diol (13) may be recovered from the reaction mixture by aqueous quenching and extractive methods as is known in the art. The crude thieno[2,3-d]isoxazole-diol (13) may then be purified by chromatography. In step H, a thieno[2,3-d]isoxazole-diol (13) such as (R)-2-methyl-3-(3-thieno[2,3]-d-isoxazol-3-yl-phenoxy) propane-1,2-diol in an appropriate solvent such a dichloromethane is treated with a sulfonyl chloride such as p-toluenesulfonyl chloride and a suitable base such as pyridine at room temperature followed by stirring at room temperature for about 48 hours. The resulting thieno[2,3-d]isoxazole-sulfonyl ester (14) may be recovered from the reaction mixture by dilution with a solvent such as dichloromethane, aqueous quenching and extractive methods as is known in the art. The crude thieno[2,3-d]isoxazole-sulfonyl ester (14) (X=O) may then be purified by chromatography. In step I, a solution of a thieno[2,3-d]isoxazole-sulfonyl ester (14) such as toluene-4-sulfonic acid (S)-2-hydroxy-2-methyl-3-(3-thieno[2,3-d]isoxazol-3-yl-phenoxy)-propyl ester in a suitable aprotic solvent such as tetrahydrofuran is treated with a base such as potassium t-butoxide at a temperature of about 0° C. After stirring for about 1 hour at about 0° C. the reaction is quenched using extractive methods as is known in the art. The crude thieno[2,3-d]isoxazole-epoxide of structure (11) (X=O) may then be purified by recrystallization or chromatography as is well known in the art.

In step J, a 1-amino-3-(3-thieno[2,3-d]isoxazol-3-yl)-propan-2-ol compound of structure 1a (X=O) is prepared by treating a thieno[2,3-d]isoxazole-epoxide of structure (11) with an appropriate primary or secondary amine (5).

For example a thieno[2,3-d]isoxazole-epoxide (11) such as (R)-3-(3-epoxymethoxyphenyl)thieno[2,3-d]isoxazole in a suitable solvent such as ethanol is treated with an appropriate amine (15) such as N-benzyl-N-methylamine under an inert atmosphere such a nitrogen or argon. After stirring the mixture at about 60° C. for about 0.5 hour and at about 80° C. for about 0.5 hour, the reaction mixture may be concentrated and the crude 1-amino-3-[3-(thieno[2,3-d]isoxazol-3-yl)phenoxy]propan-2-ol (1a) may then be purified by chromatography. The resulting 1-amino-3-[3-(thieno[2,3-d] isoxazol-3-yl)phenoxy]propan-2-ol of structure (1a) may also be recovered from the reaction mixture by aqueous quenching and extractive methods as is known in the art. In some instances the resulting 1-amino-3-[3-(thieno[2,3-d] isoxazol-3-yl)phenoxy]propan-2-ol of structure (1a) crystallizes from the reaction mixture either directly or on aqueous quenching, and may be isolated by filtration and purified by methods well known in the art.

In step J, a 1-amino-3-[3-(1-methyl-1H-thieno[3,2-c] pyrazol-3-yl)-phenoxy]propan-2-ol of structure (1a) (X=N—CH$_3$) may be prepared by treating a thieno[3,2-c] pyrazole-epoxide of structure (11) with a suitable primary or secondary amine (15).

For example, a solution of an amine (15) such as 1,2,3, 4-tetrahydroisoquinoline in a suitable solvent such as ethanol is treated with a solution of a thieno[3,2-c]pyrazole-epoxide of structure (11) and a suitable solvent such as ethanol. The mixture is agitated and heated to about the reflux temperature of the mixture for a suitable period, typically overnight, under an inert atmosphere such as argon. The mixture is concentrated and the 1-amino-3-[3-(1-methyl-1H-thieno[3,2-c]pyrazol-3-yl)-phenoxy]propan-2-ol of structure (1a) (X=N—CH$_3$) is recovered from the residue by chromatographic methods as are well known in the art.

In step K, a 2-alkoxy-3-[3-(thieno[2,3-d]isoxazol-3-yl) phenoxy]propylamine compound (1b) (X=O) is prepared by treating a 1-amino-3-[3-(thieno[2,3-d]isoxazol-3-yl)phenoxy]propan-2-ol compound (1a) with a suitable base and an appropriate alkylating agent.

For example, a solution of a 1-amino-3-[3-(thieno[2,3-d]isoxazol-3-yl)phenoxy]-propan-2-ol of structure (1a) such as (2R)-1-benzylamino-3-[3-(thieno[2,3-d]isoxazol-3-yl)phenoxy]-propan-2-ol in a suitable aprotic solvent such as tetrahydrofuran is treated with about an equivalent of appropriate base such as potassium bis(trimethylsilyl)amide at about $-20°$ C. under a nitrogen atmosphere. After stirring for about one hour at about $-20°$ C., the mixture is treated with about an equivalent of a suitable alkylating agent such as dimethylsulfate and allowed to warm to room temperature over about 2 hours. The resulting (2R)-benzyl-[2-methoxy-3-[3-(thieno[2,3-d]isoxazol-3-yl)-phenoxy]propyl]amine (1b) (X=O, $R_1$=OCH$_3$, $R_2$=$R_3$=$R_4$=H) may be recovered from the reaction mixture by aqueous quenching and extractive methods as is known in the art, and then purified by chromatography. By using about two equivalents of a suitable base such as potassium bis(trimethylsilyl)amide and about two equivalents of a suitable alkylating agent such as dimethylsulfate under similar conditions, the corresponding (2R)-benzyl-[2-methoxy-3-(3-(thieno[2,3-d]isoxazol-3-yl-phenoxy)propyl]methylamine of structure (1b) (X=O, $R_1$=OCH$_3$, $R_3$=CH$_3$, $R_2$=$R_4$=H) may be obtained.

In Scheme II, step L, a 1-amino-3-(3-thieno[2,3-d]isoxazol-3-yl)-propan-2-ol compound (1a) (X=O) is prepared by treating a monosulfonyl ester of the primary alcohol group of a 1-hydroxy-3-(3-thieno[2,3-d]isoxazol-3-yl)-propan-2-ol (14) with a suitable primary or secondary amine (15).

For example, a solution of toluene-4-sulfonic acid (S)-2-hydroxy-2-methyl-3-(3-thieno[2,3-d]isoxazol-3-yl-phenoxy)-propyl ester and a suitable solvent such as tetrahydrofuran is treated dropwise at about $0°$ C. with a solution of a primary amine (15) such as benzylamine and a suitable solvent such as tetrahydrofuran. An appropriate base such as potassium carbonate may be added as an acid scavenger if needed. Stir overnight at room temperature, concentrate in vacuo and partition the residue between ethyl acetate (100 mL) and water (100 mL). The organic phase is concentrated and the resulting (2R)-(−)-1-benzylamino-2-methyl-3-(3-thieno[2,3-d]isoxazol-3-yl-phenoxy)propan-2-ol (1a) (X=O) is recovered from the residue by chromatographic methods as are well known in the art.

In Scheme III, step M, an oxirane-methanamine of structure (17) is prepared by methods well known in the art.

In step N, an 1-amino-3-(3-thieno[2,3-d]isoxazol-3-yl)-propan-2-ol compound 1 (X=O) is prepared by treating an oxirane-methanamine (17) with the anion of an appropriately substituted thieno[2,3-d]isoxazole (9).

For example, a solution of a thieno[2,3-d]isoxazol (9) such as 3-thieno[2,3-d]isoxazol-3-yl-phenol in a suitable aprotic solvent such as dimethylformamide is treated with a suitable base such as potassium t-butoxide at about room temperature. The resultant solution is treated with an oxirane-methanamine of structure (17) such as N-methyl-N-(phenylmethyl)oxirane-methanamine and stirred for about two hours at room temperature. The reaction is quenched with water and the 1-amino-3-[3-(thieno[2,3-d]isoxazol-3-yl)phenoxy]propan-2-ol of structure (1a) may be recovered by extractive methods as is known in the art.

The $D_4$ binding profile of the present compounds indicates their utility as pharmaceuticals that may be useful as a neuroleptic for the treatment of various conditions in which $D_4$ receptor stimulation is implicated, such as for the treatment of anxiety and schizophrenia. Accordingly, in another of its aspects, the present invention provides pharmaceutical compositions useful to treat $D_4$-related medical conditions in which a compound of Formula I is present in an amount effective to antagonize $D_4$ receptor stimulation, together with a pharmaceutically acceptable carrier. In another of its aspects, the invention provides a method for treating medical conditions for which a $D_4$ antagonist is indicated, which comprises the step of administering to the patient an amount of a compound of Formula II effective to antagonize $D_4$ receptor stimulation, and a pharmaceutically acceptable carrier therefor.

For use in medicine, the compounds of the present invention can be administered in a standard pharmaceutical composition. The present invention therefore provides, in a further aspect, pharmaceutical compositions comprising a pharmaceutically acceptable carrier and a Formula I compound or a pharmaceutically acceptable salt, solvate, or hydrate thereof, in an amount effective to antagonize $D_4$ receptor stimulation.

In treating a patient afflicted with a condition described above, a compound of formula (I) can be administered in any form or mode which makes the compound bioavailable in therapeutically effective amounts, including orally, sublingually, buccally, subcutaneously, intramuscularly, intravenously, transdermally, intranasally, rectally, topically, and the like. One skilled in the art of preparing formulations can determine the proper form and mode of administration depending upon the particular characteristics of the compound selected for the condition or disease to be treated, the stage of the disease, the condition of the patient and other relevant circumstances. For example, see Remington's Pharmaceutical Sciences, 18th Edition, Mack Publishing Co. (1990), incorporated herein by reference.

The compounds of Formula I can be administered alone or in the form of a pharmaceutical composition in combination with pharmaceutically acceptable carriers, the proportion and nature of which are determined by the solubility and chemical properties of the compound selected, the chosen route of administration, standard pharmaceutical practice and other relevant criteria.

The compounds of the present invention may be administered orally, for example, in the form of tablets, troches, capsules, elixirs, suspensions, solutions, syrups, wafers, chewing gums and the like and may contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors.

The compounds of Formula (I) of this invention may also be administered topically, and when done so the carrier may suitably comprise a solution, ointment or gel base. The base, for example, may comprise one or more of petrolatum, lanolin, polyethylene glycols, bee wax, mineral oil, diluents such as water and alcohol, and emulsifiers and stabilizers.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials.

The dosage range at which the compounds of Formula I exhibit their ability to act therapeutically can vary depending upon the particular disease or condition being treated and its severity, the patient, the formulation, other underlying disease states that the patient is suffering from, and other medications that may be concurrently administered to the patient. Generally, the compounds of Formula I will exhibit their therapeutic activities at dosages of between about 0.001 mg/kg of patient body weight/day to about 100 mg/kg of patient body weight/day.

EXAMPLES

The following examples present typical syntheses as described in Schemes I, II, and III. These examples are understood to be illustrative only and are not intended to limit the scope of the present invention in any way. As used herein, the following terms have the indicated meanings: "g" refers to grams; "mmol" refers to millimoles; "mL" refers to milliliters; "µL" refers to microliters; "C" refers to degrees Celsius; "TLC" refers to thin layer chromatography; "LC/MS" refers to liquid chromatography mass spectrometry; "APCI" refers to atmospheric pressure chemical ionization; "mp" refers to melting point; "ppm" refers to parts per million; "TMS" refers to tetramethylsilane; "GC/MS" refers to gas chromatography/mass spectroscopy; "Hz" refers to hertz; "MHz" refers to megahertz; "NMR" refers to nuclear magnetic resonance; "M/S" refers to mass spectra; "IR" refers to infrared spectra.

The following Table sets forth references to relevant starting materials for syntheses described herein. Where no synthesis for the starting material is indicated, the starting material is either known, available commercially, or can be prepared by conventional means. The United States patents cited in the Table and elsewhere are herein incorporated by reference.

TABLE 1

References for Starting Materials

| Compound Name | Structure | Reference | Example # Where Used |
|---|---|---|---|
| 4-(6-fluoro-1H-indazol-3-yl)piperazine dihydrochloride | 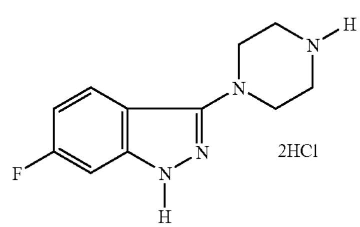 | U.S. Pat. No. 4,954,503, example 33 | 11 |
| 4-(5-methoxy-1H-indazol-3-yl)piperazine | 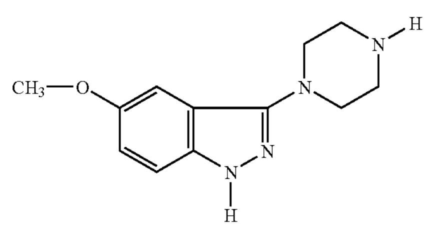 | U.S. Pat. No. 4,954,503, Example 10 | 12 |
| 4-(6-fluorobenzo[d]isoxazol-3-yl)piperidine | 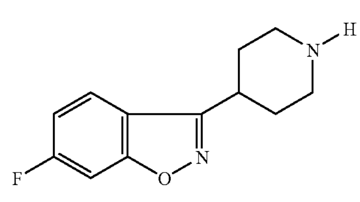 | U.S. Pat. No. 4,355,037, example 35 | 13, 65, 90 |
| 4-(6-chlorobenzo[d]isoxazol-3-yl)piperidine hydrochloride | 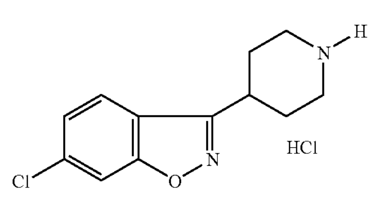 | U.S. Pat. No. 4,355,037, example 40 | 14 |

TABLE 1-continued

References for Starting Materials

| Compound Name | Structure | Reference | Example # Where Used |
|---|---|---|---|
| 3-(1,2-benzisoxazol-3-yl)-8-azabicyclo[3,2,1]octane hydrochloride | 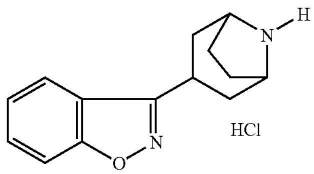 | U.S. Pat. No. 5,234,931; U.S. Pat. No. 5,340,936; U.S. Pat. No. 5,334,599; Example 1 | 15 |
| 3-(1-piperazinyl)-1,2-benzisothiazole | 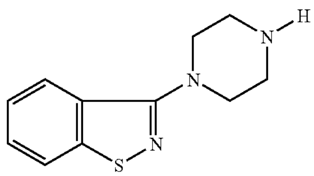 | J. Med. Chem., 1986, 29, 359–369; | 16 |
| 4-(6-fluoro-1,2-benzisothiazol-3-yl)-1-piperidinecarboxaldehyde | 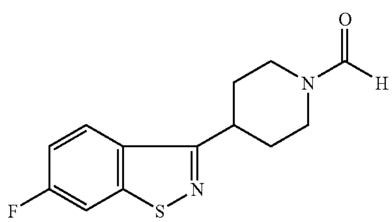 | Tetrahedron Letters, 1993, 34(41), 6525–6528 | 17 |
| 1-(6-fluorobenzo[b]thien-3-yl)piperazine maleate | 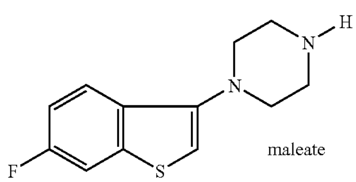 | U.S. Pat. No. 5,143,923 Example 26 | 18 |
| 1-[2-(trifluoromethyl)-phenyl]piperazine | 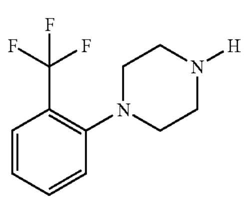 | J. Med. Chem. 1997, 40, 2674–2687 | 52 |
| 3-(3-epoxymethoxyphenyl)-thieno[2,3-d]isoxazole (racemic) | 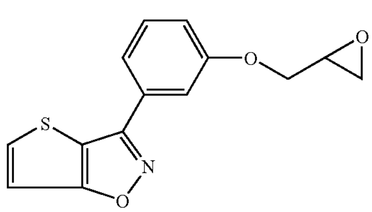 | U.S. Pat. No. 4,728,651, Example 25 | 56 |
| 3-aminomethylthiophene | 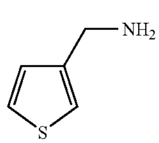 | M. R. Bryce et al., Synthetic Metals, 1988, 26, 153–168 | 24, 59, 83 |

TABLE 1-continued

References for Starting Materials

| Compound Name | Structure | Reference | Example # Where Used |
|---|---|---|---|
| 4-(3-chlorophenoxy)-piperidine | 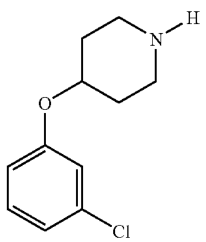 | J. Med. Chem., 1978, 21, 309–312 | 89 |
| 4-(6-methoxy-benzo[d]isoxzaol-3-yl)piperazine hydrobromide | 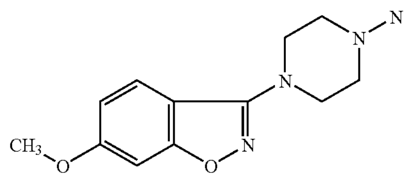 | U.S. Pat. No. 5,852,022, example 1 | 92 |
| (±)-N-methyl-N-(phenylmethyl)oxirane-methanamine | 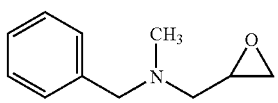 | U.S. Pat. No. 3,336,196 | 112 |

High Performance Liquid Chromatography (HPLC)— Atmospheric Pressure Chemical Ionisation Mass Spectrometry (APCI/MS) Analysis of Examples Conditions for product analysis are readily ascertainable by one skilled in the art. The following conditions represent typical analytic parameters.

Where indicated, analysis of examples was performed using a Waters HPLC system and a Finnigan TSQ-700 mass spectrometer (conditions 1, 3, 4, 5) or TSQ-710 mass spectrometer (conditions 2, 6) equipped with an atmospheric pressure chemical ionization (hereinafter "APCI") source. HPLC columns or cartridges were obtained from YMC Inc., 3233 Burnt Mill Drive, Wilmington, N.C. 28403, and Waters Corporation, 34 Maple Street, Milford, Mass. 01757. The conditions for the analysis are summarized as follows, and the particular set of conditions used is indicated by reference in the description of the example.

HPLC-APCI/MS Conditions 1:
A) 95/5/0.1% Water/Acetonitrile/Trifluororacetic acid
B) 5/95/0.85% Water/Acetonitrile/Trifluororacetic acid The column was a YMCbasic (4 mm×50 mm) cartridge. The initial HPLC conditions consisted of 100% (A) flowing at 1 mL/minute. After the 5 µL injection a linear gradient was performed so that at 4 minutes the HPLC conditions were 100% (B). These conditions were then held for 1.9 minutes at which time the system switched back to initial conditions and equilibrated for the next analysis for 5 minutes.

HPLC-APCI/MS Conditions 2:
C) 95/5/0.5% Water/Acetonitrile/Acetic acid
D) 5/95/0.5% Water/Acetonitrile/Acetic acid The column was a YMC ODS-A (4 mm×50 mm) cartridge. The initial HPLC conditions consisted of 70% (C) and 30% (D) flowing at 1 mL/minute. After the 5 µL injection a linear gradient was performed so that at 4 minutes the HPLC conditions were 100% (D). These conditions were then held for 2 minutes at which time the system switched back to initial conditions and equilibrated for the next analysis.

HPLC-APCI/MS Conditions 3:
E) 95/5/0.1% Water/Acetonitrile/Trifluororoacetic acid
F) 5/95/0.85% Water/Acetonitrile/Trifluororoacetic acid The column was a YMC ODS-AQ (4 mm×50 mm) cartridge. The initial HPLC conditions consisted of 100% (E) flowing at 1 mL/minute. After the 5 µL injection a linear gradient was performed so that at 4 minutes the HPLC conditions were 100% (F). These conditions were then held for 5 minutes at which time the system switched back to initial conditions and equilibrated for the next analysis.

HPLC-APCI/MS Conditions 4:
G) 95/5/0.1% Water/Acetonitrile/Trifluororoacetic acid
H) 5/95/0.85% Water/Acetonitrile/Trifluororoacetic acid The column was a YMC ODS-AQ (4 mm×50 mm) cartridge. The initial HPLC conditions consisted of 100% (G) flowing at 1 mL/minute. After the 5 µL injection a linear gradient was performed so that at 4 minutes the HPLC conditions were 100% (H). These conditions were then held for 2 minutes at which time the system switched back to initial conditions and equilibrated for the next analysis.

HPLC-APCI/MS Conditions 5:
I) 95/5/0.1% Water/Acetonitrile/Trifluororoacetic acid
J) 5/95/0.85% Water/Acetonitrile/Trifluororoacetic acid The column was a YMC ODS-AQ (4 mm×50 mm) cartridge. The initial HPLC conditions consisted of 95% (I) 5% (J) flowing at 1 mL/minute. After the 5 µL injection a linear gradient was performed so that at 4 minutes the HPLC conditions were 100% (J). These conditions were then held for 2 minutes at which time the system switched back to initial conditions and equilibrated for the next analysis.

HPLC-APCI/MS Conditions 6:
K) 95/5/0.1% Water/Acetonitrile/Trifluororoacetic acid
L) 5/95/0.85% Water/Acetonitrile/Trifluororoacetic acid The column was a YMC ODS-A (4 mm×50 mm) cartridge. The initial HPLC conditions consisted of 60% (K) 40% (B) flowing at 1 mL/minute. After the 5 μL injection a linear gradient was performed so that at 1 minute the HPLC conditions were 100% (L). These conditions were then held for 4 minutes at which time the system switched back to initial conditions and equilibrated for the next analysis.

Example 1

Preparation of 3-thieno[2,3-d]isoxazol-3-yl-phenol (Scheme 1, Compound 9)

Step A

Preparation of (3-bromothiophen-2-yl)-(3-methoxyphenyl)methanone (Scheme 1, Compound 5)

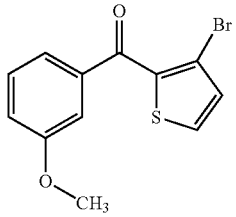

Add phenyllithium (210 mL, 0.44 mol, 2.1 M in cyclohexane) dropwise, to a cold (5° C.) mixture of 3-bromothiophene (66 g, 0.40 mol) and ether (400 mL) over two hours to form the lithiated thiophene intermediate. Add the lithiated thiophene intermediate mixture to a cold (−70° C.) mixture of THF and m-methoxybenzoyl chloride over three hours, then quench the reaction with water and extract with ether. Wash the ether with 10% NaOH and water, dry (MgSO$_4$), filter and evaporate to yield an oil. Purify the oil by column (alumina) chromatography, eluting with hexane up to 50% ether in hexane. Distill the product in vacuo and recrystallize (ether:hexane) to obtain the title compound (89.1 g, 75% Yield), m.p. 40° C.

Step B

Preparation of (3-bromothiophen-2-yl)-(3-methoxyphenyl)methanone oxime (Scheme I, Compound 7)

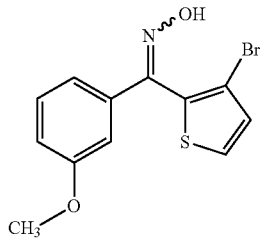

Stir a mixture of (3-bromothiophen-2-yl)-(3-methoxyphenyl)methanone (7 g, 0.024 mol), hydroxylamine hydrochloride (3.09 g, 0.048 mol) and pyridine (40 mL) overnight at room temperature, and then heat the mixture (100° C.–105° C.) for four hours. TLC (dichloromethane) shows that the reaction is complete. Quench the reaction mixture with water and extract with ether (three times). Wash the ether phase with HCl (3N) and water, dry (MgSO$_4$), filter and concentrate to yield an oil that solidifies. Recrystallize the solid from ether:hexane to obtain the title compound (6.4 g, 87% Yield), m.p. 102–103° C.

Step C

Preparation of 3-(3-methoxyphenyl)thieno[2,3-d]isoxazole (Scheme I, Compound 8)

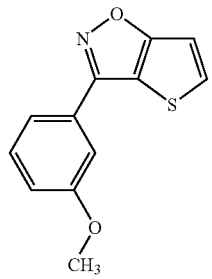

Reflux a mixture of (3-bromothiophen-2-yl)-(3-methoxyphenyl)methanone oxime (10 g, 0.032 mol), KOH (3.6 g, 0.064 mol dissolved in 10 mL water) and 2-ethoxyethanol (100 mL) under nitrogen for one hour at 105–110° C. Add copper chloride (0.16 g, 0.0016 mol) whereupon the reaction mixture becomes dark brown in color. Heat the reaction for an additional one hour. Add water and extract the organics into ether. Wash the ether phase with water, dry (MgSO$_4$), filter and concentrate to yield an oil. Purify the oil by column (alumina) chromatography, and elute with 15% ether in hexane to obtain white crystals. Recrystallize the crystals from ether:hexane to yield the title compound (5 g, 68% Yield), m.p. 51–52° C.

Step D

Preparation of 3-thieno[2,3-d]isoxazol-3-yl-phenol (Scheme I, Compound 9)

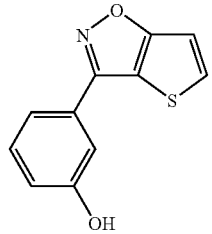

Combine and stir under nitrogen at 140° C. a mixture of 3-(3-methoxyphenyl)thieno[2,3-d]isoxazole (8 g, 0.035 mol) and pyridine hydrochloride (80 g, 0.69 mol) for nine hours. TLC (ethyl acetate: dichloromethane) shows the reaction is complete. Cool the reaction mixture to room temperature, and pour into water. Extract the organics into ethyl acetate:ether (50:50), and wash once with HCl (3N), three times with water, dry (MgSO$_4$) and evaporate to yield an oil. Purify the oil by column (silica) chromatography, eluting with 5% ethyl acetate in dichloromethane, to yield a solid. Recrystallize this solid (ether:hexane) to obtain the title compound as an orange/tan solid (3 g, 40% yield), m.p. 114–116° C.

Example 2

Preparation of 3-(4-hydroxyphenyl)thieno[2,3-d]isoxazole

Step E

Preparation of (3-bromo-thiophen-2-yl)-(4-methoxyphenyl)-methanone (Scheme I, Compound 5)

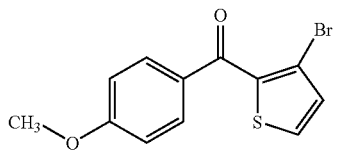

Treat a stirred, chilled (0° C.) solution of 3-bromothiophene (20 g, 0.123 mol) and dichloromethane (150 mL) with titanium tetrachloride in dichloromethane (184 mL, 1.0M) at such a rate as to maintain the temperature below 5° C. Add dropwise a solution of 4-methoxybenzoyl chloride (20.9 g, 0.123 mol) and dichloromethane (75 mL) at such a rate as to maintain the temperature below 5° C. Stir one hour at 0–5° C., then quench the reaction by addition of ice (100 mL) and 6N hydrochloric acid at such a rate that the internal temperature remains at or below 10° C. Add more water (100 mL), separate the organic phase, wash with water, dry (Na$_2$SO$_4$), filter and evaporate to an oil which solidifies. Recrystallize the solid from ether to afford the title compound as off-white crystals (19.7 g, 54%).

Step B

Preparation of (3-bromothiophen-2-yl)-(4-methoxyphenyl)-methanone oxime (Scheme I, Compound 7)

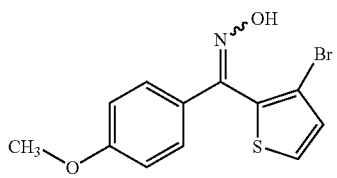

Stir a solution of (3-bromothiophen-2-yl)-(4-methoxyphenyl)methanone (19.65 g, 0.066 mol), hydroxylamine hydrochloride (6.89 g, 0.099 mol), and pyridine (30 mL) at 85° C. under nitrogen for five hours. Pour the reaction mixture into a mixture of water (120 mL) and toluene (180 mL), and chill to 0° C. Add concentrated hydrochloric acid (approximately 30 mL) dropwise with cooling to adjust to pH 1–2. Filter the mixture and wash the solid with toluene and water. Separate the phases and extract the acidic aqueous phase with toluene. Wash the combined toluene phases twice with water, dry (Na$_2$SO$_4$), filter and evaporate. Combine the residue from the toluene extracts with the previously obtained solid filter cake, and triturate the mixture with petroleum ether. Filter the mixture and dry in vacuo at 60° C. to give the title compound as a white solid (19.6 g, 95% yield).

Step C

Preparation of 3-(4-methoxyphenyl)thieno[2,3-d]isoxazole (Scheme I, Compound 8)

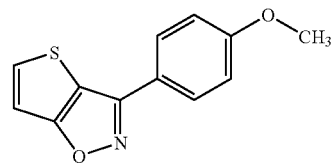

Add to a solution of water (20 mL) and potassium hydroxide (7.2 g, 0.128 mol), (3-bromothiophen-2-yl)-(4-methoxyphenyl)-methanone oxime (19.6 g, 0.0628 mol) and 2-methoxyethanol (200 mL). Stir the solution and then treat under nitrogen with copper powder (1.0 g, 0.0157 g-atom 0.25 equiv.). Heat the stirred mixture to 60° C. for four hours, and then pour into a mixture of water (800 mL) and dichloromethane (450 mL). Add hydrochloric acid (10 mL, 6N), filter the mixture, and wash the copper with dichloromethane and water. Separate the filtrate, and wash the organic phase twice with water, dry (Na$_2$SO$_4$), filter and evaporate. Dissolve the residue in dichloromethane and chromatograph the compound over alumina, eluted with 4:1 heptane:dichloromethane, and then with 3:1 heptane:dichloromethane. Evaporate the fractions, triturate the residue with heptane, and collect the solid and dry at 60° C. to give the title compound (9.3 g, 64% yield), m.p. 93–94° C.

ANALYSIS: Calculated for $C_{12}H_9NO_2S$: 62.32% C, 3.92% H, 6.06% N. Found 62.23% C, 3.73% H, 5.96% N.

Step D

Preparation of 3-(4-hydroxyphenyl)thieno[2,3-d]isoxazole (Scheme I, Compound 9)

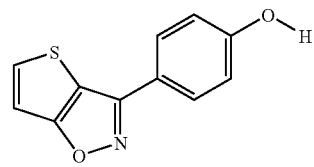

Treat a stirred solution of 3-(4-methoxyphenyl)thieno[2,3-d]isoxazole (9.10 g, 0.0394 mol) in 1,2-dichloroethane (100 mL) portionwise with aluminum chloride (15.74 g, 0.118 mol). The mixture is stirred at 70° C. for 1.5 hours, cool to room temperature, and decant into a mixture of concentrated hydrochloric acid (50 mL) and ice (160 g). Stir the mixture for 0.5 hour, filter through Celite, separate the phases and extract the filter cake with dichloromethane. Also use the dichloromethane extract to extract the aqueous phase. Combine the organic phases, wash twice with water, dry (Na$_2$SO$_4$), filter and evaporate. Purify the crude material by flash chromatography on silica gel using gradient elution with 1 to 2% methanol in dichloromethane. Concentrate the desired fractions to afford the title compound as a tan solid (7.1 g, 83% yield).

Example 3

Preparation of 3-(1-methyl-1H-thieno[3,2-c]pyrazol-3-yl)phenol

Steps B and C

Preparation of 3-(3-methoxyphenyl)-1-methyl-1H-thieno[3,2-c]pyrazole: (Compound 8, Scheme I)

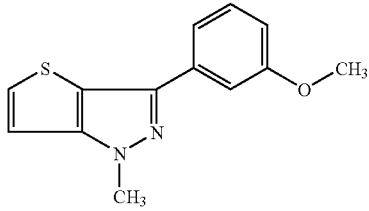

Stir a mixture of (3-bromothiophen-2-yl)-(3-methoxyphenyl)methanone (20 g; 0.067 mol.; example 1, step A), ethylene glycol (134 mL) and methylhydrazine (17 g, 0.37 mol) under nitrogen at 120°14 130° for 2.5 hours. Cool to room temperature, quench with water (200 mL) and extract with ether (4×200 mL). Dry the combined ether extracts (MgSO$_4$), filter and evaporate the filtrate to an oil. Purify the oil by HPLC (3:1 hexane/ethyl acetate) to give a solid (9 g) and recrystallize from ether to give the title compound as crystals (8.2 g), m.p. 99°–101° C.

Analysis: Calculated for C$_{13}$H$_{12}$N$_2$OS: 63.90% C, 4.95% H, 11.47% N. Found: 63.63% C, 5.03%, 11.52% N.

Step D

Preparation of 3-(1-methyl-1H-thieno[3,2-c]pyrazol-3-yl)phenol: (Compound 9, Scheme I)

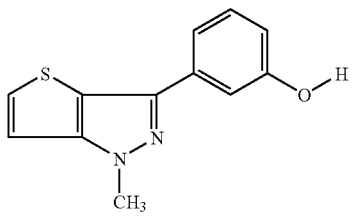

Treat a stirred solution of 3-(3-methoxyphenyl)-1-methyl-1H-thieno[3,2-c]pyrazole (7.5 g, 0.031 mol.) and dichloromethane (51 mL) dropwise with a solution of boron tribromide (41 mL, 0.041 mol., 1.0M in dichloromethane) under nitrogen. After 2.5 hours, quench with hydrochloric acid (50 mL, 1N) and ether/ethyl acetate (50 mL), and stir until both phases are clear. Wash the organic phase with water, dry (MgSO$_4$), filter and evaporate to give an oil. Purify the oil by HPLC (silica gel, elution with 10% methanol in dichloromethane) to give a light tan solid. Purify the solid further by column chromatography (silica gel, elution with 5% methanol in dichloromethane) to give a white solid (3.5 g, 49% yield).

Example 4

Preparation of (R)-3-(3-epoxymethoxyphenyl)thieno[2,3-d]isoxazole (Compound 11, Scheme II) MDL 812673

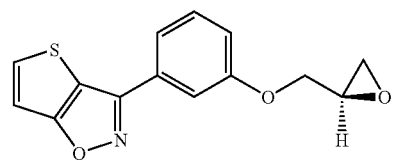

Step F, Scheme II: From (2R)-(−)glycidyl tosylate:

Add a solution of 3-thieno[2,3-d]isoxazol-3-yl-phenol (Example 1, 0.42 g, 0.0019 mol) and dimethylformamide (4 mL) dropwise under nitrogen to a stirred mixture of sodium hydride (0.051 g, 0.0021 mol, 60% oil dispersion) and dry dimethylformamide (4 mL). Stir 20 min., and add a solution of (2R)-(−)glycidyl tosylate (recrystallize first from dichloromethane/heptane) and dimethylformamide (4 mL). Stir overnight at room temperature under nitrogen, pour into water (100 mL) and extract with ethyl acetate. Dry the extract (Na$_2$SO$_4$), filter and evaporate, and purify the residue by flash chromatography (silica gel, gradient elution with 0 to 1% methanol in dichloromethane), and recrystallize the recovered product from ethanol to afford the title compound, (0.47 g, 89% yield), m.p. 86–87° C., $[\alpha]_D^{20}$ −3.45° (c=0.985, CHCl$_3$).

ANALYSIS: Calculated for: 61.53% C, 4.06% H, 5.12% N. Found: 61.66% C, 3.68% H, 5.02% N.

Step F, Scheme II: From (2R)-(−)-glycidyl 3-nitrobenzenesulfonate

Add a solution of 3-thieno[2,3-d]isoxazol-3-yl-phenol (Example 1, 1.36 g, 0.0063 mol) and dry dimethylformamide (14 mL) to a stirred suspension of sodium hydride (0.27 g, 0.0068 mol, 60% in oil) and dry dimethylformamide (14 mL). Cool the mixture to 0° C. and add dropwise a solution of (2R)-(−)-glycidyl 3-nitrobenzenesulfonate (1.61 g, 0.0062 mol, recrystallized twice from absolute ethanol) and dimethylformamide (14 mL). Stir at 0° C. for 0.5 hour, warm to room temperature over 40 min., and stir at room temperature for 10 min. Pour the mixture into ice/ammonium chloride; extract with ether; wash the extract with cold 0.5N NaOH solution and brine; dry (Na$_2$SO$_4$); filter; and concentrate to afford a white solid. Purify the solid by flash chromatography on silica gel by dissolving in ethyl acetate, applying to the column and eluting with 25% ethyl acetate in heptane to afford the title compound as a white solid (1.15 g, 68% yield), >98% ee by chiral HPLC (Chiralcel OD column, 0.75 mL/min, 90% heptane/10% isopropyl alcohol, UV detector (237 nm). The material may be recrystallized from absolute ethanol.

Example 5

Preparation of (R)-3-(4-epoxymethoxyphenyl)thieno[2,3-d]isoxazole (Compound 11, Scheme II)

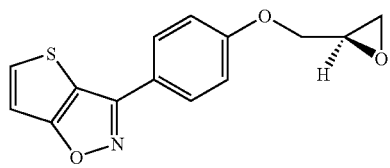

MDL 812943

Step F, Scheme II

Add sodium hydride (0.95 g, 0.039 mol, 1.2 equiv, 60% dispersion in oil) to a stirred solution of 3-(4-hydroxyphenyl)thieno[2,3-d]isoxazole (example 2, 7.1 g, 0.0329 mol, example 2) and dimethylformamide (50 mL) under nitrogen at room temperature. After 20 min., add dropwise a solution of (2R)-(−)glycidyl tosylate and dimethylformamide (35 mL) and stir at room temperature overnight. Pour into ice water (700 mL), stir 20 min., filter and wash with water. Dissolve the solid in dichloromethane, wash with brine, dry ($Na_2SO_4$), filter, and evaporate the appropriate fractions. Purify the crude material by preparative HPLC (silica gel, gradient elution with 0–1% methanol in dichloromethane), collect and evaporate the desired fractions, and recrystallize the material from ethyl acetate to give the title compound (5.6 g, 62% yield), m.p. 130–133° C., $[\alpha]_D^{20}$ −5.10 (c=0.59, $CHCl_3$).

ANALYSIS: Calculated for $C_{14}H_{11}NO_3S$: 61.53% C, 4.06% H, 5.12% N. Found: 61.36% C, 3.98% H, 5.06% N.

Example 6

Preparation of (R)-3-[3-(2-methyloxiranylmethoxy)phenyl]thieno[2,3-d]isoxazole (Compound 11, Scheme II)

MDL 812724

Step G, Scheme II

Preparation of (R)-2-methyl-3-(3-thieno[2,3-d]isoxazol-3-yl-phenoxy)propane-1,2-diol (Compound 13, Scheme II)

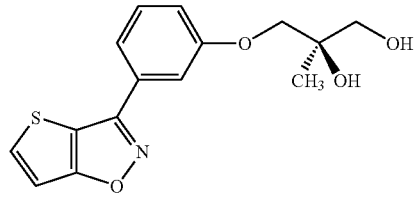

MDL 812722

Add potassium t-butoxide (2.83 g, 0.0253 mol) in small portions to a stirred solution of 3-thieno[2,3-d]isoxazol-3-yl-phenol (example 1, 5.5 g, 0.0253 mol) and dimethylformamide (50 mL), and then add (2S)-(+)-2-methylglycidyl-4-nitrobenzoate (2.0 g, 0.00843 mol, Aldrich Chemical Company). Stir at room temperature for 30 min., warm to 50° C. and stir for two hours. Cool to room temperature, pour into water (100 mL) and partition between ethyl acetate (500 mL) and water (500 mL). Separate the organic phase and extract the aqueous phase with ethyl acetate (2×300 mL). Combine the organic phases, dry ($MgSO_4$), filter and concentrate in vacuo. Chromatograph the residue over silica gel, elute with 18:1 dichloromethane:methanol and concentrate the desired fractions to give a dark oil (2.7 g). Triturate the oil with dichloromethane/hexanes to give the title compound as a brown solid (2.0 g, 78% yield), m.p. 97–98° C., MS (chemical ionization, $CH_4$) $MH^+$ 306.

ANALYSIS: Calculated for $C_{15}H_{15}NO_4S$: 59.00% C, 4.95% H, 4.59% N. Found: 59.23% C, 4.73% H, 4.51% N.

Step H, Scheme II

Preparation of toluene-4-sulfonic acid (S)-2-hydroxy-2-methyl-3-(3-thieno[2,3-d]isoxazol-3-yl-phenoxy)-propyl ester (Compound 14, Scheme II)

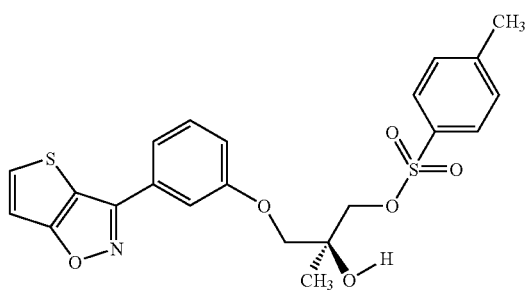

Treat a stirred solution of (R)-2-methyl-3-(3-thieno[2,3-d]isoxazol-3-yl-phenoxy)propane-1,2-diol (1.95 g, 0.0064 mol) and dichloromethane (20 mL) with p-toluenesulfonyl chloride (2.44 g, 0.0127 mol) and then with pyridine (1.0 mL, 0.013 mol). Stir the mixture for 48 hours at room temperature, dilute with dichloromethane (200 mL) and wash with hydrochloric acid (200 mL, 2N). Separate the organic phase, dry ($MgSO_4$), filter and concentrate in vacuo. Purify the residue by flash chromatography on silica gel and elute with 1:2 ethyl acetate:petroleum ether to afford the title monotosylate as a white foam (2.45 g).

Step I, Scheme II

Preparation of (R)-b 3-[3-(2-methyloxiranylmethoxy)phenyl]thieno[2,3-d]isoxazole (Compound 11, Scheme II)

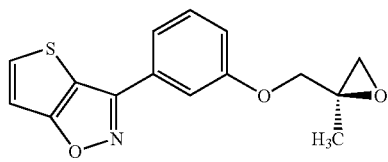

Add potassium t-butoxide (0.67 g, 0.006 mol) in small portions to a chilled (0° C.) stirred solution of toluene-4-sulfonic acid (S)-2-hydroxy-2-methyl-3-(3-thieno[2,3-d]isoxazol-3-yl-phenoxy)-propyl ester (2.45 g, 0.00533 mol)

and tetrahydrofuran (40 mL). Stir one hour at 0° C. and partition between ethyl acetate and water. Separate the organic phase, dry (MgSO₄), filter, and concentrate in vacuo. Recrystallize the residue from ether-hexane to give the title compound (1.33 g, 87% yield), m.p. 84–85° C., MS (chemical ionization, CH₄) MH⁺ 288.

Analysis: Calculated for C₁₅H₁₃NO₃S: 62.70% C, 4.56% H, 4.87% N; Found: 62.21% C, 4.41% H, 4.70% N.

Example 7

Preparation of (S)-3-[3-(2-methyloxiranylmethoxy) phenyl]thieno[2,3-d]isoxazole (Compound 11, Scheme II)

MDL 813101

Step G, Scheme II

Preparation of (S)-2-methyl-3-(3-thieno[2,3-d]isoxazol-3-yl-phenoxy)propane-1,2-diol (Compound 13, Scheme II)

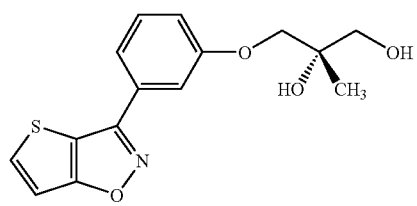

MDL 812722

Add potassium t-butoxide (14.2 g, 0.126 mol) in small portions under nitrogen to a stirred solution of 3-thieno[2,3-d]isoxazol-3-yl-phenol (example 1, 27.5 g, 0.126 mol) and dimethylformamide (200 mL). After 10 min. add (2R)-(+)-2-methylglycidyl-4-nitrobenzoate (10.0 g, 0.0422 mol, Aldrich Chemical Company) and rinse through with dimethylformamide (50 mL). Heat to 50° C. and stir for two hours. Pour into ice water (1200 mL) and extract with ethyl acetate (add ammonium chloride to aid separation). Separate the organic phase, dry (Na₂SO₄), filter and concentrate in vacuo. Purify the residue by flash chromatography over silica gel, elute with 4–7% methanol in dichloromethane and concentrate the desired fractions. Purify again by preparative chromatography (silica gel, elute with 3–5% methanol in dichloromethane) to give a tan solid (6.8 g, 53% yield).

Step H, Scheme II

Preparation of toluene-4-sulfonic acid (R)-2-hydroxy-2-methyl-3-(3-thieno[2,3-d]isoxazol-3-yl-phenoxy)-propyl ester (Compound 14, Scheme II)

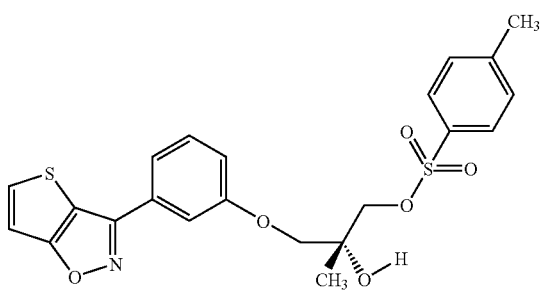

Treat a stirred solution of (S)-2-methyl-3-(3-thieno[2,3-d]isoxazol-3-yl-phenoxy)propane-1,2-diol (6.70 g, 0.0.0219 mol) and dichloromethane (75 mL) with p-toluenesulfonyl chloride (8.37 g, 0.0439 mol) and then with pyridine (3.47 g, 0.0439 mol) under nitrogen. Stir the mixture for 48 hours at room temperature under nitrogen, dilute with dichloromethane (200 mL) and wash twice with hydrochloric acid (1N). Separate the organic phase, dry (Na₂SO4), filter and concentrate in vacuo. Purify the residue by preparative HPLC (silica gel), and elute with 0–5% methanol in dichloromethane to afford the title monotosylate as a tan foam (6.8 g, 67% yield).

Step I, Scheme II

Preparation of (S)-3-[3-(2-methyloxiranylmethoxy) phenyl]thieno[2,3-d]isoxazole (Compound 11, Scheme II)

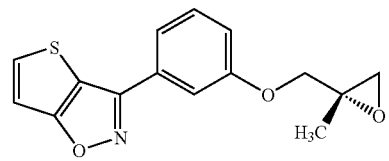

Add potassium t-butoxide (1.99 g, 0.0.0178 mol) in small portions to a chilled (0° C.) stirred solution of toluene-4-sulfonic acid (R)-2-hydroxy-2-methyl-3-(3-thieno[2,3-d] isoxazol-3-yl-phenoxy)-propyl ester (6.80 g, 0.0148 mol) and tetrahydrofuran (75 mL) under nitrogen. Stir 30 min. at 0° C., pour into water (300 mL), and extract with ethyl acetate. Separate the organic phase, dry (Na₂SO4), filter, and concentrate in vacuo. Recrystallize the residual yellow solid from ethyl acetate to give the title epoxide (4.1 g, 96% yield), m.p. 85–86° C., $[\alpha]_D^{20}$ –8.37° (c=0.645, CHCl₃); chiral HPLC (Chiracel OD column, 90:10 heptane:isopropyl alcohol, 0.75 mL/min., UV detection at 237 µM) 94.4% ee.

Analysis: Calculated for C₁₅H₁₃NO₃S: 62.70% C, 4.56% H, 4.87% N; Found: 62.60% C, 4.52% H, 4.76% N.

Example 8

Step F, Scheme II

Preparation of (R)-1-methyl-3-(3-oxiranylmethoxyphenyl)-1H-thieno[3,2-c]pyrazole (Compound 11, Scheme II)

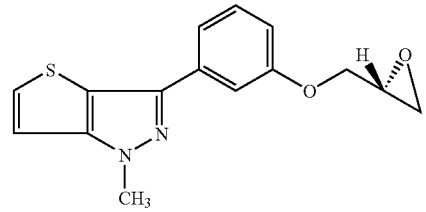

Add sodium hydride (0.14 g, 0.0059 mol) at 0° C. under nitrogen to a stirred solution of 3-(1-methyl-1H-thieno[3,2-c]pyrazol-3-yl)phenol (example 3) (1.13 g, 0.0049 mol) and dimethylformamide (50 mL). Stir 15 min. and add (R)-(–)-glycidyl tosylate (1.12 g, 0.0049 mol, Aldrich Chemical Company), and then stir overnight at room temperature. Pour into water (400 mL), add a little ammonium chloride and extract with ethyl acetate. Dry (Na$_2$SO$_4$), filter and evaporate the extract, and purify the residue by flash chromatography (silica gel, elute with dichloromethane and then with 2% methanol in dichloromethane). Concentrate the desired fractions to afford the title compound as a white solid (0.85 g, 60% yield).

Example 9

Step J, Scheme II

Preparation of (2R)-1-[(N-benzyl-N-methyl)amino]-3-[3-thieno[2,3-d]isoxazol-3-yl)phenoxy]-2-propanol hydrochloride (compound 1a, Scheme II)

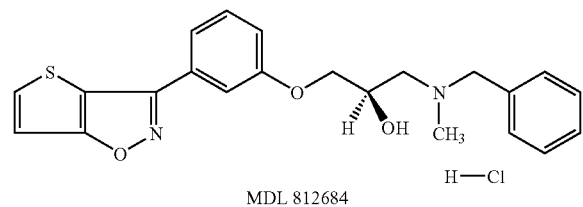

MDL 812684

Add N-benzyl-N-methylamine (0.47 g, 0.0039 mol, Aldrich Chemical Company) to a suspension of (R)-3-(3-epoxymethoxyphenyl)thieno[2,3-d]isoxazole (example 4, 0.902 g, 0.0033 mol) and 95% ethanol (11.5 mL). Stir the suspension at 60° C. for 0.5 hour and then stir at 80° C. for 0.5 hour. Concentrate the solution to an oil, dissolve the oil in ethyl acetate and purify by flash chromatography on silica gel eluting with 25% ethyl acetate in heptane. Combine the desired fractions and concentrate to an oil (0.98 g, 75% yield). HPLC analysis on a Chiracel OJ column (237 nM, 0.75 mL/min., 70% heptane/30% (0.5% diethylamine in ethanol) shows 98% ee. Convert the oil to the hydrochloride salt with ethereal hydrogen chloride, dry under high vacuum, and recrystallize from isopropanol to provide the title compound, m.p. 150–152° C., $[\alpha]_D^{21}$+22.1° (c=1.07, CH$_3$OH); MS (chemical ionization, CH$_4$) MH$^+$ 395.

Analysis: Calculated for C$_{22}$H$_{23}$ClN$_2$O$_3$S: 61.32% C, 5.38% H, 6.50% N; Found: 61.14% C, 5.28% H, 6.43% N.

Example 10

Step J, Scheme II

Preparation of (2R)-1-[4-(2-methoxyphenyl)-piperazin-1-yl]-3-(3-thieno[2,3-d]isoxazol-3-yl-phenoxy)-propan-2-ol hydrochloride (compound 1a, Scheme II)

MDL 812828

Add potassium t-butoxide (1.12 g, 0.010 mol) to a stirred, chilled (10° C.) solution of 3-thieno[2,3-d]isoxazol-3-yl-phenol (Example 1, 2.17 g, 0.010 mol) and N-methylpyrrolidinone (30 mL). After 0.5 hour, cool the mixture to 0–5° C. and add (2R)-(–)glycidyl 3-nitrobenzenesulfonate (2.59 g, 0.010 mol, 99% ee, Aldrich Chemical Company). After 2 hours, add potassium t-butoxide (0.2 equiv.) and (2R)-(–)-glycidyl 3-nitrobenzenesulfonate (0.1 equiv.), and stir for 2 hours at which time the reaction is 96% complete [monitor the reaction by HPLC [Waters µ-Bondpack C-18 column, 0.1N ammonium formate/acetonitrile (40:60), flow rate 1 mL/min., UV detection at 240 nm]. Treat the solution of (R)-3-(3-epoxymethoxyphenyl)thieno[2,3-d]isoxazole with 1-(2-methoxyphenyl)piperazine (5.80 g, 0.030 mol, Aldrich Chemical Company) and heat to 70° C. for six hours. Cool the reaction mixture to 23° C., pour into water (300 mL) and extract with ethyl acetate (1×300 mL, 2×100 mL). Wash the combined extracts with 5% sodium chloride solution (3.50 mL), dry (K$_2$CO$_3$), filter and concentrate in vacuo. Purify the material twice by elution through silica gel with ethyl acetate to give the free base of the title compound, 4.15 g (89% yield). Convert to the hydrochloride salt by treating an absolute ethanol (20 mL) solution of the free base with 37% hydrochloric acid solution (0.74 mL) at 25° C. Concentrate the slurry to 10 mL final volume, chill to –20° C. for 0.5 hour, isolate and dry (90° C., 4 hours) the filter cake to afford the title compound, 3.55 g (79% yield), m.p. 179–181° C., >98% ee by chiral HPLC, MS (chemical ionization, CH$_4$), MH$^+$ 466; NMR (DMSO-d$_6$) and IR (KBr) consistent with the structure of the title compound.

Analysis: Calculated for C$_{25}$H$_{27}$N$_3$O$_4$S.HCl: 59.81% C, 5.62% H, 8.37% N; Found: 59.53% C, 5.51% H, 8.18% N.

Examples 11–22

Step J, Scheme II

Examples 11–22 were prepared on the same scale using the techniques of parallel synthesis. Experimental conditions are described in detail for Example 11, with any variations in procedures being noted for Examples 12–22.

Example 11

Preparation of (2R)-1-[4-(6-fluoro-1H-indazol-3-yl)-piperazin-1-yl]-3-(3-thieno[2,3-d]isoxazol-3-yl-phenoxy)-propan-2-ol

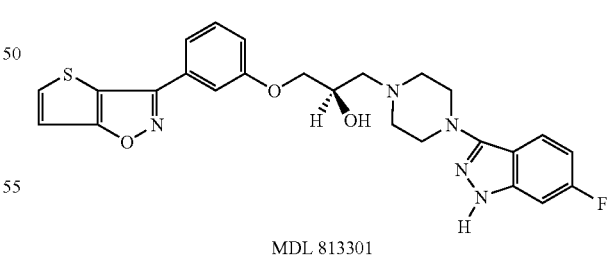

MDL 813301

Add 6 mL of a solution of (R)-3-(3-epoxymethoxyphenyl)thieno[2,3-d]isoxazole (example 4, 0.22 g, 0.008 mol) in acetonitrile-water (4:1) to a mixture of 4-(6-fluoro-1H-indazol-3-yl)piperazine dihydrochloride (0.37 g, 0.0012 mol, prepare as described in U.S. Pat. No. 4,954,503, example 33) and potassium carbonate (0.40 g, 0.0029 mol), and shake and heat at 70° C. for 4.5 hours. Allow to cool to room temperature overnight and concentrate under nitrogen to remove the acetonitrile. Extract the residue by adding ethyl acetate (5 mL) and water (2 mL), separate the phases and extract again with ethyl acetate (5 mL). Dry (Na$_2$SO$_4$) the combined ethyl acetate phases, filter and evaporate. Purify the crude material using a 5 g silica gel SepPak cartridge eluting with ethyl acetate. Further purify the desired fractions using a 5 g silica gel SepPak cartridge eluting with heptane:ethyl acetate (1:2) and then with ethyl acetate to give the title compound (0.32 g, 81% yield), m.p. 97–99° C., LC/MS (APCI), m/e 494 (MH$^+$), retention time 4.21 min.

Analysis: Calculated for C$_{25}$H$_{24}$FN$_5$O$_3$S: 60.84% C, 4.90% H, 14.19% N; Found: 60.47% C, 4.85% H, 13.79% N.

Example 12

Preparation of (2R)-1-[4-(5-methoxy-1H-indazol-3-yl)-piperazin-1-yl]-3-(3-thieno[2,3-d]isoxazol-3-yl-phenoxy)-propan-2-ol

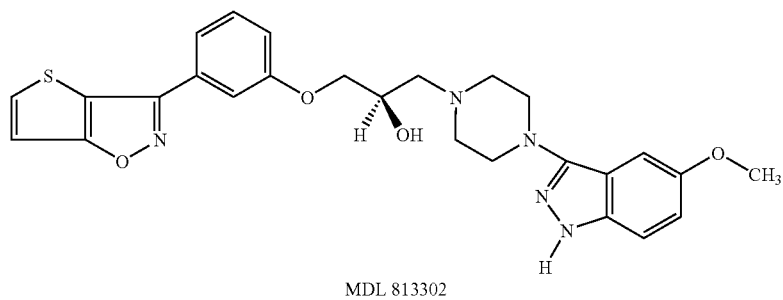

MDL 813302

Perform the synthesis under conditions as described for Example 11 using 4-(5-methoxy-1H-indazol-3-yl)piperazine free base without potassium carbonate to afford the title compound (0.29 g, 72% yield), m.p. 84–86° C., LC/MS (APCI) m/e 506 (MH$^+$), retention time 4.15 min.

Analysis: Calculated for C$_{26}$H$_{27}$N$_5$O$_4$S: 61.77% C, 5.38% H, 13.85% N; Found: 61.37% C, 5.15% H, 13.66% N.

Example 13

Preparation of (2R)-1-[4-(6-fluorobenzo[d]isoxazol-3-yl)piperidin-1-yl]-3-(3-thieno[2,3-d]isoxazol-3-yl-phenoxy)-propan-2-ol

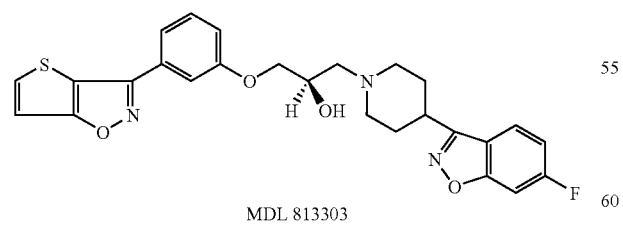

MDL 813303

Perform the synthesis under conditions as described for Example 11 using 4-(6-fluorobenzo[d]isoxazol-3-yl)piperidine free base without potassium carbonate to afford the title compound (0.34 g, 86% yield), LC/MS (APCI) m/e 494 (MH$^+$), retention time 4.28 min.

Example 14

Preparation of (2R)-1-[4-(6-chlorobenzo[d]isoxazol-3-yl)piperidin-1-yl]-3-(3-thieno[2,3-d]isoxazol-3-yl-phenoxy)-propan-2-ol

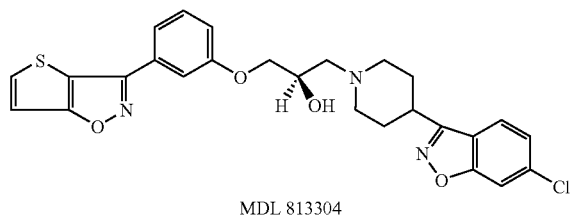

MDL 813304

Perform the synthesis under conditions as described for Example 11 using 4-(6-chlorobenzo[d]isoxzaol-3-yl)piperidine hydrochloride with potassium carbonate (0.20 g, 0.0015 mol). Filter the precipitate from the cooled reaction mixture, extract the filtrate, combine the precipitate with the organic extract, and continue as described in example 11 to afford the title compound (0.37 g, 91% yield), LC/MS (APCI) m/e 510 (MH$^+$), retention time 4.37 min.

Example 15

Preparation of (2R)-1-(3-benzo[d]isoxazol-3-yl-8-azabicyclo[3.2.1]oct-8-yl-3-(3-thieno[2,3-d]isoxazol-3-yl-phenoxy)propan-2-ol

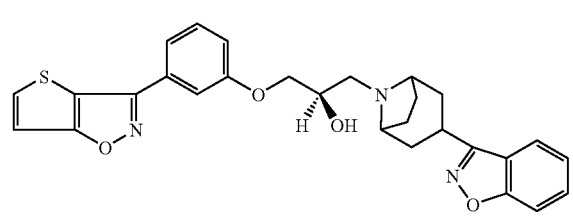

MDL 813305

Perform the synthesis under conditions as described for Example 11 using 3-(1,2-benzisoxasol-3-yl)-8-azabicyclo[3,

Example 16

Preparation of (2R)-1-(4-benzo[d]isothiazol-3-yl-piperazin-1-yl)-3-(3-thieno[2,3-d]isoxazol-3-yl-phenoxy)-propan-2-ol

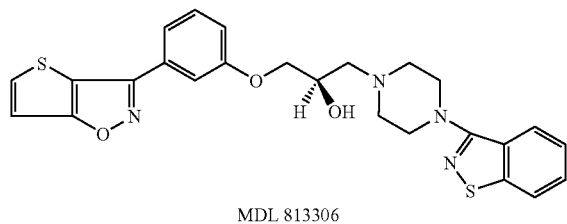

MDL 813306

Perform the synthesis under conditions as described for Example 11 using 3-(1-piperazinyl)-1,2-benzisothiazole free base. Filter the precipitate from the cooled reaction mixture, extract the filtrate, combine the precipitate with the organic extract, and continue as described in example 11 to afford the title compound (0.35 g, 89% yield); LC/MS (APCI) m/e 493 (MH+), retention time 4.32 min.

Example 17

Preparation of (2R)-1-[4-(6-fluorobenzo[d]isothiazol-3-yl)-piperdin-1-yl]-3-(3-thieno[2,3-d]isoxazol-3-yl-phenoxy)propan-2-ol

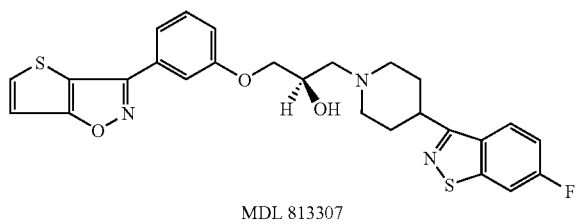

MDL 813307

Reflux a solution of 4-(6-fluoro-1,2-benzisothiazol-3-yl)-1-piperidinecarboxaldehyde (Tetrahedron Lett., 1993, 34, 6525–6528, 12 g, 0.045 mol), 3N hydrochloric acid and ethanol (100 mL) for 3 hours. Stir at ambient temperature for 16 hours, add water and stir with ice bath chilling while adding sodium hydroxide solution until the mixture was basic. Extract with ethyl acetate, wash the extract with water, dry (MgSO$_4$), filter and concentrate the filtrate to afford an oil which solidified on standing to afford 6-fluoro-3-(4-piperidinyl)-1,2-benzisothiazole (9.2 g). React 6-fluoro-3-(4-piperidinyl)-1,2-benzisothiazole under conditions as described for Example 11 to afford the title compound (0.25 g, 61% yield), LC/MS (APCI) m/e 510 (MH+), retention time 4.38 min.

Example 18

Preparation of (2R)-1-[4-(6-fluorobenzo[b]thiophen-3-yl)piperazin-1-yl]-3-(3-thieno[2,3-d]isoxazol-3-yl-phenoxy)-propan-2-ol

MDL 813308

Perform the synthesis under conditions as described for Example 11 using 1-(6-fluorobenzo[b]thien-3-yl)piperazine maleate and potassium carbonate (0.20 g, 0.0015 mol) to afford the title compound (0.38 g, 93% yield), LC/MS (APCI) m/e 510 (MH+), retention time 4.44 min.

Example 19

Preparation of (2R)-1-(4-pyrimidin-2-yl-piperazin-1-yl)-3-(3-thieno[2,3-d]isoxazol-3-yl-phenoxy)-propan-2-ol

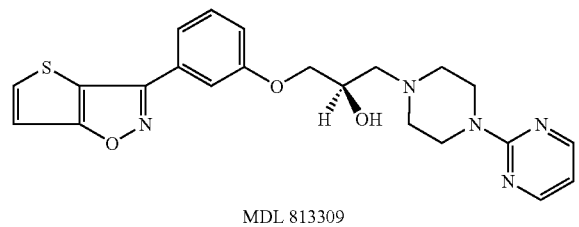

MDL 813309

Perform the synthesis under conditions as described for Example 11 using 1-(2-pyrimidyl)piperazine dihydrochloride (0.29 g, 0.0012 mol, Aldrich Chemical Company) and potassium carbonate (0.40 g, 0.0029 mol) to afford the title compound (0.28 g, 80% yield), LC/MS (APCI) m/e 438 (MH+), retention time 4.04 min.

Example 20

Preparation of (2R)-1-(4-pyridin-2-yl-piperazin-1-yl)-3-(3-thieno[2,3-d]isoxazol-3-yl-phenoxy)-propan-2-ol

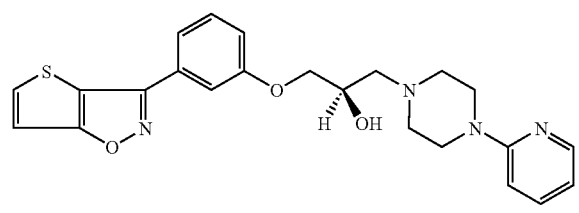

MDL 813310

Perform the synthesis under conditions as described for Example 11 using 1-(2-pyridyl)piperazine (0.20 g, 0.0012 mol, Aldrich Chemical Company) to afford the title compound (0.29 g, 83% yield), LC/MS (APCI) m/e 437 (MH+), retention time 3.41 min.

Example 21

Preparation of (2R)-1-(4-benzylpiperidin-1-yl)-3-(3-thieno[2,3-d]isoxazol-3-yl-phenoxy)-propan-2-ol

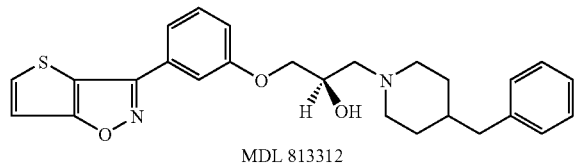

MDL 813312

Perform the synthesis under conditions as described for Example 11 using 4-benzylpiperidine (0.21 g, 0.0012 mol, Aldrich Chemical Company) to afford the title compound (0.31 g, 86% yield), LC/MS (APCI) m/e 449 (MH+), retention time 4.39 min.

Example 22

Preparation of (2R)-1-[(pyridin-2-ylmethyl)-amino]-3-(3-thieno[2,3-d]isoxazol-3-yl-phenoxy)-propan-2-ol

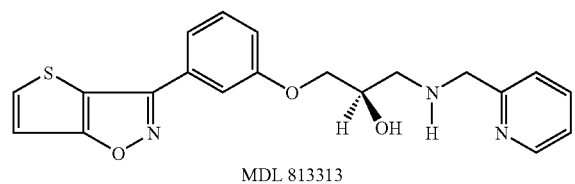

MDL 813313

Perform the synthesis under conditions as described for Example 11 using 2-(aminomethyl)pyridine (0.44 g, 0.004 mol, Aldrich Chemical Company) to afford the title compound (0.24 g, 79% yield), thin layer chromatography (silica gel, ethyl acetate:methanol 19:1) $R_f$ 0.10; LC/MS (APCI) m/e 382 (MH+), retention time 4.0 min.

Examples 23–26

Step J, Scheme II

Examples 23–26 were prepared on the same scale using the techniques of parallel synthesis. Experimental conditions are described in detail for Example 23, with any variations in procedures being noted for Examples 24–26.

Example 23

Preparation of (2R)-1-[(naphthalen-1-ylmethyl)-amino]-3-(4-thieno[2,3-d]isoxazol-3-yl-phenoxy)-propan-2-ol

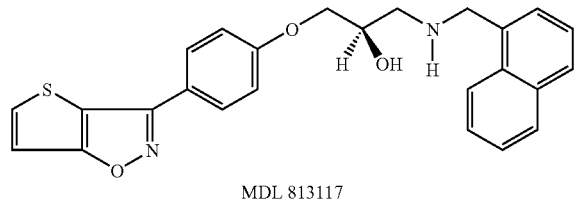

MDL 813117

Prepare a solution of 1-naphthalenemethylamine (0.129 g, 0.000823 mol, Aldrich Chemical Company) in sufficient ethanol to give 3 mL of solution (0.2774 M). Add this solution to a solution of (R)-3-(4-epoxymethoxyphenyl)thieno[2,3-d]isoxazole (example 5, 0.15 g, 0.000549 mol) and ethanol (3 mL). Shake the reaction mixture under Argon at reflux temperature for four hours. Cool and concentrate to remove the solvent. Purify the residue by flash chromatography (40 g silica gel) eluting in step gradient fashion sequentially with 3% methanol in dichloromethane, 5% methanol in dichloromethane, 10% methanol in dichloromethane and finally with 85:15:1 dichloromethane:methanol:-ammonium hydroxide solution. The desired fractions were combined and concentrated to afford the title compound (0.0925 g, 39%), LC/MS (APCI, condition 6) m/e 431 (MH+), retention time 2.31 min.

Example 24

Preparation of (2R)-1-(4-thieno[2,3-d]isoxazol-3-yl-phenoxy)-3-[(thiophen-3-ylmethyl)-amino]-propan-2-ol

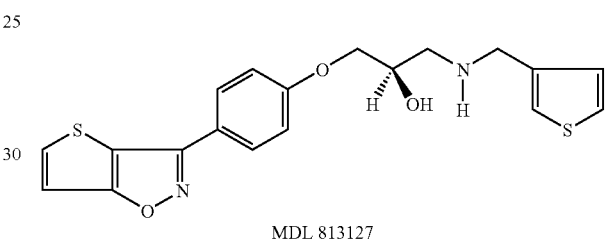

MDL 813127

Prepare 3-(aminomethyl)thiophene hydrochloride as described by M. R. Bryce et al., *Synthetic Metals* (1988), 26, 153–168. Condense 3-(aminomethyl)thiophene hydrochloride (0.000823 mole) with the example 5 epoxide (0.000549 mol) and triethylamine (slight excess) under conditions as described for Example 23 to afford the title compound (0.103 g, 49% yield), LC/MS (APCI, condition 6) m/e 387 (MH+), retention time 1.43 min.

Example 25

Preparation of (2R)-1-[(furan-2-ylmethyl)-amino]-3-(4-thieno[2,3-d]isoxazol-3-yl-phenoxy)propan-2-ol

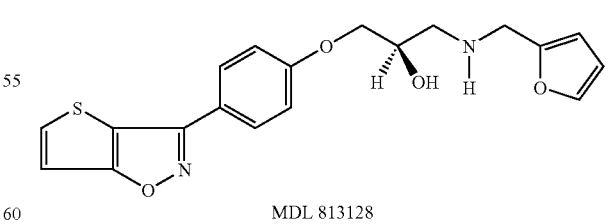

MDL 813128

Condense furfurylamine (0.000823 mole) with the example 5 epoxide (0.000549 mol) under conditions as described for Example 23 to afford the title compound (0.148 g, 73% yield), LC/MS (APCI, condition 6) m/e 371 (MH+), retention time 1.15 min.

Example 26

Preparation of (2R)-1-(4-thieno[2,3-d]isoxazol-3-yl-phenoxy)-3-[(thiophen-2-ylmethyl)-amino]-propan-2-ol

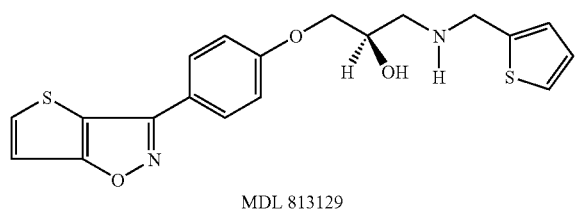

MDL 813129

Condense 2-(aminomethyl)thiophene [0.000823 mole] with the example 5 epoxide (0.000549 mol) under conditions as described for Example 23 to afford the title compound (0.166 g, 78% yield), LC/MS (APCI, condition 6) m/e 387 (MH+), retention time 1.35 min.

Example 27

Preparation of (2R)-2-methyl-1-(3-thieno[2,3-d]isoxazol-3-yl-phenoxy)-3-[thienophen-2-ylmethyl)-amino-propan-2-ol maleate

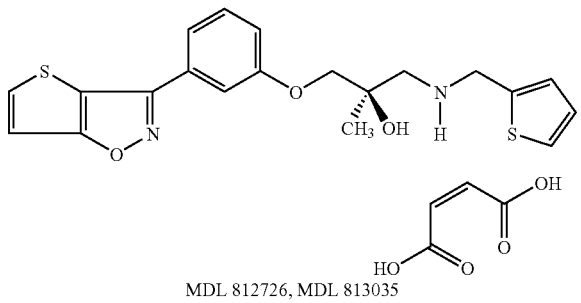

MDL 812726, MDL 813035

Treat a solution of (R)-3-[3-(2-methyloxiranylmethoxy)phenyl]thieno[2,3-d]isoxazole (example 6, 0.25 g, 0.00105 mol) and acetonitrile (5 mL) at room temperature with lithium tetrafluoroborate (0.0985 g, 0.00105 mol) and then add 2-(aminomethyl)thiophene [108 μL, 0.00105 mol]. Stir the mixture overnight, dilute with ethyl acetate (100 mL) and wash with water (50 mL). Separate, dry (MgSO$_4$) and concentrate the organic phase in vacuo. Flash chromatograph the residue (silica gel, 9:1 dichloromethane:methanol), and collect and concentrate the desired fractions to give the free base of the title compound (0.20 g). Treat the free base with maleic acid and recrystallize to give the title compound (0.27 g, 50% yield), m.p. 120–121° C.; MS (Cl, CH$_4$), m/e 401 (MH+).

ANALYSIS: Calculated for $C_{24}H_{24}N_2O_7S_2$: 55.80% C, 4.68% H, 5.42% N; Found: 55.59% C, 4.60% H, 5.24% N.

Examples 28–40

Step J, Scheme II

Examples 28–40 were prepared on the same scale using the techniques of parallel synthesis. Experimental conditions are described in detail for Example 28, with any variations in procedures being noted for Examples 29–40.

Example 28

Preparation of (2R)-1-(4-methoxybenzylamino)-2-methyl-3-(3-thieno[2,3-d]isoxazol-3-yl-phenoxy)-propan-2-ol

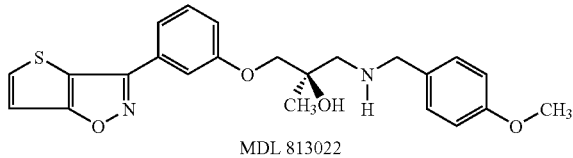

MDL 813022

Add 1 mL of a solution of 4-methoxybenzylamine (0.048 g, 0.00035 mol, Aldrich Chemical Company) and ethanol to 3 mL of a solution of (R)-3-[3-(2-methyloxiranylmethoxy)phenyl]-thieno[2,3-d]isoxazole (example 6, 0.10 g, 0.00035 mol) and ethanol. Shake the reaction mixture under argon at reflux temperature for four hours in a Bohdan apparatus. Cool and concentrate in vacuo to remove the solvent. Purify the residue by flash chromatography (Waters SepPak, silica gel) eluting in step gradient fashion sequentially with 2:1 heptane:ethyl acetate and then with 10:1 dichloromethane:methanol to afford after concentration of the desired fractions the title compound (0.063 g, 42% yield).

Example 29

Preparation of (2R)-1-(2-methoxybenzylamino)-2-methyl-3-(3-thieno[2,3-d]isoxazol-3-yl-phenoxy)-propan-2-ol

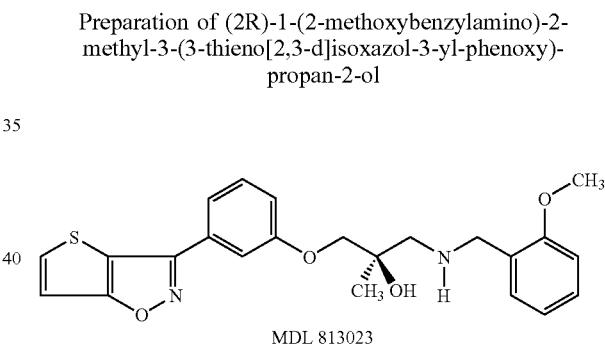

MDL 813023

Condense 2-methoxybenzylamine (0.00035 mole, Aldrich Chemical Company) with the example 6 epoxide (0.00035 mol) under conditions as described for Example 28 to afford the title compound (0.061 g, 40% yield).

Example 30

Preparation of (2R)-1-(4-chlorobenzylamino)-2-methyl-3-(3-thieno[2,3-d]isoxazol-3-ylphenoxy)-propan-2-ol

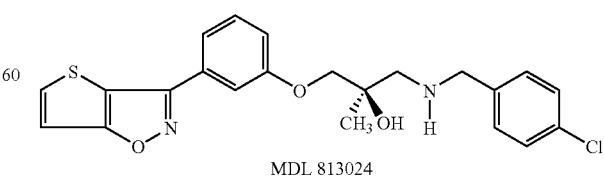

MDL 813024

Condense 4-chlorobenzylamine (0.00035 mole, Aldrich Chemical Company) with the example 6 epoxide (0.00035 mol) under conditions as described for Example 28 to afford the title compound (0.063 g, 42% yield).

Example 31

Preparation of (2R)-1-(4-fluorobenzylamino)-2-methyl-3-(3-thieno[2,3-d]isoxazol-3-ylphenoxy)-propan-2-ol

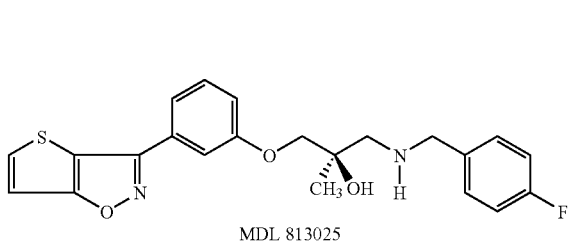

MDL 813025

Condense 4-fluorobenzylamine (0.00035 mole, Aldrich Chemical Company) with the example 6 epoxide (0.00035 mol) under conditions as described for Example 28 to afford the title compound (0.051 g, 35% yield).

Example 32

Preparation of (2R)-1-(2-fluorobenzylamino)-2-methyl-3-(3-thieno[2,3-d]isoxazol-3-ylphenoxy)-propan-2-ol

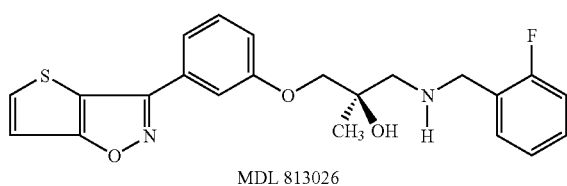

MDL 813026

Condense 2-fluorobenzylamine (0.00035 mole, Aldrich Chemical Company) with the example 6 epoxide (0.00035 mol) under conditions as described for Example 28 to afford the title compound (0.045 g, 31% yield).

Example 33

Preparation of (2R)-1-[(furan-2-ylmethyl)-amino]-2-methyl-3-(3-thieno[2,3-d]isoxazol-3-yl-phenoxy)-propan-2-ol

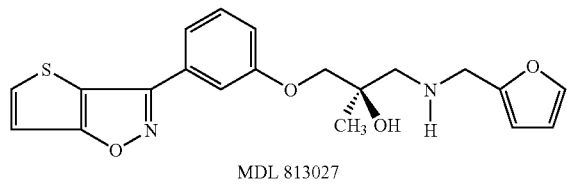

MDL 813027

Condense furfurylamine (0.00035 mole, Aldrich Chemical Company) with the example 6 epoxide (0.00035 mol) under conditions as described for Example 28 to afford the title compound (0.049 g, 36% yield).

Example 34

Preparation of (2R)-2-methyl-1-(3-thieno[2,3-d]isoxazol-3-yl-phenoxy)-3-(4-trifluoromethylbenzylamino)-propan-2-ol

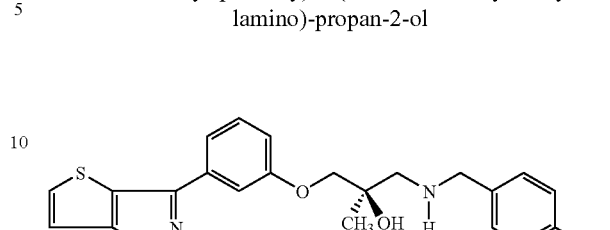

MDL 813028

Condense 4-(trifluoromethyl)benzylamine (0.00035 mole, Aldrich Chemical Company) with the example 6 epoxide (0.00035 mol) under conditions as described for Example 28 to afford the title compound (0.067 g, 41% yield).

Example 35

Preparation of (2R)-2-methyl-1-[1(R)-phenylethylamino]-3-(3-thieno[2,3-d]isoxazol]-3-yl-phenoxy)-propan-2-ol

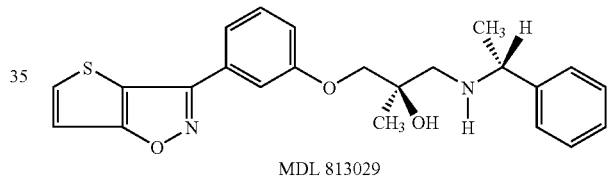

MDL 813029

Condense (R)-(+)-α-methyl)benzylamine (0.00035 mole, Aldrich Chemical Company) with the example 6 epoxide (0.00035 mol) under conditions as described for Example 28 to afford the title compound (0.067 g, 57% yield).

Example 36

Preparation of (2R)-2-methyl-1-[1(S)-phenylethylamino]-3-(3-thieno[2,3-d]isoxazol]-3-yl-phenoxy)-propan-2-ol

MDL 813030

Condense (S)-(−)-α-methyl)benzylamine (0.00035 mole, Aldrich Chemical Company) with the example 6 epoxide (0.00035 mol) under conditions as described for Example 28 to afford the title compound (0.065 g, 45% yield).

Example 37

Preparation of (2R)-2-methyl-1-[(naphthalen-1-ylmethyl)amino]-3-(3-thieno[2,3-d]isoxazol-3-yl-phenoxy)-propan-2-ol

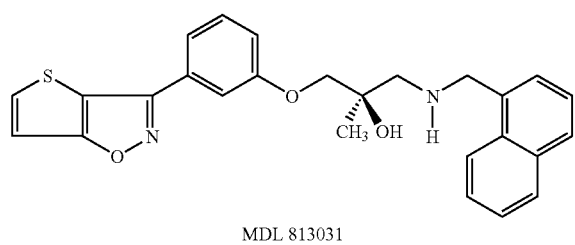

MDL 813031

Condense 1-naphthalenemethylamine (0.00035 mole, Aldrich Chemical Company) with the example 6 epoxide (0.00035 mol) under conditions as described for Example 28 to afford the title compound (0.066 g, 42% yield).

Example 38

Preparation of (2R)-2-methyl-1-[(pyridin-4-ylmethyl)-amino]-3-(3-thieno[2,3-d]isoxazol-3-yl-phenoxy)-propan-2-ol

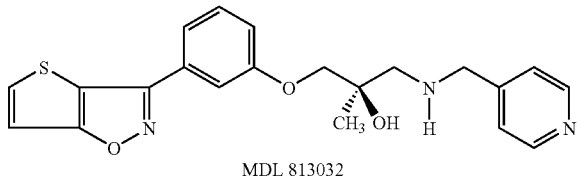

MDL 813032

Condense 4-(aminomethyl)pyridine (0.00035 mole, Aldrich Chemical Company) with the example 6 epoxide (0.00035 mol) under conditions as described for Example 28 to afford the title compound (0.009 g, 7% yield).

Example 39

Preparation of (2R)-2-methyl-1-[(pyridin-3-ylmethyl)-amino]-3-(3-thieno[2,3-d]isoxazol-3-yl-phenoxy)-propan-2-ol

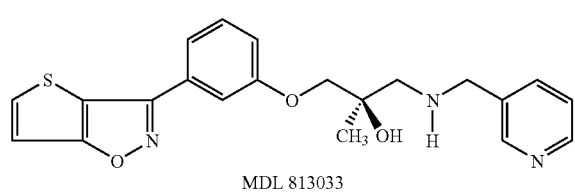

MDL 813033

Condense 3-(aminomethyl)pyridine (0.00035 mole, Aldrich Chemical Company) with the example 6 epoxide (0.00035 mol) under conditions as described for Example 28 to afford the title compound (0.035 g, 25% yield).

Example 40

Preparation of (2R)-2-methyl-1-[(pyridin-2-ylmethyl)-amino]-3-(3-thieno[2,3-d]isoxazol-3-yl-phenoxy)-propan-2-ol

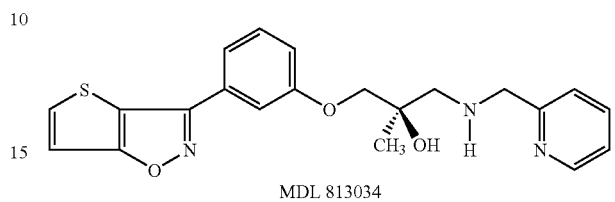

MDL 813034

Condense 2-(aminomethyl)pyridine (0.00035 mole, Aldrich Chemical Company) with the example 6 epoxide (0.00035 mol) under conditions as described for Example 28 to afford the title compound (0.124 g, 90% yield).

Example 41

Step J, Scheme II

Preparation of (2R)-1-[(furan-2-ylmethyl)amino]-3-(3-thieno[2,3-d]isoxazol-3-yl-phenoxy)-propan-2-ol hydrochloride

MDL 813054

Heat a solution of (R)-3-(3-epoxymethoxyphenyl)thieno[2,3-d]isoxazole (example 4, 0.55 g, 0.002 mol), furfurylamine (0.58 g, 0.006 mol, Aldrich Chemical Company) and absolute ethanol (20 mL) at 50° C. for 8 hours under nitrogen. Concentrate to remove the ethanol, dissolve the residue in ethyl acetate (50 mL), and wash with water (50 mL). Separate the phases and wash the aqueous phase with ethyl acetate (30 mL). Combine the ethyl acetate phases, dry (MgSO$_4$), filter and concentrate to give the crude product. Purify by column chromatography (1×12 inches, silica gel, elute with ethyl acetate). Concentrate the desired fractions, dissolve the residue in ethanol (20 mL), treat with one equivalent of HCl, dilute with ether, and collect and dry the precipitate to afford the title compound (0.53 g, 36%), m.p. 152–157° C.; MS (Cl, methane) m/e 371 (MH$^+$); HPLC: Nucleosil C$_{18}$ column, acetonitrile/0.1N ammonium formate (60:40), flow rate 1 mL/min, retention time 6.6 min.

Analysis: Calculated for C$_{19}$H$_{18}$N$_2$O$_4$S.HCl: 56.09% C, 4.71% H, 6.88% N; Found: 56.00% C, 4.55% H, 6.74% N.

Example 42

Step J, Scheme II

Preparation of (2R)-1-[(pyridin-3-ylmethyl)amino]-3-(3-thieno[2,3-d]isoxazol-3-ylphenoxy)-propan-2-ol dihydrochloride

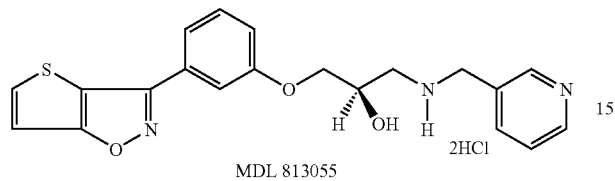

MDL 813055

Condense 3-methylaminopyridine (0.012 mole, Aldrich Chemical Company) with the example 4 epoxide (0.003 mol) at 90° C. under conditions as described for Example 41. Purify the crude material by column chromatography (1×12 inch, silica gel, elute sequentially with dichloromethane and methanol (3%, 6%, 10%) to afford the purified free base. Convert to the dihydrochloride salt as described using excess conc. HCl to afford the title compound (0.90 g, 45% yield), m.p. 210–213° C.; HPLC: Nucleosil $C_{18}$ column, acetonitrile/0.1N ammonium formate (60:40), flow rate 1 mL/min, retention time 6.8 min Analysis: Calculated for $C_{20}H_{19}N_3O_3S.2HCl$: 52.87% C, 4.66% H, 9.25% N; Found: 52.66% C, 4.85% H, 8.91% N.

Example 43

Step J, Scheme II

Preparation of (2R)-1-(2-hydroxy-2-phenylethylamino)-3-(3-thieno[2,3-d]isoxazol-3-yl-phenoxy) propan-2-ol hydrochloride

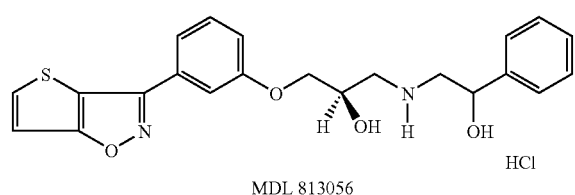

MDL 813056

Condense (±)-2-amino-1-phenylethanol (0.012 mole, Aldrich Chemical Company) with the example 4 epoxide (0.003 mol) in ethanol (25 mL) at reflux for 8.5 hours under conditions as otherwise described for Example 41. Purify the crude product by column chromatography (silica gel; elute with ethyl acetate, then ethyl acetate:methanol 4:1) and convert to the hydrochloride salt as described for Example 41 to give the title compound (0.20 g, 15%), m.p. 140–142° C.; MS (Cl, methane) m/e 411 (MH$^+$); HPLC: Nucleosil $C_{18}$ column, acetonitrile/0.1N ammonium formate (60:40), flow rate 1 mL/min, retention time 6.4 min Analysis: Calculated for $C_{22}H_{22}N_2O_4S.HCl$: 59.12% C, 5.19% H, 6.27% N; Found: 58.90% C, 5.10% H, 6.17% N.

Examples 44–52

Step J, Scheme II

Examples 44–52 were prepared on the same scale using the techniques of parallel synthesis. Experimental conditions are described in detail for Example 44, with any variations in procedures being noted for Examples 45–52.

Example 44

Preparation of (2R)-1-[4-(2-fluorophenyl)piperazin-1-yl]-3-(3-thieno[2,3-d]isoxazol-3-yl-phenoxy)-propan-2-ol

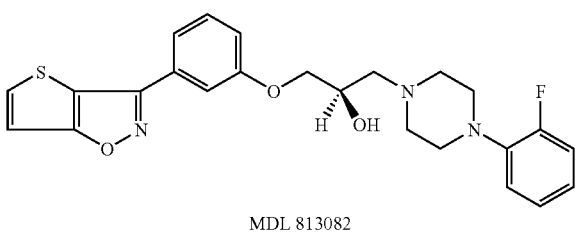

MDL 813082

To 1-(2-fluorophenyl)piperazine (0.135 g, 0.00075 mol, Aldrich Chemical Company), add a solution of (R)-3-(3-epoxymethoxyphenyl)thieno[2,3-d]isoxazole (example 4, 0.1367 g, 0.0005 mol) and acetonitrile:water (4:1, 5 mL). Heat in a capped scintillation vial at 70° C. for 4.5 hours, cool, evaporate some of the acetonitrile under a nitrogen stream, and add water (5 mL). Extract with ethyl acetate, and dry (Na$_2$SO$_4$) and evaporate the solvent under a nitrogen stream. Purify by chromatography on silica gel (Supelco Chamber, elute with ethyl acetate) and concentrate to give the title compound (0.10 g, 79%), m.p. 96–99° C., MS (Cl, methane) m/e 454 (MH$^+$).

Analysis: Calculated for $C_{24}H_{24}FN_3O_3S$: 63.56% C, 5.33% H, 6.26% N; Found: 63.41% C, 5.42% H, 9.07% N.

Example 45

Preparation of (2R)-1-[4-(4-fluorophenyl)piperzain-1-yl]-3-(3-thieno[2,3-d]isoxazol-3-yl-phenoxy)-propan-2-ol

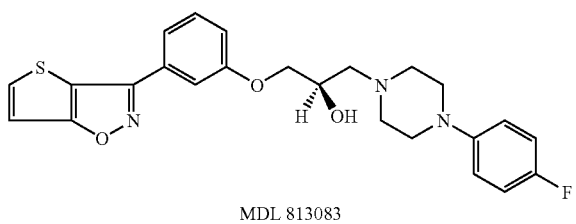

MDL 813083

Condense 1-(4-fluorophenyl)piperazine (0.00075 mole, Aldrich Chemical Company) with the example 4 epoxide (0.0005 mol) under conditions as described for Example 44. Add water to the evaporated reaction solution, and collect and dry the precipitate to afford the title compound (0.11 g, 81%), m.p. 117–119° C., MS (Cl, methane) m/e 454 (MH$^+$).

Analysis: Calculated for $C_{24}H_{24}FN_3O_3S$: 63.56% C, 5.33% H, 6.26% N; Found: 63.38% C, 5.32% H, 9.21% N.

Example 46

Preparation of (2R)-1-[4-(2-chlorophenyl)piperazin-1-yl]-3-(3-thieno[2,3-d]isoxazol-3-yl-phenoxy)-propan-2-ol

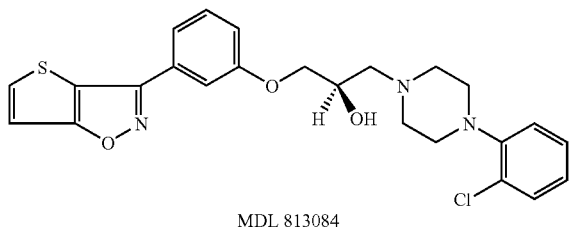

MDL 813084

Condense 1-(2-chlorophenyl)piperazine hydrochloride (0.00075 mole, Aldrich Chemical Company) with the example 4 epoxide (0.0005 mol) and potassium carbonate (1.2 equiv.) under conditions as described for Example 44 to afford the title compound (0.10 g, 81%), m.p. 83–86° C., MS (Cl, methane) m/e 470 (MH$^+$).

Analysis: Calculated for $C_{24}H_{24}ClN_3O_3S$: 61.33% C, 5.15% H, 8.94% N; Found: 61.25% C, 5.22% H, 8.76% N.

Example 47

Preparation of (2R)-1-[4-(3-chlorophenyl)piperazin-1-yl]-3-(3-thieno[2,3-d]isoxazol-3-yl-phenoxy)-propan-2-ol

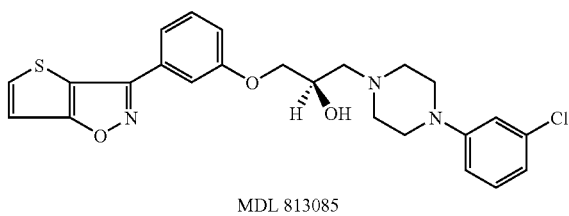

MDL 813085

Condense 1-(3-chlorophenyl)piperazine hydrochloride (0.00075 mole, Aldrich Chemical Company) with the example 4 epoxide (0.0005 mol) and potassium carbonate (1.2 equiv.) under conditions as described for Example 44. Add water to the evaporated reaction solution, and collect and dry the precipitate to afford the title compound (0.11 g, 60%), m.p. 118–120° C., MS (Cl, methane) m/e 470 (MH$^+$).

Analysis: Calculated for $C_{24}H_{24}ClN_3O_3S$: 61.33% C, 5.15% H, 8.94% N; Found: 61.25% C, 5.22% H, 8.76% N.

Example 48

Preparation of (2R)-1-[4-(4-methoxyphenyl)piperazin-1-yl]-3-(3-thieno[2,3-d]isoxazol-3-yl-phenoxy)-propan-2-ol

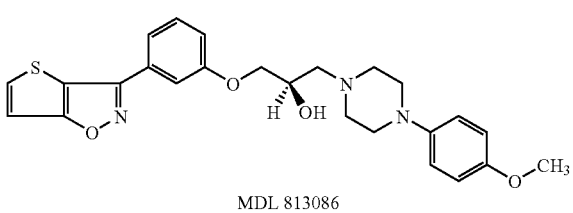

MDL 813086

Condense 1-(4-methoxyphenyl)piperazine dihydrochloride (0.00075 mole, Aldrich Chemical Company) with the example 4 epoxide (0.0005 mol) and potassium carbonate (2.4 equiv.) under conditions as described for Example 44. Add water to the evaporated reaction solution, and collect and dry the precipitate to afford the title compound (0.12 g, 84%), m.p. 110–113° C., MS (Cl, methane) m/e 466 (MH$^+$).

Analysis: Calculated for $C_{25}H_{27}N_3O_4S$: 64.50% C, 5.85% H, 9.03% N; Found: 64.14% C, 5.75% H, 8.95% N.

Example 49

Preparation of (2R)-1-(4-phenylpiperazin-1-yl)-3-(3-thieno[2,3-d]isoxazol-3-yl-phenoxy)propan-2-ol

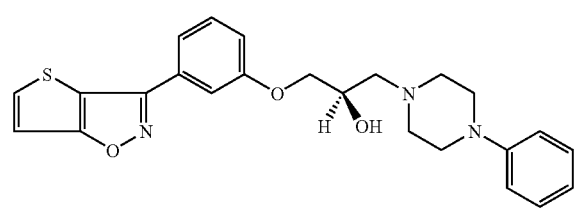

MDL 813087

Condense 1-phenylpiperazine (0.00075 mole, Aldrich Chemical Company) with the example 4 epoxide (0.0005 mol) conditions as described for Example 44. Add water to the evaporated reaction solution, and collect and dry the precipitate to afford the title compound (0.13 g, 84%), m.p. 127–129° C., MS (Cl, methane) m/e 436 (MH$^+$).

Analysis: Calculated for $C_{24}H_{25}N_3O_3S$: 66.18% C, 5.79% H, 9.65% N; Found: 65.96% C, 5.69% H, 9.61% N.

Example 50

Preparation of 2-{4-[(R)-2-hydroxy-3-(3-thieno[2,3-d]isoxazol-3-yl-phenoxy)-propyl]piperazin-1-yl}benzonitrile

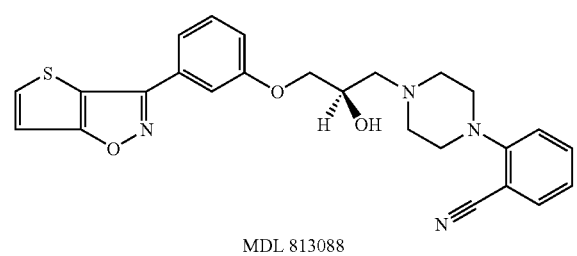

MDL 813088

Condense 2-aminobenzonitrile (0.00075 mole, Aldrich Chemical Company) with the example 4 epoxide (0.0005 mol) under conditions as described for Example 44 to afford the title compound (0.09 g, 81%), m.p. 87–89° C., MS (Cl, methane) m/e 461 (MH$^+$).

Analysis: Calculated for $C_{25}H_{24}N_4O_3S$: 65.20% C, 5.25% H, 12.16% N; Found: 64.81% C, 5.18% H, 11.99% N.

Example 51

Preparation of (2R)-1-(4-benzo[1,3]dioxol-5-ylm-ethyl-piperazin-1-yl)-3-(3-thieno[2,3-d]isoxazol-3-yl-phenoxy)propan-2-ol

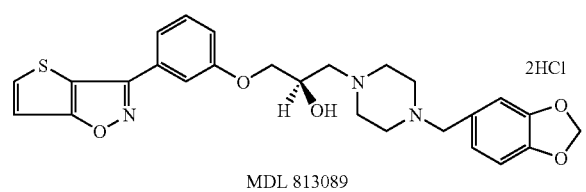

MDL 813089

Condense piperonylpiperazine (0.00075 mole, Aldrich Chemical Company) with the example 4 epoxide (0.0005 mol) under conditions as described for Example 44. Purify the crude product by chromatography on silica gel (Biotage cartridge, elute sequentially with heptane:ethyl acetate (1:3), ethyl acetate, ethyl acetate:2% methanol, ethyl acetate:5% methanol, ethyl acetate:10% methanol), concentrate the desired fractions, and convert the residue to the dihydrochloride salt by methods well known in the art to afford the title compound (0.07 g, 35%), m.p. 225–227° C., MS (CI, methane) m/e 494 (MH+).

Analysis: Calculated for $C_{26}H_{27}N_3O_5S \cdot 2HCl$: 55.13% C, 5.16% H, 7.42% N; Found: 54.95% C, 5.06% H, 7.27% N.

Example 52

Preparation of (2R)-1-(3-thieno[2,3-d]isoxazol-3-yl-phenoxy)-3-[4-(2-trifluoromethylphenyl)-piperazin-1-yl]propan-2-ol

MDL 813090

Condense 1-(2-trifluoromethylphenyl)piperazine (0.00075 mole, J. Med. Chem. 1997, 40, 2674–2687) with the example 4 epoxide (0.0005 mol) under conditions as described for Example 44 to afford the title compound (0.13 g, 71%), m.p. 77–79° C., MS (CI, methane) m/e 504 (MH+).

Analysis: Calculated for $C_{25}H_{24}ClF_3N_3O_3S$: 59.63% C, 4.80% H, 8.34% N; Found: 59.38% C, 4.90% H, 8.23% N.

Example 53

Step J, Scheme II

Preparation of (2R)-1-(6,7-dihydro-4H-thieno[3,2-c]pyridin-5-yl)-3-(3-thieno[2,3-d]isoxazol-3-yl-phenoxy)propan-2-ol L-tartrate

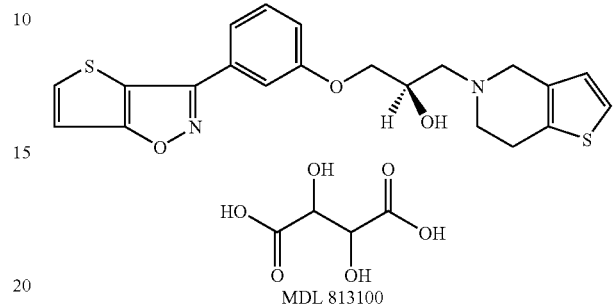

MDL 813100

Treat a stirred solution of 2-thiopheneethylamine (10 g, 0.0786 mol, Aldrich Chemical Company) and water (20 mL) with 37% aqueous formaldehyde solution (6.8 mL). Heat the mixture to 90° C. for 5 hours, cool to room temperature and then stir for 12 hours. Add water (200 mL) and extract twice with ethyl acetate (200 mL portions). Dry the combined organic extracts ($MgSO_4$), filter and concentrate in vacuo. Treat the residue with 5–6N isopropanol/HCl (100 mL) and stir for 5 hours at 60° C., cool to 0° C. and collect the precipitate to afford 4,5,6,7-tetrahydrothieno[3,2-c]pyridine hydrochloride (5.0 g).

Stir a solution of the example 4 epoxide (0.79 g, 0.0029 mol), 4,5,6,7-tetrahydro-thieno[3,2-c]pyridine free base (0.40 g, 0.0029 mol), lithium tetrafluoroborate (0.27 g, 0.0029 mol) and acetonitrile (50 mL) overnight at room temperature. Pour into water (300 mL) and extract with ethyl acetate. Dry ($Na_2SO_4$), filter and concentrate the organic phase, and purify the residue by flash chromatography (silica gel, elute with 3% methanol in dichloromethane) to afford a yellow oil. Dissolve the oil in ethanol, treat with L-tartaric acid (1 molar equivalent), heat to afford a solution, and cool and collect the title compound (0.34 g, 21%) as crystals, m.p. 81–83° C.

Analysis: Calculated for $C_{21}H_{20}N_2O_3S_2 \cdot C_4H_6O_6$ 53.37% C, 4.66% H, 4.98% N; Found: 53.84% C, 5.15% H, 4.85% N.

Example 54

Step K, Scheme II

Preparation of (2R)-benzyl-[2-methoxy-3-(3-thieno[2,3-d]isoxazol-3-yl-phenoxy)propyl]-methylamine hydrochloride

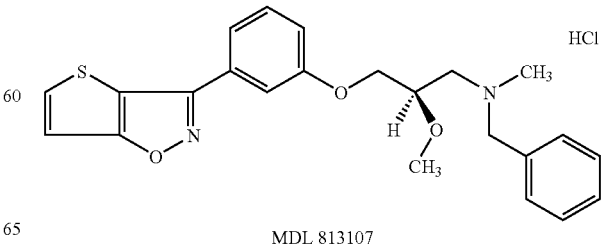

MDL 813107

Prepare the example 4 epoxide from 3-thieno[2,3-d]isoxazol-3-yl-phenol (0.05 mol), potassium t-butoxide (0.05 mol) and (2R)-(−)-glycidyl 3-nitrobenzenesulfonate (0.05 mol) in N-methylpyrrolidinone (250 mL). Treat the resultant epoxide with benzylamine (16.4 mL, 0.15 mol) and heat the reaction mixture at 65° C. for 12 hours. Cool the mixture to 23° C., pour into water (1200 mL) and extract with ethyl acetate (1×750 mL, 2×500 mL). Wash the combined extracts with 5% sodium chloride solution (3×500 mL) and concentrate in vacuo. Purify the crude product by elution through silica gel with ethyl acetate to give the 2(R)-1-benzylamino-3-[3-(thieno[2,3-d]isoxazol-3-yl)phenoxy]-2-propanol (15.0 g, 79%), which is 99.6% pure by HPLC [Waters microbondapak C-18 column, acetonitrile:0.1 N ammonium formate (60:40), flow rate 1 mL/min, UV detection at 240 nm, m.p. 179–181° C., chiral HPLC purity >98% ee.

Treat a chilled (−20° C.) solution of (2R)-1-benzylamino-3-[3-(thieno[2,3-d]isoxazol-3-yl)phenoxy]-2-propanol (1.5 g, 0.004 mol) and dry tetrahydrofuran (30 mL) with potassium bis(trimethylsilyl)amide (1.8 g, 0.00088 mol) under nitrogen. After 0.5 hour, treat with dimethyl sulfate (1.06 g, 0.00084 mol), keep at −20° C. for 1 hour and then allow to warm to room temperature for 2 hours. Quench by addition of saturated potassium carbonate solution (7.5 mL), extract with ethyl acetate (2×50 mL) and concentrate the combined extracts in vacuo. Purify the crude product on silica gel eluting with ethyl acetate:heptane (50:50 v/v) to give the title compound (1.2 g). Form the hydrochloride salt by dissolving the free base in ethyl acetate (10 mL) and treating with 37% hydrochloric acid. Crystallization from ethyl acetate at 0° C. followed by drying at 85° C. for 8 hours gave the title compound, m.p. 155–157° C., chiral HPLC purity >98% ee.

Analysis: Calculated for $C_{23}H_{24}N_2O_3S.HCl$ 62.08% C, 5.66% H, 6.30% N; Found: 61.79% C, 5.51% H, 6.15% N.

Example 55

Step K, Scheme II

Preparation of (2R)-benzyl-[2-methoxy-3-(3-thieno[2,3-d]isoxazol-3-yl-phenoxy)propyl]-amine hydrochloride 0.25 hydrate

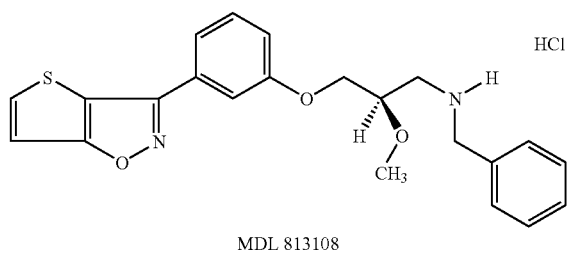

MDL 813108

Treat a chilled (−20° C.) solution of (2R)-1-benzylamino-3-[3-thieno[2,3-d]isoxazol-3-yl)phenoxy]-2-propanol (1.52 g, 0.004 mol, prepared as described in example 54) and dry tetrahydrofuran (30 mL) with potassium bis(trimethylsilyl) amide (0.88 g, 0.0044 mol), age for 0.5 hour and then treat with dimethyl sulfate (0.53 g, 0.0042 mol). Keep the mixture at −20° C. for one hour, allow to warm to 23° C. for 2 hours, quench with water (75 mL) and extract with ethyl acetate (50 mL, then 2×20 mL). Wash the combined organic phase with saturated sodium chloride solution, dry ($K_2CO_3$), filter and concentrate in vacuo. Purify by elution through silica gel (80 g) with ethyl acetate:heptane (50:50) and concentrate the desired fractions to afford the free base of the title compound. Acidify a solution of the free base in ethanol (5 mL) with conc. HCl and crystallize the material from ethyl acetate at −10° C. to give the title compound (0.50 g, 66%), m.p. 85–87° C., MS (Cl, methane) m/e 395 (MH⁺). Karl Fisher titration indicates the presence of 0.9% water.

Analysis: Calculated for $C_{22}H_{22}N_2O_3S.HCl.0.25H_2O$ 60.68% C, 5.44% H, 6.43% N; Found 60.55% C, 5.46% H, 6.35% N.

Example 56

Step J, Scheme II

Preparation of (±)-1-(3,4-dihydro-1H-isoquinolin-2-yl)-3-[3-(thieno[2,3-d]isoxazol-3-yl)phenoxy]-2-propanol hydrochloride

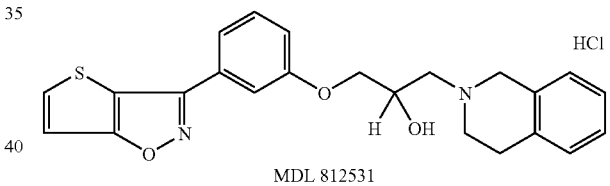

MDL 812531

Treat a solution of (±)-3-(3-epoxymethoxyphenyl)thieno[2,3-d]isoxazole (1.0 G, 0.0037 mol; U.S. Pat. No. 4,728,651, example 25) and acetonitrile (10 mL) with a 1M solution of lithium tetrafluoroborate in acetonitrile (3.66 mL, 0.00366 mol) at 0° C. Add 1,2,3,4-tetrahydroisoquinoline (0.53 g, 0.004 mol, Aldrich Chemical Company) dropwise and stir overnight at room temperature. Quench with water and extract with ethyl acetate. Wash the combined organic extracts with water and brine, dry ($MgSO_4$), filter and concentrate to an oil. Purify the oil by radially accelerated preparative thin layer chromatography, hereinafter "RAPTLC", (Chromatotron, 6 mm plate, elute with ethyl acetate) to provide the free base of the title compound as a solid (0.88 g, 59% yield). Treat a solution of the free base and isopropanol with ethanolic HCl whereupon the title compound crystallizes, and is collected and dried to afford the title compound (0.76 g), m.p. 200–202° C. (dec.), MS (Cl, methane) m/e 407 (MH⁺), thin layer chromatography (silica gel): $R_f$=0.40 (ethyl acetate).

Analysis: Calculated for $C_{23}H_{23}N_2O_3S.HCl$ 62.36% C, 5.23% H, 6.32% N; Found 62.22% C, 5.21% H, 6.28% N.

Example 57

Step J, Scheme II

Preparation of (2R)-1-(3-thieno[2,3-d]isoxazol-3-yl-phenoxy)-3-[(thiophen-2-ylmethyl)amino]propan-2-ol L-tartrate

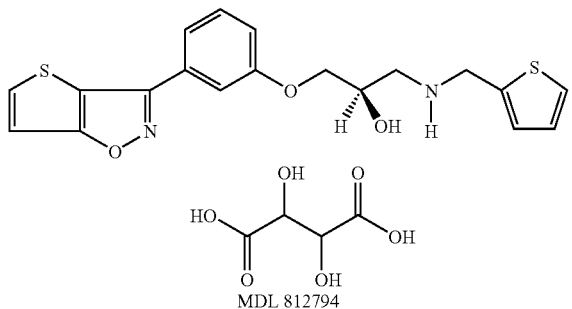

MDL 812794

Prepare as described for Example 53 starting with 0.00915 mole each of the example 4 epoxide and 2-thiophenemethylamine (Acros). Purify the crude product by flash chromatography (silica gel, gradient elution with 3–7% methanol in dichloromethane) and convert to the L-tartrate salt to give the title compound (1.3 g, 52% yield), m.p. 189–192° C.; $[\alpha]_D^{20}=+5.38°$ (c=0.130, methanol); chiral HPLC free base (>99% ee, Chiracel OJ column, 70% hexanes/30% (0.5% Et$_2$NH/ethanol), 0.75 mL/min., detector 237 nm, retention time 36.375 min.); MS (Cl, methane) m/e 387 (MH$^+$)

Analysis: Calculated for $C_{19}H_{18}N_2O_3S \cdot C_4H_6O_6$ 51.48% C, 4.51% H, 5.22% N; Found: 51.62% C, 4.50% H, 5.07% N.

Example 58

Steps F and J, Scheme II

Preparation of (2R)-1-[4-(4-chlorophenyl)piperazin-1-yl]-3-(3-thieno[2,3-d]isoxazol-3-yl-phenoxy)propan-2-ol hydrochloride

MDL 812827

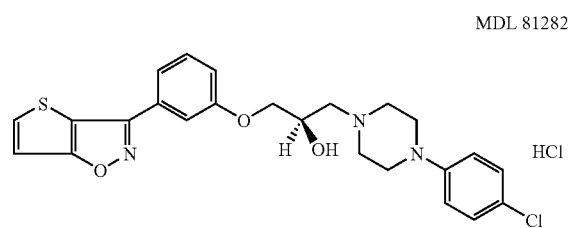

Treat a stirred solution of the example 1 phenol (2.17 g, 0.010 mol) and N-methyl pyrrolidinone (30 mL) at 10° C. with solid potassium t-butoxide (1.12 g, 0.010 mol). Cool the reaction after 30 min. to 0–5° C. and treat with (2R)-(−)-glycidyl 3-nitrobenzenesulfonate (2.59 g, 0.010 mol, 99% ee, Aldrich Chemical Company). Monitor reaction progress by HPLC (Waters μ-Bondapak C-18 column, 0.1 N ammonium formate/acetonitrile (40:60); flow rate 1 mL/min., UV detection at 240 nm). After 2 hours, add 0.1 equivalent of both potassium t-butoxide and the glycidyl nitrobenzenesulfonate and stir for one hour. HPLC indicated >98% conversion to the intermediate epoxide. Add 1-(4-chlorophenyl)-piperazine (5.93 g, 0.030 mol) and water (3 mL) and heat to 70° C. HPLC analysis indicates >98% conversion of the epoxide to product after 5 hours. Cool to 23° C., pour into water (250 mL) and extract with ethyl acetate (150 mL, then 2×100 mL). Wash the combined extracts with 5% NaCl solution, concentrate in vacuo and purify the crude material by chromatography (silica gel, elute with ethyl acetate). Recrystallize the purified material from ethyl acetate:heptane (50:50) to give the free base of the title compound. Treat a slurry of the free base in methanol (25 mL) at 23° C. with 37% HCl (0.67 mL, 1.05 equiv.) to give the title compound (3.62 g, 76% yield) after drying (90° C., 6 hours), m.p. 163–165° C., chiral HPLC purity >98% ee; MS (Cl, methane) m/e 470 (MH$^+$)

Analysis: Calculated for $C_{24}H_{24}ClN_3O_3S \cdot HCl$ 56.92% C, 4.98% H, 8.30% N; Found: 56.74% C, 4.74% H, 8.20% N.

Example 59

Steps F and J, Scheme II

Preparation of (2R)-1-(3-thieno[2,3-d]isoxazol-3-yl-phenoxy)-3-[(thiophen-3-ylmethyl)amino]propan-2-ol hydrochloride

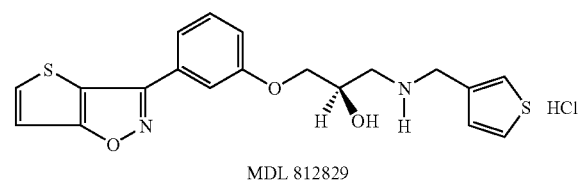

MDL 812829

Prepare as described in example 58 using 3-(aminomethyl)thiophene and heat at 75° C. Chromatograph to give the free base and recrystallize from n-butyl acetate to give 2.36 g of material. Convert to the hydrochloride salt by treating a solution of the free base in absolute ethanol with 37% HCL, cool to 0° C., and collect and dry the separated material to give the title compound (1.55 g, 69% yield), m.p. 139–141° C., chiral HPLC purity >99.1% ee, MS (Cl, methane) m/e 387 (MH$^+$).

Analysis: Calculated for $C_{19}H_{18}N_2O_3S \cdot HCl$ 53.96% C, 4.53% H, 6.62% N; Found 53.88% C, 4.46% H, 6.59% N.

Example 60

Steps F and J, Scheme II

Preparation of (2R)-1-[(naphthalen-1-ylmethyl)amino]-3-(3-thieno[2,3-d]isoxazol-3-yl-phenoxy)propan-2-ol hydrochloride

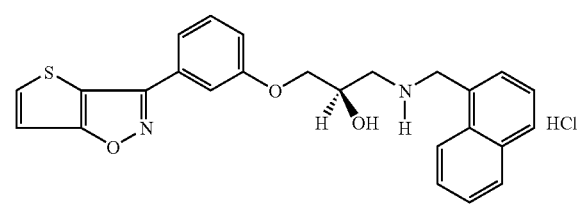

Prepare as described in example 58 using 1-naphthalenemethylamine (Aldrich Chemical Company) and heat at 65°

C. for 16 hours. Chromatograph to give the free base and recrystallize from ethyl acetate to give 3.0 g of material. Convert to the hydrochloride salt by treating a slurry of the free base in absolute ethanol with 37% HCL, and collect and dry the separated material to give the title compound (2.20 g, 73% yield), m.p. 176–177° C., chiral HPLC purity 98% ee, MS (Cl, methane) m/e 431 (MH$^+$).

Analysis: Calculated for $C_{25}H_{22}N_2O_3S\cdot HCl$ 64.30% C, 4.96% H, 6.00% N; Found: 64.00% C, 4.82% H, 5.86% N.

Examples 61–65

Step J, Scheme II

Examples 61–65 were prepared on the same scale using the techniques of parallel synthesis as were examples 23–26. Experimental conditions are described in detail for Example 23, with any variations in procedures being noted for Examples 61–65.

Example 61

Preparation of (2R)-1-(1,2,3,4-tetrahydroisoquinol-2-yl)-3-[4-(thieno[2,3-d]isoxazol-3-yl)phenoxy]-2-propanol

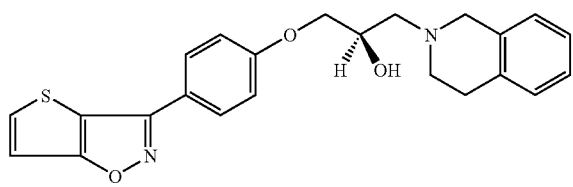

MDL 813152

Condense 1,2,3,4-tetrahydroisoquinoline (0.000823 mole, Aldrich Chemical Company) with the example 5 epoxide (0.000549 mol) under conditions as described for Example 23. Purify the product by flash chromatography (Biotage 40 g silica gel cartridge, step gradient elution with 1%, 3% and 6% methanol in dichloromethane and then with 90:9:1 dichloromethane:methanol:ammonium hydroxide) to afford the title compound (0.17 g), LC/MS (APCI, condition 6) m/e 407 (MH$^+$), retention time 1.73 min.

Example 62

Preparation of (2R)-1-[4-(2-methoxyphenyl)piperazin-1-yl]-3-(4-thieno[2,3-d]isoxazol-3-yl-phenoxy)propan-2-ol

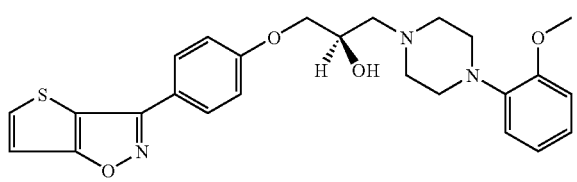

MDL 813153

Condense 1-(2-methoxyphenyl)piperazine (0.000823 mole, Aldrich Chemical Company) with the example 5 epoxide (0.000549 mol) under conditions as described for Example 23. Purify the product by flash chromatography as described for example 61 to afford the title compound (0.17 g), LC/MS (APCI, condition 6) m/e 466 (MH$^+$), retention time 1.87 min.

Example 63

Preparation of (2R)-1-(6,7-dihydro-4H-thieno[3,2-c]pyridin-5-yl)-3-(4-thieno[2,3-d]isoxazol-3-yl-phenoxy)propan-2-ol

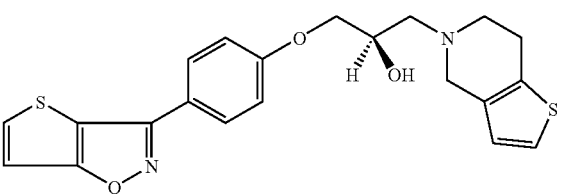

MDL 813154

Condense 4,5,6,7-tetrahydrothieno[3,2-c]pyridine hydrochloride (0.00823 mol, example 53 starting material) with the example 5 epoxide (0.000549 mol) and triethylamine (slight excess) under conditions as described for Example 23. Purify the product by flash chromatography as described for example 61 to afford the title compound (0.057 g), LC/MS (APCI, condition 6) m/e 413 (MH$^+$), retention time 1.52 min.

Example 64

Preparation of 2-{4-[(R)-2-hydroxy-3-(4-thieno[2,3-d]isoxazol-3-yl-phenoxy)propyl]-piperazin-1-yl}benzonitrile

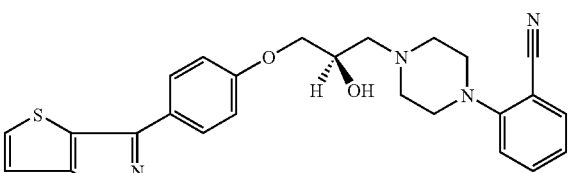

MDL 813157

Condense 2-(1-piperazinyl)benzonitrile (0.000823 mole, Emka-Chemie) with the example 5 epoxide (0.000549 mol) under conditions as described for Example 23. Purify the product by flash chromatography as described for example 61 to afford the title compound (0.19 g), LC/MS (APCI, condition 6) m/e 461 (MH$^+$), retention time 1.95 min.

Example 65

Preparation of (2R)-1-[4-(6-fluorobenzo[d]isoxazol-3-yl)piperidin-1-yl]-3-(4-thieno[2,3-d]isoxazol-3-yl-phenoxy)propan-2-ol

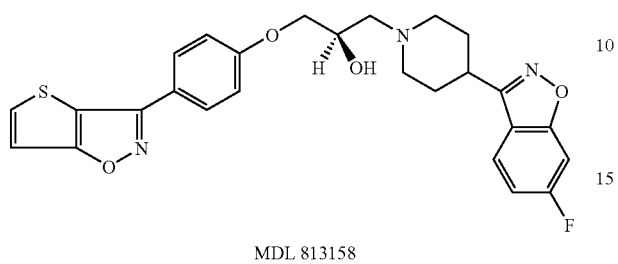

MDL 813158

Condense 4-(6-fluorobenzo[d]isoxzaol-3-yl)piperidine hydrochloride (0.00823 mol, U.S. Pat. No. 4,355,037) with the example 5 epoxide (0.000549 mol) and triethylamine (slight excess) under conditions as described for Example 23. Purify the product by flash chromatography as described for example 61 to afford the title compound (0.22 g), LC/MS (APCI, condition 6) m/e 494 (MH$^+$), retention time 2.30 min.

Example 66

Step J, Scheme II

Preparation of (2S)-(+)-1-benzylamino-2-methyl-3-(3-thieno[2,3-d]isoxazol-3-yl-phenoxy)propan-2-ol maleate

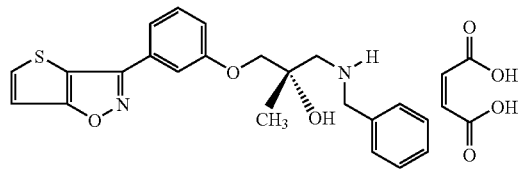

MDL 812723

Treat a solution of (S)-3-[3-(2-methyloxiranylmethoxy) phenyl]thieno[2,3-d]isoxazole (example 7, 0.24 g, 0.00083 mol) and acetonitrile (5 mL) at room temperature with lithium tetrafluoroborate (0.00083 mol) and then add benzylamine (0.00083 mol, Aldrich Chemical Company). Stir overnight and partition between ethyl acetate (100 mL) and water (100 mL). Separate the organic phase, dry (MgSO$_4$), filter and concentrate in vacuo. Purify by flash chromatography (silica gel, elute with 9:1 dichloromethane:methanol) to give the free base of the title compound (0.16 g, 49% yield). Convert the free base to the maleate salt with one equivalent of maleic acid and recrystallize from ethyl acetate to afford the title compound (0.20 g) as white crystals, m.p. 137–138° C., $[\alpha]_D^{20}$=+4.0° (c 0.28, methanol), MS (Cl, methane) m/e 395 (MH$^+$).

Analysis: Calculated for $C_{22}H_{22}N_2O_3S \cdot C_4H_4O_4$ 61.16% C, 5.13% H, 5.49% N; Found 60.75% C, 4.88% H, 5.36% N.

Example 67

Step J, Scheme II

Preparation of (2R)-(−)-1-benzylamino-2-methyl-3-(3-thieno[2,3-d]isoxazol-3-yl-phenoxy)propan-2-ol maleate

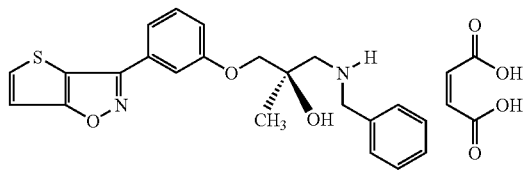

MDL 812725

Prepare as described for example 66 from (R)-3-[3-(2-methyloxiranylmethoxy)-phenyl]thieno[2,3-d]isoxazole (example 6, 0.00105 mol) and benzylamine (0.00105 mol, Aldrich Chemical Company) to give the title compound (0.25 g, 47% yield), m.p. 137–138° C., $[\alpha]_D^{20}$=−4.0° (c 0.28, methanol), MS (Cl, methane) m/e 395 (MH$^+$).

Analysis: Calculated for $C_{22}H_{22}N_2O_3S \cdot C_4H_4O_4$ 61.16% C, 5.13% H, 5.49% N; Found 60.99% C, 5.05% H, 5.35% N.

Example 68

Step J, Scheme II

Preparation of (2R)-1-(benzylmethylamino)-2-methyl-3-(3-thieno[2,3-d]isoxazol-3-yl-phenoxy)propan-2-ol hydrochloride

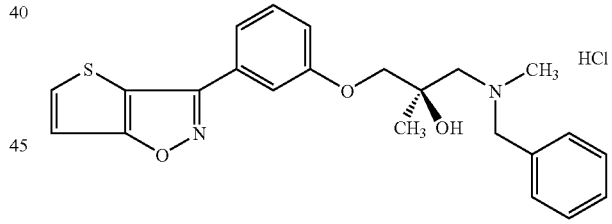

MDL 812883

Prepare as described for example 66 from (R)-3-[3-(2-methyloxiranylmethoxy)-phenyl]thieno[2,3-d]isoxazole (example 6, 0.00105 mol) and benzylmethylamine (0.00105 mol, Aldrich Chemical Company) to give the title compound (0.20 g, 56% yield), m.p. 172–173° C., MS (Cl, methane) m/e 409 (MH$^+$).

Analysis: Calculated for $C_{23}H_{24}N_2O_3S \cdot HCl$ 62.08% C, 5.66% H, 6.30% N; Found 61.88% C, 5.59% H, 6.25% N.

Examples 69–90

Step J, Scheme II

Examples 69–90 were prepared on the same scale using the techniques of parallel synthesis. Experimental conditions are described in detail for Example 69, with any variations in procedures being noted for Examples 70–90.

Example 69

Preparation of (2S)-1-(4-fluorobenzylamino)-2-methyl-3-(3-thieno[2,3-d]isoxazol-3-yl-phenoxy)propan-2-ol

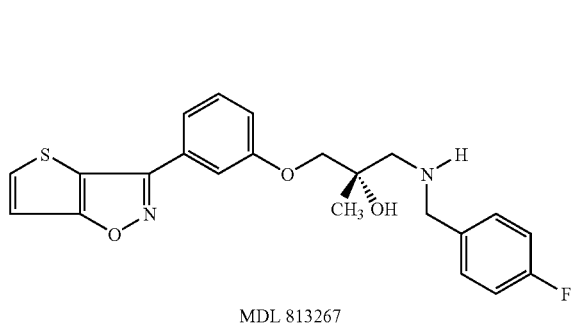

MDL 813267

Add a solution of 4-fluorobenzylamine (Aldrich Chemical Company) in ethanol (3 mL, 0.2774 M, 1.77 equivalents) to a reaction tube. Add ethanol (3 mL) to the reaction tube and then add a solution of (S)-3-[3-(2-methyloxiranylmethoxy)phenyl]thieno[2,3-d]isoxazole (example 7, 1.38 mL, 0.337 M) and dichloroethane. Shake the reaction mixture under argon at reflux temperature overnight in a Bohdan apparatus. Cool and concentrate to remove the solvent. Purify the residue by flash chromatography (silica gel) eluting in step gradient fashion sequentially with 1%, 3%, 6%, and 10% methanol in dichloromethane. Combine and concentrate the desired fractions to give the title compound (0.18 g), LC/MS (APCI, condition 6) m/e 413 (MH+), retention time 2.23 min. Preparation of a larger sample and conversion to the hydrochloride salt is described as example 102.

Example 70

Preparation of (2S)-1-(2-fluorobenzylamino)-2-methyl-3-(3-thieno[2,3-d]isoxazol-3-yl-phenoxy)propan-2-ol

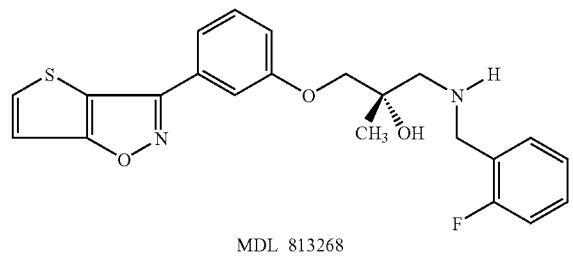

MDL 813268

Prepare as described for example 69 from 2-fluorobenzylamine (Aldrich Chemical Company) to give the title compound (0.067 g), LC/MS (APCI) m/e 413 (MH+), retention time 2.08 min.

Example 71

Preparation of (2S)-1-(3-fluorobenzylamino)-2-methyl-3-(3-thieno[2,3-d]isoxazol-3-yl-phenoxy)propan-2-ol

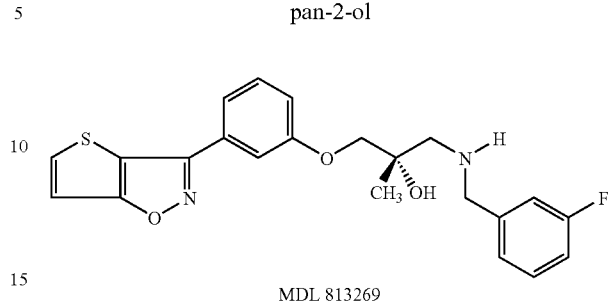

MDL 813269

Prepare as described for example 69 from 3-fluorobenzylamine (Aldrich Chemical Company) to give the title compound (0.0.0425 g), LC/MS (APCI, condition 6) m/e 413 (MH+), retention time 2.12 min.

Example 72

Preparation of (2S)-1-(4-chlorobenzylamino)-2-methyl-3-(3-thieno[2,3-d]isoxazol-3-yl-phenoxy)propan-2-ol

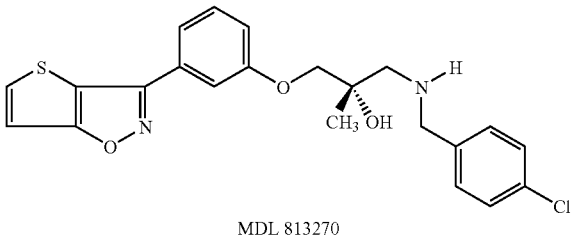

MDL 813270

Prepare as described for example 69 from 4-chorobenzylamine (Aldrich Chemical Company) to give the title compound (0.0924 g), LC/MS (APCI, condition 6) m/e 429 (MH+), retention time 2.33 min.

Example 73

Preparation of (2S)-1-(2-chlorobenzylamino)-2-methyl-3-(3-thieno[2,3-d]isoxazol-3-yl-phenoxy)propan-2-ol

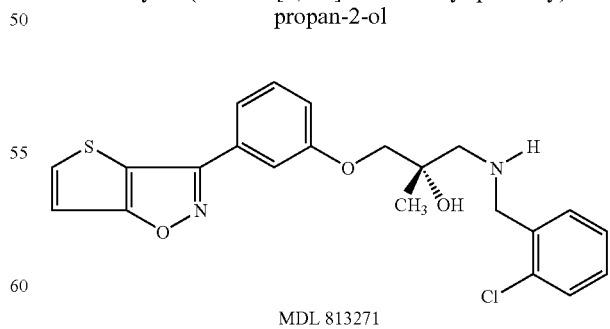

MDL 813271

Prepare as described for example 69 from 2-chorobenzylamine (Aldrich Chemical Company) to give the title compound (0.0522 g), LC/MS (APCI, condition 6) m/e 429 (MH+), retention time 2.23 min.

Example 74

Preparation of (2S)-1-(3,4-dichlorobenzylamino)-2-methyl-3-(3-thieno[2,3-d]isoxazol-3-yl-phenoxy)propan-2-ol

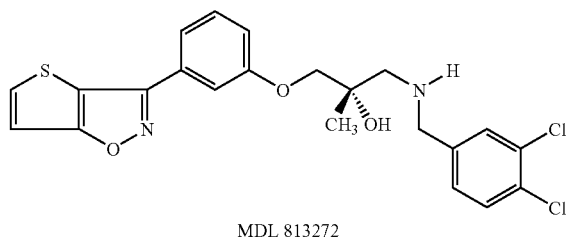

MDL 813272

Prepare as described for example 69 from 3,4-dichorobenzylamine (Aldrich Chemical Company) to give the title compound (0.0596 g), LC/MS (APCI, condition 6) m/e 463 (MH$^+$), retention time 2.48 min.

Example 75

Preparation of (2S)-2-methyl-1-[1 (R)-phenylethylamino]-3-(3-thieno[2,3-d]isoxazol]-3-yl-phenoxy)-propan-2-ol

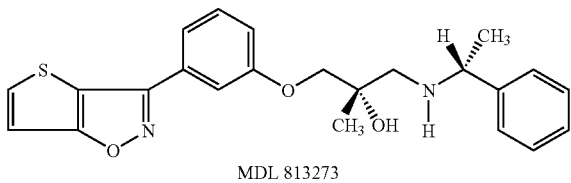

MDL 813273

Prepare as described for example 69 from (R)-(+)-α-methylbenzylamine (Aldrich Chemical Company) to give the title compound (0.113 g), LC/MS (APCI, condition 6) m/e 409 (MH$^+$), retention time 2.18 min.

Example 76

Preparation of (2S)-2-methyl-1-[1(S)-phenylethylamino]-3-(3-thieno[2,3-d]isoxazol]-3-yl-phenoxy)-propan-2-ol

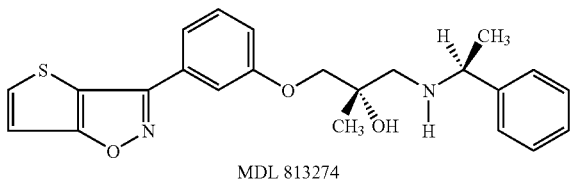

MDL 813274

Prepare as described for example 69 from (S)-(−)-α-methylbenzylamine (Aldrich Chemical Company) to give the title compound (0.174 g), LC/MS (APCI, condition 6) m/e 409 (MH$^+$), retention time 2.22 min.

Example 77

Preparation of (2S)-2-methyl-1-[(naphthalen-1-ylmethyl)amino]-3-(3-thieno[2,3-d]isoxazol-3-yl-phenoxy)propan-2-ol

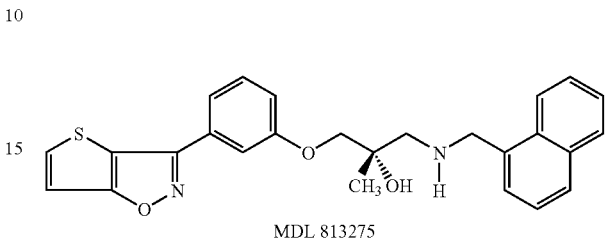

MDL 813275

Prepare as described for example 69 from 1-naphthalenemethylamine (Aldrich Chemical Company) to give the title compound (0.0248 g), LC/MS (APCI, condition 6) m/e 445 (MH$^+$), retention time 2.43 min.

Example 78

Preparation of (2S)-2-methyl-1-(4-methylbenzylamino)-3-(3-thieno[2,3-d]isoxazol-3-yl-phenoxy)propan-2-ol

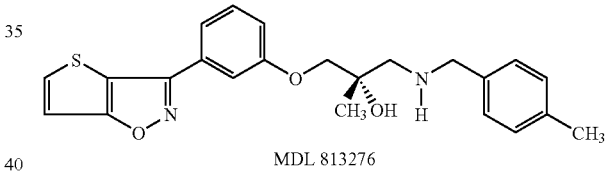

MDL 813276

Prepare as described for example 69 from 4-methylbenzylamine (Aldrich Chemical Company) to give the title compound (0.124 g), LC/MS (APCI, condition 6) m/e 409 (MH$^+$), retention time 2.33 min.

Example 79

Preparation of (2S)-1-(4-methoxybenzylamino)-2-methyl-3-(3-thieno[2,3-d]isoxazol-3-yl-phenoxy)propan-2-ol

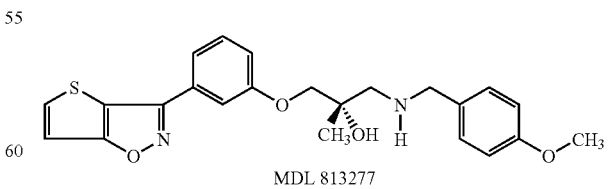

MDL 813277

Prepare as described for example 69 from 4-methoxybenzylamine (Aldrich Chemical Company) to give the title compound (0.122 g), LC/MS (APCI, condition 6) m/e 425 (MH$^+$), retention time 2.10 min.

Example 80

Preparation of (2S)-1-(2-methoxybenzylamino)-2-methyl-3-(3-thieno[2,3-d]isoxazol-3-yl-phenoxy)propan-2-ol

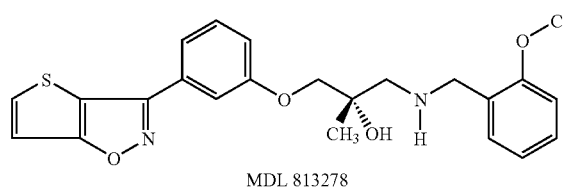

MDL 813278

Prepare as described for example 69 from 2-methoxybenzylamine (Aldrich Chemical Company) to give the title compound (0.083 g), LC/MS (APCI, condition 6) m/e 425 (MH$^+$), retention time 2.23 min.

Example 81

Preparation of (2S)-1-[(furan-2-ylmethyl)amino]-2-methyl-3-(3-thieno[2,3-d]isoxazol-3-yl-phenoxy)propan-2-ol

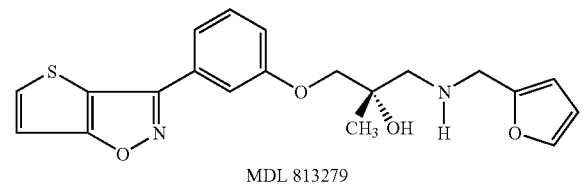

MDL 813279

Prepare as described for example 69 from furfurylamine (Aldrich Chemical Company) to give the title compound (0.1098 g), LC/MS (APCI, condition 6) m/e 385 (MH$^+$), retention time 1.36 min.

Example 82

Preparation of (2S)-1-(2-thienylmethylamino)-2-methyl-3-[3-thieno[2,3-d]isoxazol-3-yl-phenoxy]propan-2-ol

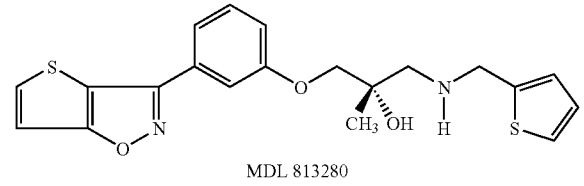

MDL 813280

Prepare as described for example 69 from 2-aminomethylthiophene (Acros) to give the title compound (0.1153 g), LC/MS (APCI, condition 6) m/e 401 (MH$^+$), retention time 1.68 min.

Example 83

Preparation of (2S)-1-(3-thienylmethylamino)-2-methyl-3-[3-thieno[2,3-d]isoxazol-3-yl-phenoxy]propan-2-ol

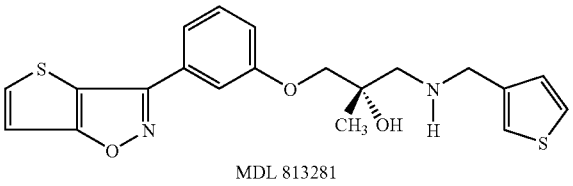

MDL 813281

Prepare as described for example 69 from 3-aminomethylthiophene [M. R. Bryce et al., Synthetic Metals, 1988, 26, 153–168] to give the title compound (0.066 g), LC/MS (APCI, condition 6) m/e 401 (MH$^+$), retention time 1.80 min.

Example 84

Preparation of (2S)-2-methyl-1-[(pyridin-3-ylmethyl)amino]-3-(3-thieno[2,3-d]isoxazol-3-yl-phenoxy)propan-2-ol

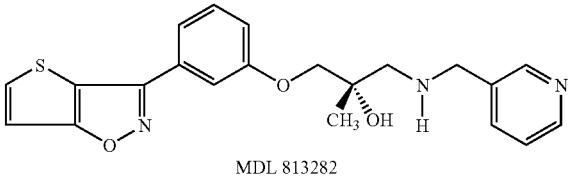

MDL 813282

Prepare as described for example 69 from 3-(aminomethyl)pyridine (Aldrich Chemical Company) to give the title compound (0.066 g), LC/MS (APCI, condition 6) m/e 396 (MH$^+$), retention time 0.62 min.

Example 85

Preparation of (2S)-2-methyl-1-[(pyridin-2-ylmethyl)amino]-3-(3-thieno[2,3-d]isoxazol-3-yl-phenoxy)propan-2-ol

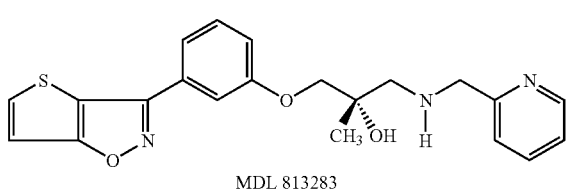

MDL 813283

Prepare as described for example 69 from 2-(aminomethyl)pyridine (Aldrich Chemical Company) to give the title compound (0.116 g), LC/MS (APCI, condition 6) m/e 396 (MH$^+$), retention time 1.28 min.

Example 86

Preparation of (2S)-1-(benzylmethylamino)-2-methyl-3-[3-thieno[2,3-d]isoxazol-3-yl-phenoxy]propan-2-ol

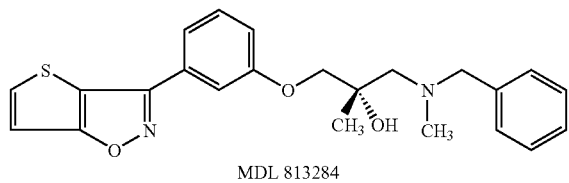

MDL 813284

Prepare as described for example 69 from N-benzylmethylamine (Aldrich Chemical Company) to give the title compound (0.151 g), LC/MS (APCI, condition 6) m/e 409 (MH$^+$), retention time 2.12 min.

Example 87

Preparation of (2S)-1-[4-(2-methoxyphenyl)piperazin-1-yl]-2-methyl-3-[3-thieno[2,3-d]isoxazol-3-yl-phenoxy]propan-2-ol

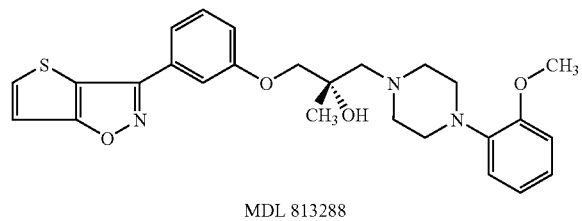

MDL 813288

Prepare as described for example 69 from 1-(2-methoxyphenyl)piperazine (Aldrich Chemical Company; use 2 mL of a 0.2744 M solution in dichloroethane, 1.18 equivalents) to give the title compound (0.027 g), LC/MS (APCI, condition 6) m/e 480 (MH$^+$), retention time 2.33 min.

Example 88

Preparation of (2S)-1-[4-(2-cyanophenyl)-1-piperazinyl]-2-methyl-3-[3-thieno[2,3-d]isoxazol-3-yl-phenoxy]propan-2-ol

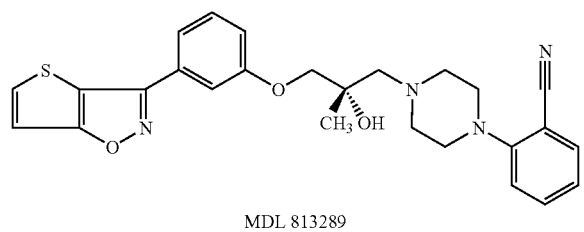

MDL 813289

Prepare as described for example 87 from 1-(2-cyanophenyl)piperazine (Emka-Chemie; use 2 mL of a 0.2744 M solution in dichloroethane, 1.18 equivalents) to give the title compound (0.152 g), LC/MS (APCI, condition 6) m/e 475 (MH$^+$), retention time 2.32 min.

Example 89

Preparation of (2S)-1-[4-(3-chlorophenoxy)-1-piperidinyl]-2-methyl-3-[3-thieno[2,3-d]isoxazol-3-yl-phenoxy]propan-2-ol

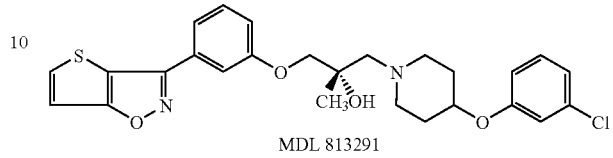

MDL 813291

Prepare as described for example 87 from 4-(3-chlorophenoxy)piperidine (J. Med. Chem., 1978, 21, 309–312) use 2 mL of a 0.2744 M solution in dichloroethane, 1.18 equivalents) to give the title compound (0.074 g), LC/MS (APCI, condition 6) m/e 499 (MH$^+$), retention time 2.68 min.

Example 90

Preparation of (2S)-1-[4-(6-fluorobenzo[d]isoxazol-3-yl)piperidin-1-yl]-2-methyl-3-[3-thieno[2,3-d]isoxazol-3-yl-phenoxy]propan-2-ol

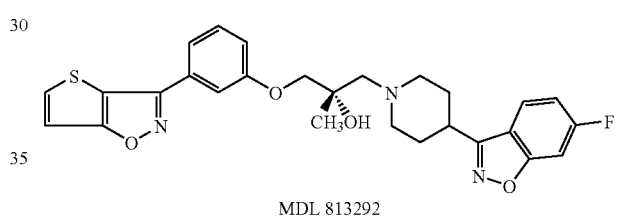

MDL 813292

Prepare as described for example 87 from 4-(6-fluorobenzo[d]isoxzaol-3-yl)piperidine use 2 mL of a 0.2744 M solution in dichloroethane, 1.18 equivalents, U.S. Pat. No. 4,355,037) to give the title compound (0.186 g), LC/MS (APCI, condition 6) m/e 508 (MH$^+$), retention time 2.50 min.

Example 91

Step J, Scheme II

Preparation of (2R)-1-[(1H-benzimidazol-2-ylmethyl)amino]-3-[3-thieno[2,3-d]isoxazol-3-yl-phenoxy]propan-2-ol

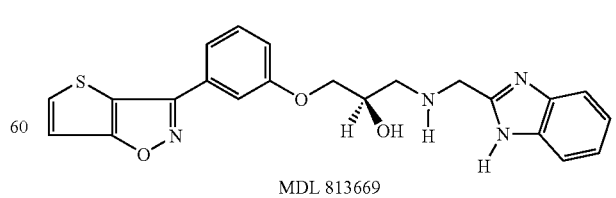

MDL 813669

Heat a mixture of (R)-3-(3-epoxymethoxyphenyl)thieno[2,3-d]isoxazole (example 4, 0.82 g, 0.003 mol), 2-(aminomethyl)benzimidazole dihydrochloride (2.64 g, 0.012 mol, Aldrich Chemical Company), triethylamine (2.5 g, 0.024 mol) and absolute ethanol (25 mL) at reflux for 8.5 hours. Cool and concentrate, and dissolve the brown residue in ethyl acetate (80 mL). Wash with water (2×25 mL) and extract the combined aqueous washings with ethyl acetate (30 mL). Combine and dry (Na$_2$SO$_4$) the ethyl acetate phases, filter and concentrate to afford a dark brown solid. Purify by flash chromatography (10 g silica gel, SepPak cartridge, elute sequentially with 3% and 5% methanol in dichloromethane) and concentrate the desired fractions to afford a reddish brown solid. Further purify this material by flash chromatography (5 g silica gel, SepPak cartridge, elute sequentially with 2% and 3% methanol in dichloromethane) to give the title compound (0.26 g, 21% yield), LC/MS (APCI) m/e 421 (MH$^+$), retention time 4.00 min.

Example 92

Preparation of 3-{(R)-4-[2-hydroxy-3(3-thieno[2,3-d]isoxazol-3-yl)phenoxy]propyl]-piperazin-1-yl}-benzo[d]isoxazol-6-ol

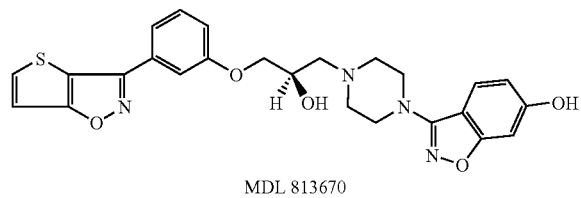

MDL 813670

Prepare 4-(6-methoxybenzo[d]isoxzaol-3-yl)piperazine by slowly adding a solution of hydroxylamine hydrochloride (57.2 g, 0.823 mol) and water (600 mL) to a solution of sodium hydroxide (76.9 g, 1.92 mol) and water (300 mL). Then add a solution of methyl 4-methoxysalicylate (100 g, 0.55 mol, Aldrich Chemical Co.) and ether (800 mL), stir overnight, evaporate the ether, acidify with dilute hydrochloric acid, cool to 0° C., and filter. Recrystallize the filter cake from methanol to afford the 2-hydroxy-p-anisohydroxamic acid (78 g). Treat a warm (50° C.) solution of the hydroxamic acid (78 g) and tetrahydrofuran (500 mL) under nitrogen with a solution of carbonyldiimidazole (138.1 g, 0.85 mol) and tetrahydrofuran (500 mL), reflux for 3.5 hours, quench by addition of water (1000 mL), acidify to pH 3, add water (1000 mL) and refrigerate overnight. Collect the solid, wash with water and recrystallize from methanol to afford 54 g of 3-hydroxy-6-methoxy-1,2-benzisoxazole. Heat a stirred mixture of 3-hydroxy-6-methoxy-1,2-benzisoxazole (54 g) and POCl$_3$ (100.3 g, d 1.645) at 95° C. under nitrogen, cool to 30° C., add triethylamine (33 g), heat at 140° C. overnight, quench with stirring into ice water and filter. Dissolve the filter cake in cyclohexane (2000 mL), filter, concentrate and recrystallize the residue from petroleum ether to give 3-chloro-6-methoxy-1,2-benzisoxzole (33 g). Treat this product with piperazine as described in U.S. Pat. No. 5,852,022, the contents of which are herein incorporated by reference, to afford 6-methoxy-3-(1-piperazinyl)-1,2-benzisoxazole.

Heat a stirred mixture of 6-methoxy-3-(1-piperazinyl)-1,2-benzisoxazole (0.1 mol), and 62% w/w hydrobromic acid (116.5 mL) at 115° C. under nitrogen for 6 hours. Partially concentrate under reduced pressure (15–20 mm Hg) at 50 to 60° C., add water (100 mL) and concentrate again. Repeat this process two times. Treat the residual heterogenous slurry with water (150 mL), age at 5° C. for 0.5 hour, and collect the solid by vacuum filtration. Wash the filter cake twice with cold water and dry to afford 6-hydroxy-3-(1-piperazinyl)-1,2-benzisoxazole hydrobromide (33.7 g). Suspend the crude material in water (830 mL), heat to 95–97° C., treat with activated charcoal (6.64 g), age at 95–97° C. for 0.25 hour, vacuum filter through celite, cool the filtrate to 5° C. and after 0.5 hour collect the product by vacuum filtration. Wash the filter cake twice with cold water and dry at 80° C. in high vacuum for 4 hours to afford 6-hydroxy-3-(1-piperazinyl)-1,2-benzisoxazole hydrobromide (23.5 g, 79%). The material was 99.8% pure by HPLC (Nucleosil C-18 column, 5 micron, 4.6×25 cm; mobile phase: NH$_4$H$_2$PO$_4$ (0.05N):acetonitrile, 55:45 v/v; flow rate 1 mL/min; UV detection at 220/240 nm. MS (EI) 219 (M$^+$)

ANALYSIS: Calculated for C$_{11}$H$_{13}$N$_3$O$_2$.HBr: 44.02% C, 4.70% H, 14.00% N, 26.62% Br; Found 44.01% C, 4.62% H, 14.01% N, 26,44% Br.

Perform the synthesis of the title compound under conditions as described for Example 11 using 6-hydroxy-3-(1-piperazinyl)-1,2-benzisoxazole hydrobromide with potassium carbonate (0.20 g, 0.0015 mol). Filter the precipitate from the cooled reaction mixture, extract the filtrate, combine the precipitate with the organic extract, and continue as described in example 11 to afford the title compound (0.12 g, 30% yield), LC/MS (APCI, condition 4) m/e 493 (MH$^+$).

Examples 93–98

Step J, Scheme II

Examples 93–98 were prepared on the same scale using the techniques of parallel synthesis. Experimental conditions are described in detail for Example 93, with any variations in procedures being noted for Examples 94–98.

Example 93

Preparation of (2R)-1-[(pyridin-4-yl)methylamino]-3-[3-thieno[2,3-d]isoxazol-3-yl-phenoxy)propan-2-ol

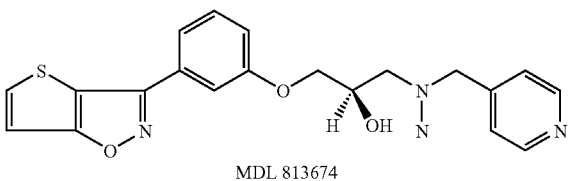

MDL 813674

Add 8 mL of a solution of (R)-3-(3-epoxymethoxyphenyl)thieno[2,3-d]isoxazole (example 4, 0.22 g, 0.0008 mol) in acetonitrile-water (4:1) to a mixture of 4-(aminomethyl)pyridine (0.435 g, 0.0040 mol), and shake and heat at 70° C. for 4 hours. Cool to room temperature and work-up as described for example 11. Purify the crude material using a 5 g silica gel SepPak cartridge eluting sequentially with dichloromethane, and then with 3% and 5% methanol in dichloromethane. Combine the desired fractions, concentrate and further purify the residue a 5 g silica gel SepPak cartridge eluting sequentially with 2%, 3% and 5% methanol in dichloromethane to give the title compound (0.083 g, 27% yield), LC/MS (APCI, condition 4), m/e 382 (MH+), retention time 3.52 min.

Example 94

Preparation of (2R)-1-(1,2,3,4-tetrahydronaphthalen-1-ylamino)-3-[3-thieno[2,3-d]isoxazol-3-yl)phenoxy]propan-2-ol

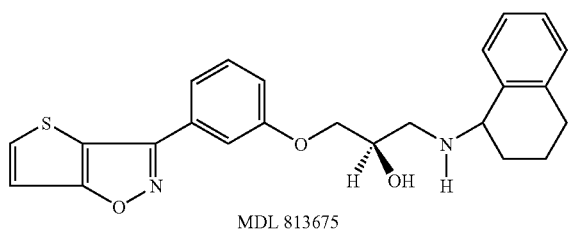

MDL 813675

Prepare as described for example 93 using 1,2,3,4-tetrahydro-1-naphthylamine (0.004 mol, Aldrich Chemical Company). Purify the crude material using a 5 g silica gel SepPak cartridge eluting sequentially with heptane:ethyl acetate 2:3 and then with ethyl acetate. Combine the desired fractions, concentrate and further purify the residue a 5 g silica gel SepPak cartridge eluting sequentially with heptane:ethyl acetate 2:1, heptane:ethyl acetate 1:2 and then with ethyl acetate to give the title compound (0.20 g, 60% yield), LC/MS (APCI, condition 4), m/e 421 (MH+), retention time 4.27 min.

Example 95

Preparation of (2R)-1-(1,2,3,4-tetrahydro-β-carbolin-2-yl)-3-[3-thieno[2,3-d]isoxazol-3-yl)phenoxy]propan-2-ol

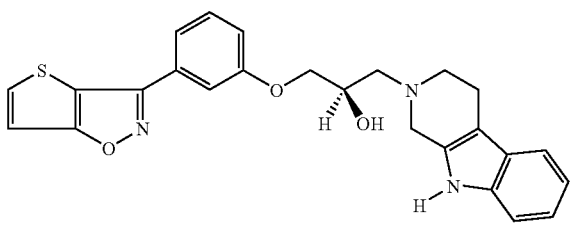

MDL 813676

Prepare as described for example 93 using 1,2,3,4-tetrahydro-β-carboline (0.0012 mol, Aldrich Chemical Company). Collect the precipitate from the chilled reaction mixture and dry in vacuo at 50° C. to afford the title compound (0.276 g, 77% yield), LC/MS (APCI, condition 4), m/e 446 (MH+), retention time 4.28 min.

Example 96

Preparation of (2R)-1-(6,7-dimethoxy-1,2,3,4-tetrahydroisoquinolin-2-yl]-3-[3-(thieno[2,3-d]isoxazol-3-yl)phenoxy]propan-2-ol

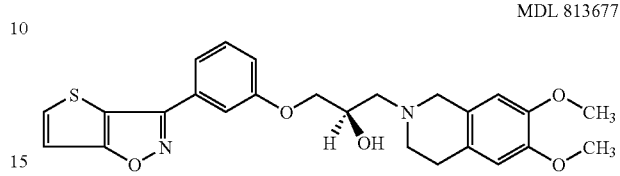

MDL 813677

Prepare as described for example 93 using 6,7-dimethoxy-1,2,3,4-tetrahydroisoquinoline hydrochloride (0.0012 mol, Aldrich Chemical Company). After extraction, reserve the aqueous phase. Concentrate the organic phase and chromatograph the crude material on silica gel eluting sequentially with heptane:ethyl acetate 2:1, heptane:ethyl acetate 1:2, ethyl acetate and then with ethyl acetate:methanol 9:1. Combine the desired fractions and concentrate to afford a residue. Reextract the aqueous phase with dichloromethane:methanol 9:1 and dichloromethane. Combine, dry and concentrate the dichloromethane extracts, and combine the residue with the material recovered by chromatographic purification. Further purify the combined materials on silica gel (5 g) eluting with sequentially with 2% and 5% methanol in dichloromethane. Combine the desired fractions, concentrate and chromatograph the residue on silica gel (5 g) eluting sequentially with heptane:dichloromethane 1:1, dichloromethane, and 2% methanol in dichloromethane to give the title compound (0.046 g, 12% yield), LC/MS (APCI, condition 4), m/e 467 (MH+), retention time 4.05 min.

Example 97

Preparation of (2R)-1-[4-(4-methoxyphenyl)-3-methylpiperazin-1-yl]-3-[3-(thieno[2,3-d]isoxazol-3-yl)phenoxy]propan-2-ol

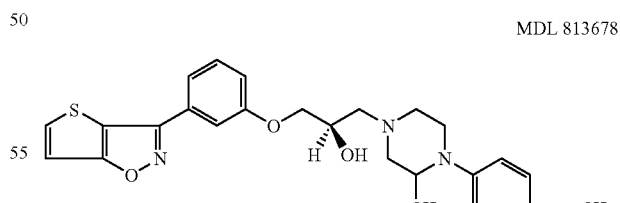

MDL 813678

Prepare as described for example 93 using racemic1-(4-methoxyphenyl)-2-methylpiperazine (0.0012 mol, Acros). Purify the crude material using a 5 g silica gel SepPak cartridge eluting sequentially with heptane:ethyl acetate 2:1 and then with heptane:ethyl acetate 1:1 and ethyl acetate to give the title compound (0.21 g, 55% yield), LC/MS (APCI, condition 4), m/e 480 (MH+), retention time 4.18 min.

Example 98

Preparation of 4-(4-chlorophenyl)-1-{(R)2-hydroxy-3-[3-(thieno[2,3-d]isoxazol-3-yl)phenoxy]propyl}piperidin-4-ol

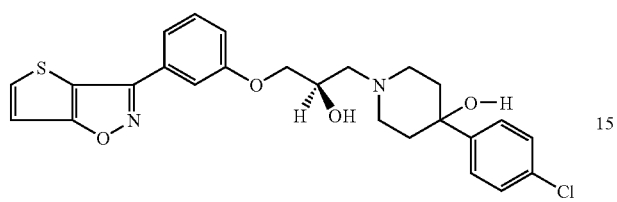

MDL 813679

Prepare as described for example 93 using 4-(4-chlorophenyl)-4-hydroxypiperidine (0.0012 mol, Aldrich Chemical Company). Purify the crude material on silica gel (5 g) eluting sequentially with heptane:ethyl acetate 2:3 and then with ethyl acetate to give the title compound (0.25 g, 64% yield), LC/MS (APCI, condition 4), m/e 485 (MH+), retention time 4.19 min.

Example 99

Step J, Scheme II

Preparation of (2R)-1-(indan-2-ylamino)-3-(3-thieno[2,3-d]isoxazol-3-yl-phenoxy)-propan-2-ol

MDL 814157

Heat and shake a mixture of 2-aminoindan hydrochloride (0.186 g, 0.0011 mol, Aldrich Chemical Company), (R)-3-(3-epoxymethoxyphenyl)thieno[2,3-d]isoxazole (Example 4, 0.15 g, 0.00055 mol), potassium carbonate (0.265 g, 0.00192 mol), and ethanol (6 mL) overnight at 80° C. Concentrate the reaction mixture under a stream of nitrogen. Purify the crude material by taking-up in methanol:ethyl acetate (10:90) and elute through silica gel (10 g SepPak cartridge) to give the title compound (0.139 g, 62%) as a solid, LC/MS (APCI, condition 1), m/e 407 (MH+), retention time 6.58 min.

Dissolve the free base (103 mg) in ethyl acetate:methanol and treat with a solution of ethereal hydrogen chloride until the treated solution reaches approximately pH 1. Stir for 15 minutes, concentrate in vacuo, dissolve the residual oil in methanol, and treat dropwise with ethyl acetate to afford a white precipitate. Collect and dry the precipitate in vacuo to provide 96.6 mg (86%) of the title compound as the hydrochloride salt, LC/MS (APCI, condition 3), m/e 407 (MH+), retention time 5.31 min.

Example 100

Step J, Scheme II

Preparation of (2R)-1-(cyclohexylmethyl-amino)-3-(3-thieno[2,3-d]isoxazol-3-yl-phenoxy)-propan-2-ol

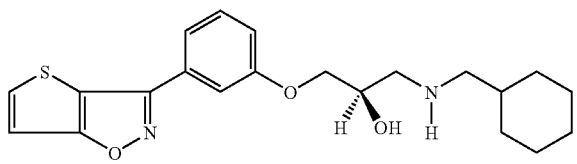

MDL 814160

Prepare as described for example 99 using cyclohexanemethylamine (0.0011 mol, Aldrich Chemical Company) without potassium carbonate. Concentrate the reaction mixture under a stream of nitrogen. Purify the crude material by taking-up in ethyl acetate and elute through silica gel (10 g SepPak cartridge) to give the title compound (0.128 g, 60%) as a solid, LC/MS (APCI, condition 1), m/e 387 (MH+), retention time 6.59 min.

Example 101

Step J, Scheme II

Preparation of (2R)-1-(indan-1-ylamino)-3-(3-thieno[2,3-d]isoxazol-3-yl-phenoxy)-propan-2-ol

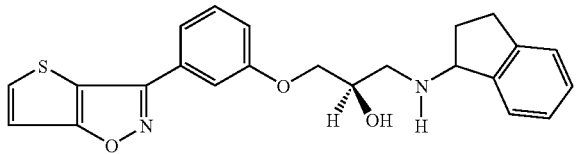

MDL 814161

Prepare as described for example 99 using racemic 1-aminoindan (0.0011 mol, Aldrich Chemical Company) without potassium carbonate. Concentrate the reaction mixture under a stream of nitrogen. Purify the crude material by taking-up in ethyl acetate and elute through silica gel (10 g SepPak cartridge) to give the title compound (0.147 g, 66%) as a solid, LC/MS (APCI, condition 1), m/e 407 (MH+), retention time 6.31 min.

Example 102

Step J, Scheme II

Preparation of (2S)-1-(4-fluorobenzylamino)-2-methyl-3-(3-thieno[2,3-d]isoxazol-3-yl-phenoxy)propan-2-ol hydrochloride

MDL 814196

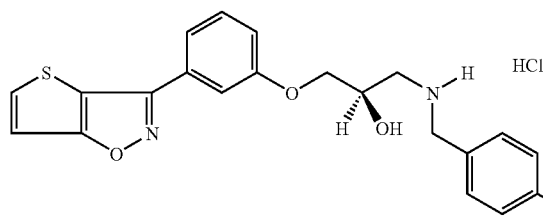

Reflux a solution of the example 7 epoxide (0.80 g, 0.0028 mol), 4-fluorobenzylamine (0.52 g, 0.0042 mol, 1.5 equiv., Aldrich Chemical Company) and absolute ethanol (50 mL) overnight. Concentrate and purify the crude material by flash chromatography on silica gel (gradient elution with 2% to 4% methanol) to give the free base of example 69. Treat a solution of the free base and absolute ethanol with excess ethereal hydrogen chloride, evaporate to dryness, and recrystallize the residue from isopropanol to provide the title compound (0.34 g, 27% yield), m.p. 129–132° C., single peak by chiral HPLC (Chiracel OJ column, elute with heptane:ethanol, 70:30, 0.75 mL/min, monitor at 237 nm).

Analysis: Calculated for $C_{22}H_{21}FN_2O_3S \cdot HCl$ 58.86% C, 4.94% H, 6.24% N; Found 58.44% C, 5.27% H, 5.86% N

Example 103

Step J, Scheme II

Preparation of (2S)-1-(3,4-dichlorobenzylamino)-2-methyl-3-(3-thieno[2,3-d]isoxazol-3-yl-phenoxy)propan-2-ol hydrochloride

MDL 814197

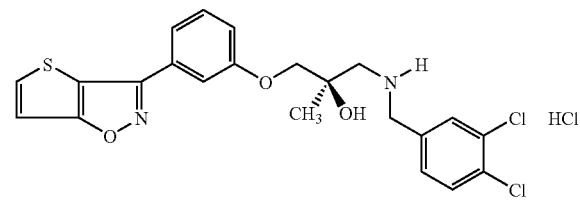

Condense the example 7 epoxide (0.0028 mol) and 3,4-dichorobenzylamine (0.0042 mol, Aldrich Chemical Company), and convert the purified free base (example 74) to the hydrochloride salt as described for example 102 to provide the title compound (0.66 g, 47% yield), m.p. 185–187° C., single peak by chiral HPLC (Chiracel OJ column, elute with heptane:ethanol, 70:30, 0.75 mL/min, monitor at 237 nm).

Analysis: Calculated for $C_{22}H_{20}Cl_2N_2O_3S \cdot HCl$ 52.87% C, 4.23% H, 5.60% N; Found 52.88% C, 4.26% H, 5.53% N

Example 104

Step J, Scheme II

Preparation of (2S)-1-(3,4-difluorobenzylamino)-2-methyl-3-[3-(thieno[2,3-d]isoxazol-3-yl)phenoxy]propan-2-ol hydrochloride

MDL 814198

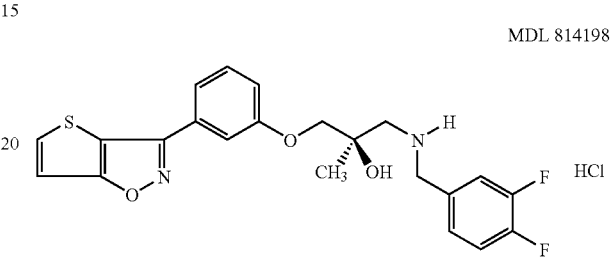

Condense the example 7 epoxide (0.0023 mol) and 3,4-difluorobenzylamine (0.0035 mol, Aldrich Chemical Company), and convert the purified free base to the hydrochloride salt as described for example 102 to provide the title compound (0.44 g, 40% yield), m.p. 177–179° C., single peak by chiral HPLC (Chiracel OJ column, elute with heptane:ethanol, 70:30, 0.75 mL/min, monitor at 237 nm), MS (Cl, methane) m/e 431 (MH$^+$).

Analysis: Calculated for $C_{22}H_{20}FN_2O_3S \cdot HCl$ 56.59% C, 4.53% H, 6.00% N; Found 56.53% C, 4.50% H, 5.95% N

Example 105

Step J, Scheme II

Preparation of (2R)-1-(adamantan-1-ylamino)-3-(3-thieno[2,3-d]isoxazol-3-yl-phenoxy)-propan-2-ol

MDL 814310

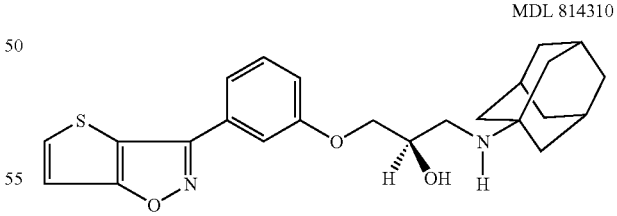

Heat and shake a mixture of 1-adamantanamine (0.166 g, 0.0011 mol, Aldrich Chemical Company), (R)-3-(3-epoxymethoxyphenyl)thieno[2,3-d]isoxazole (example 4, 0.15 g, 0.00055 mol), and ethanol (6 mL) overnight at 80° C. Concentrate the reaction mixture under a stream of nitrogen. Purify the crude material by taking-up in ethyl acetate and elute through silica gel (10 g SepPak cartridge) to afford the title compound (0.17 g, 76%), LC/MS (APCI, condition 2), m/e 425 (MH$^+$), retention time 3.33 min.

Example 106

Preparation of (2R)-1-piperidin-1-yl-3-(3-thieno[2,3-d]isoxazol-3-yl-phenoxy)-propan-2-ol

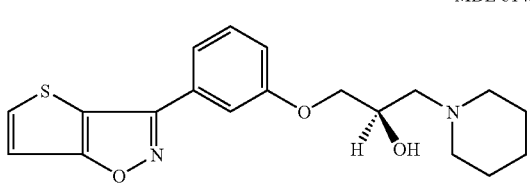

MDL 814316

Prepare as described for example 105 using piperidine (105 mg, 0.0011 mol, Aldrich Chemical Company). After concentration, triturate the crude material with ethyl ether, and collect the solid. Dry the solid in vaco to afford the title compound (0.16 g, 83%), LC/MS (APCI, condition 2), m/e 359 (MH$^+$), retention time 2.12 min.

Examples 107–111

Step J, Scheme II

Examples 107–111 were prepared on the same scale using the techniques of parallel synthesis. Experimental conditions are described in detail for Example 107, with any variations in procedures being noted for Examples 108–111.

Example 107

Preparation of (2R)-1-(3,4-dihydro-1H-isoquinolin-2-yl)-3-[3-(1-methyl-1H-thieno[3,2-c]pyrazol-3-yl)-phenoxy]-propan-2-ol

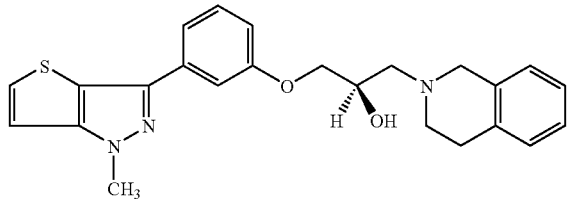

MDL 814911

Add a solution of 1,2,3,4-tetrahydroisoquinoline (Aldrich Chemical Company) in absolute ethanol (0.0465 g, 0.200 M solution, 1.745 mL, 2.0 equiv.) to a reaction tube. Add absolute ethanol (3 mL) to the reaction tube and then add a solution of (R)-1-methyl-3-(3-oxiranylmethoxy-phenyl)-1H-thieno[3,2-c]pyrazole and absolute ethanol (example 8, 0.050 g, 0.200 M solution, 0.875 mL). Shake the reaction mixture under Argon at reflux temperature overnight in a Bohdan apparatus. Cool and concentrate to remove the solvent. Purify the residue by flash chromatography (5 g silica gel SepPak cartridge) eluting in step gradient fashion sequentially with 2% and 5% methanol in dichloromethane, and dichloromethane:methanol:ammonium hydroxide solution, 90:9:1. Combine and concentrate the desired fractions to give the title compound (0.0796 g), LC/MS (APCI, condition 3) m/e 420 (MH$^+$), retention time 5.16 min.

Example 108

Preparation of (2R)-1-[3-(1-methyl-1H-thieno[3,2-c]pyrazol-3-yl)-phenoxy-3-(4-phenyl-piperazin-1-yl)-propan-2-ol

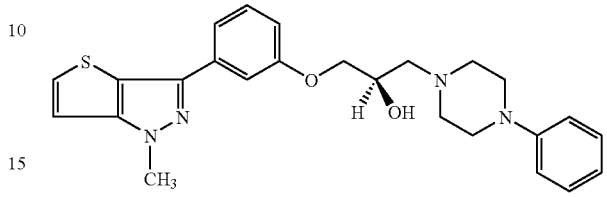

MDL 814913

Prepare as described for example 107 from 1-phenylpiperazine (Aldrich Chemical Company) to give the title compound (0.0643 g), LC/MS (APCI, condition 3) m/e 449 (MH$^+$), retention time 5.22 min.

Example 109

Preparation of (2R)-1-[3-(1-methyl-1H-thieno[3,2-c]pyrazol-3-yl)-phenoxy-3-(4-pyrimidin-2-yl-piperazin-1-yl)-propan-2-ol

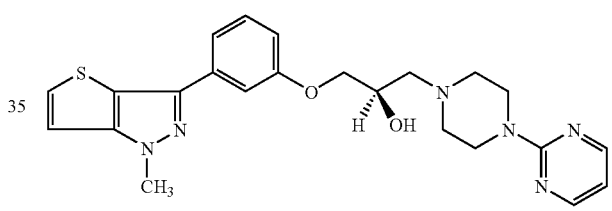

MDL 814914

Prepare as described for example 107 from 1-(2-pyrimidyl)piperazine (Acros) to give the title compound (0.0501 g), LC/MS (APCI, condition 3) m/e 451 (MH$^+$), retention time 5.00 min.

Example 110

Preparation of (4-fluorophenyl)-(1-{2(R)-hydroxy-3-[3-(1-methyl-1H-thieno[3,2-c]pyrazol-3-yl)-phenoxy]-propyl}-piperidin-4-yl)-methanone

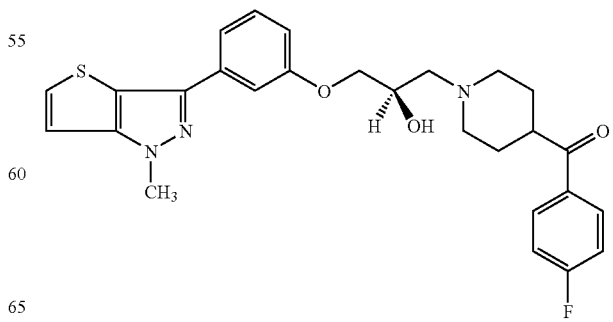

MDL 814915

Prepare as described for example 107 from 4-(4-fluorobenzoyl)piperidine (Maybridge) to give the title compound (0.0633 g), LC/MS (APCI, condition 3) m/e 494 (MH⁺), retention time 5.29 min.

Example 111

Preparation of 1-(1-{2(R)-hydroxy-3-[3-(1-methyl-1H-thieno[3,2-c]pyrazol-3-yl)-phenoxy]-propyl}-piperidin-4-yl)-1,3-dihydrobenzimidazol-2-one

MDL 814916

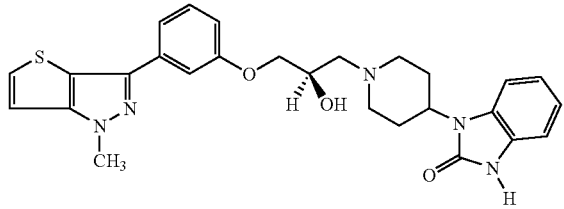

Prepare as described for example 107 from 4-(2-keto-1-benzimidazolinyl)piperidine (Aldrich Chemical Company) to give the title compound (0.1027 g), LC/MS (APCI, condition 3) m/e 504 (MH⁺), retention time 5.08 min.

Example 112

Step N, Scheme III

Preparation of (±)-1-[(N-Benzyl-N-methyl)amino]-3-[3-thieno[2,3-d]isoxazol-3-yl)phenoxy]-2-propanol (compound 1, Scheme III)

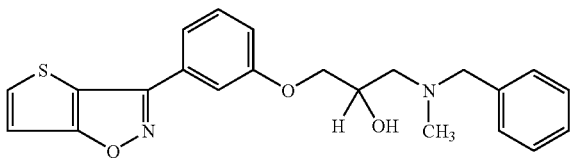

Add potassium t-butoxide (2.83 g, 0.025 mol) in small portions to a stirred solution of 3-thieno[2,3-d]isoxazol-3-yl-phenol (example 1, 5.5 g, 0.025 mol; compound 10, scheme III) and dimethylformamide (50 mL), and then add (γ)—N-methyl-N-(phenylmethyl)oxirane-methanamine (1.5 g, 0.0085 mol, prepare as described in U.S. Pat. No. 3,336,196; compound 18, scheme III). Stir at room temperature for 30 min., warm to 50° C. and stir for two hours. Cool to room temperature, dilute with water (100 mL) and partition between ethyl acetate (500 mL) and water (500 mL). Separate the organic phase and extract the aqueous phase with ethyl acetate (2×300 mL). Combine the organic phases, dry (MgSO₄), filter and concentrate in vacuo. Chromatograph the residue over silica gel, elute with 18:1 dichloromethane:methanol and concentrate the desired fractions to give the title compound.

Example 113

Step L, Scheme II

Preparation of (2R)-(−)-1-benzylamino-2-methyl-3-(3-thieno[2,3-d]isoxazol-3-yl-phenoxy)propan-2-ol

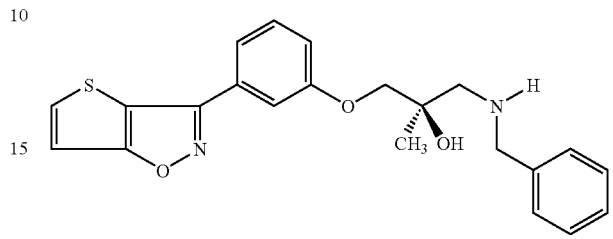

Stir a solution of toluene-4-sulfonic acid (S)-2-hydroxy-2-methyl-3-(3-thieno[2,3-d]isoxazol-3-yl-phenoxy)-propyl ester (intermediate prepared as described in example 6, 2.45 g, 0.00533 g) and tetrahydrofuran (40 mL), and treat dropwise at 0° C. with a solution of benzylamine (0.57 g, 0.00533 mol, Aldrich Chemical Company) and tetrahydrofuran (10 mL). Stir overnight at room temperature, concentrate in vacuo and partition the residue between ethyl acetate (100 mL) and water (100 mL). Separate the organic phase, dry (MgSO₄), filter and concentrate in vacuo. Purify the residue by flash chromatography (silica gel, elute with 9:1 dichloromethane:methanol) to give the free base of the title compound. The maleate salt may be prepared as described for example 66.

Receptor Binding Assay $D_4$ receptor-binding affinities of the compounds were evaluated according to their ability to reduce binding of $^3$H-spiperone as compared to the reference compound clozapine. The potency of the test compound to reduce $^3$H-spiperone binding directly correlated to its binding affinity for the receptor.

$D_4$ Receptor Preparation

HEK 298 (human embryonic kidney) cells stably transfected with human $D_4$ receptor (D4.2 sub-type) were grown in NUNC cell factories for 5 days (75% confluency) without a media change and removed with versene (approximately 19 mg of cells per cell factory tray). The cells were then centrifuged in a Sorval centrifuge for 10 min, 5000 rpm (GS3 rotor) and the pellets quickly frozen in liquid nitrogen and stored at −80° C. until used in binding assay. When used in the assay, cells were thawed on ice for 20 min and then 10 mL of incubation buffer (50 mM Tris, 1 mM EDTA, 4 mM MgCl₂, 5 mM KCl, 1.5 mM CaCl₂, 120 mM NaCl, pH 7.4) was added. The cells were then vortexed to resuspend pellet and homogenized with a Kinematica, CH-6010 Kriens-LU, homogenizer for 15 seconds at setting 7. Concentration of receptor protein was determined using the Pierce BCA assay.

Total Spiperone Binding Assay

The incubation was started by the addition of 100 μl (50 μg protein) membrane homogenate to a solution of 300 μl incubation buffer and 100 μl (0.25 nM final conc.) $^3$H-spiperone (90 Ci/mmol, Amersham, diluted in borosilicate glass vial) in 96-well polypropylene plates (1 mL per well). The plates were vortexed and incubated at room temperature for 90 minutes. The binding reaction was stopped by filtering using a Packard Harvester. The samples were filtered under vacuum over glass fibre filter plates (Whatman GF/B) pre-soaked for 2 hours in 0.3% polyethylenimine (PEI) in 50 mM Tris buffer (pH 7.4). The filters were then washed 6 times with 7 mL ice cold 50 mM Tris buffer (pH 7.4). The filter plates were dried overnight and 35 μl of Microscint-O (Packard) was added. The plates were sealed and counted in the Packard Top Count (3 minutes per well).

Non-specific Binding Assay for $D_4$

The incubation was started by the addition of 100 μl (50 μg protein) membrane homogenate to a solution of 200 μl incubation buffer, 100 μl $^3$H-spiperone (90 Ci/mmol, Amersham, diluted in borosilicate glass vial to 0.25 nM final conc.) and 100 μl (30 μM final conc.) of fresh dopamine (Research Biochemicals Inc., light protected and dissolved in incubation buffer) in 96-well polypropylene plates (1 mL per well). The plates were vortexed and incubated at room temperature for 90 minutes at which time the binding reaction was stopped by filtering. The filters were washed and counted using the same procedure as in the total binding assay described above to give the nonspecific binding value (NSB).

Displacement Binding Assay

The incubation was started by the addition, in 96-well polypropylene plates (1 mL per well), of 100 μl (50 μg protein) membrane homogenate to a solution of 200 μl incubation buffer, 100 μl (0.25 nM final conc.) $^3$H-spiperone (90 Ci/mmol, Amersham, diluted in borosilicate glass vial) and 100 μl of test compound that was prepared from 1 mM stock dissolved in DMSO and stored at −20° C. in polypropylene cryogenic storage vials until dilution in incubation buffer in 96-well polypropylene plates. The plates were vortexed and incubated at room temperature for 90 minutes at which time the binding reaction was stopped by filtering. The filters were washed and counted using the same procedure as in the total binding assay described above to give the displacement binding value ($B_D$).

Calculations

The test compounds were initially assayed at 1 and 0.1 μM and then at a range of concentrations chosen such that the middle dose would cause about 50% inhibition of $^3$H-spiperone binding. Specific binding in the absence of test compound ($B_0$) was the difference of total binding ($B_T$) minus non-specific binding (NSB) and similarly specific binding (in the presence of test compound) (B) was the difference of displacement binding ($B_D$) minus non-specific binding (NSB). $IC_{50}$ was determined from an inhibition response curve, logit-log plot of % $B/B_o$ vs concentration of test compound.

Ki was calculated by the Cheng and Prustoff transformation:

$$Ki=IC_{50}/(1+[L]/K_D)$$

where [L] is the concentration of $^3$H-spiperone used in the assay and $K_D$ is the dissociation constant of $^3$H-spiperone determined independently under the same binding conditions.

MK-801 Stereotypy in Mice

Mk-801 dose-dependently induces characteristic stereotypy marked by locomotion and falling behavior. This MK-801 induced behavior can be antagonized by novel neuroleptic agents. This assay can also assess time course effects following drug administration.

CD-1 or C57 male mice are individually placed in activity boxes (8 mice/drug) and allowed to acclimate for 60 minutes. The mice are then administered test compounds either i.p., s.c., or p.o., at 15, 30, or 60 minutes prior to MK-801 (0.2 mg/kg) administration. Mice are observed for the presence of locomotion and falling behaviors 15 minutes following MK-801. For the duration of action studies the test compounds are administered i.p., s.c., or p.o., at 30, 60, 120, 180, and 240 minutes prior to MK-801 administration. $ED_{50}$ values and 95% confidence limits are calculated by Litchfield and Wilcoxon method.

The following table contains information about the preparation of compounds within the scope of the present invention. The Example Number (column 2) refers to an exact or analogous procedure that may be used to prepare the Compound Number (column 1).

Thienoisoxazolyl- and Thienylpyrrazolyl-Phenoxy Substituted Propyl Derivatives Useful as $D_4$ Antagonists

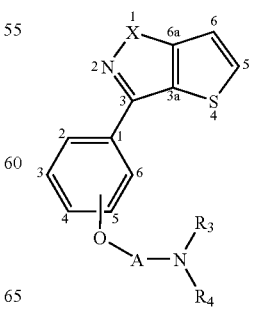

| Table No. | Expl. No. | MDL No. | X | O—A—NR₃R₄ | NR₃R₄ | Position of —O—A— NR₃R₄ | $D_4$ RBA $K_i$ (μM) | $D_4$ RBA % Inhib. @ 1 μM | Antagonism of MK801 Stereotypy % Inhib. @ 20 mg/kg (route) |
|---|---|---|---|---|---|---|---|---|---|
| 1 | 56 | 812531 | O | 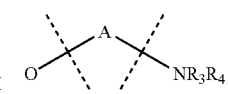 OH |  | 3 | | 58 | |
| 2 | 9 | 812684 | O | 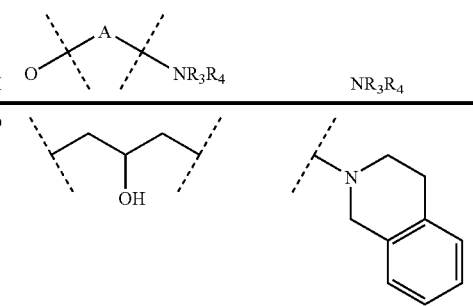 OH R-Configuration | N—CH₃ benzyl | 3 | 0.106 | | |
| 3 | 66 | 812723 | O | H₃C OH S-Configuration | N—H benzyl | 3 | 0.0033 | | 37.5 (ip) |
| 4 | 67 | 812725 | O | HO CH₃ R-Configuration | N—H benzyl | 3 | 0.0377 | | 12.5 (ip) |
| 5 | 27 (maleate) Free base | 812726 (maleate) 813035 (free base) | O | HO CH₃ R-Configuration | N—H thiophene | 3 | 0.0592 (maleate) 0.026 (free base) | | 37.5 (ip) |
| 6 | 57 | 812794 | O | OH R-Configuration | N—H thiophene | 3 | 0.0126 | | 25 (ip) |
| 7 | 58 | 812827 | O | OH R-Configuration | piperazine-4-Cl-phenyl | 3 | 0.0296 | | |
| 8 | 10 | 812828 | O | OH R-Configuration | piperazine-2-OCH₃-phenyl | 3 | 0.0017 | | |
| 9 | 59 | 812829 | O | OH R-Configuration | N—H 3-thienyl | 3 | 0.0076 | | 12 (ip) |

-continued

| Table No. | Expl. No. | MDL No. | X | A (with OH) | NR₃R₄ | Position of —O—A— NR₃R₄ | D₄ RBA K$_i$ (μM) | D₄ RBA % Inhib. @ 1 μM | Antagonism of MK801 Stereotypy % Inhib. @ 20 mg/kg (route) |
|---|---|---|---|---|---|---|---|---|---|
| 10 | 60 | 812858 | O | OH, R-Configuration | N(H)CH₂-naphthyl | 3 | 0.103 | | |
| 11 | 68 | 812883 | O | H₃C, OH, R-Configuration | N(CH₃)CH₂-phenyl | 3 | 0.0098 | | |
| 12 | 28 | 813022 | O | H₃C, OH, R-Configuration | N(H)CH₂-C₆H₄-4-OCH₃ | 3 | 0.039 | | |
| 13 | 29 | 813023 | O | H₃C, OH, R-Configuration | N(H)CH₂-C₆H₄-2-OCH₃ | 3 | 0.025 | | |
| 14 | 30 | 813024 | O | H₃C, OH, R-Configuration | N(H)CH₂-C₆H₄-4-Cl | 3 | 0.071 | | |
| 15 | 31 | 813025 | O | H₃C, OH, R-Configuration | N(H)CH₂-C₆H₄-4-F | 3 | 0.011 | | 50 (sc) |
| 16 | 32 | 813026 | O | H₃C, OH, R-Configuration | N(H)CH₂-C₆H₄-2-F | 3 | 0.031 | | |
| 17 | 33 | 813027 | O | H₃C, OH, R-Configuration | N(H)CH₂-furyl | 3 | 0.045 | | |

-continued

| Table No. | Expl. No. | MDL No. | X | O—A—NR₃R₄ | NR₃R₄ | Position of —O—A— NR₃R₄ | D₄ RBA K$_i$ (μM) | D₄ RBA % Inhib. @ 1 μM | Antagonism of MK801 Stereotypy % Inhib. @ 20 mg/kg (route) |
|---|---|---|---|---|---|---|---|---|---|
| 18 | 34 | 813028 | O | H₃C, OH R-Configuration | –NH–CH₂–C₆H₄–CF₃ (para) | 3 | | 67 | |
| 19 | 35 | 813029 | O | H₃C, OH R-Configuration | –NH–CH(CH₃)–C₆H₅ R-Configuration | 3 | | 69 | |
| 20 | 36 | 813030 | O | H₃C, OH R-Configuration | –NH–CH(CH₃)–C₆H₅ S-Configuration | 3 | 0.134 | | |
| 21 | 37 | 813031 | O | H₃C, OH R-Configuration | –NH–CH₂–(1-naphthyl) | 3 | 0.055 | | |
| 22 | 38 | 813032 | O | H₃C, OH R-Configuration | –NH–CH₂–(4-pyridyl) | 3 | | 56 | |
| 23 | 39 | 813033 | O | H₃C, OH R-Configuration | –NH–CH₂–(3-pyridyl) | 3 | 0.077 | | |
| 24 | 40 | 813034 | O | H₃C, OH R-Configuration | –NH–CH₂–(2-pyridyl) | 3 | 0.079 | | |
| 25 | 41 | 813054 | O | OH R-Configuration | –NH–CH₂–(2-furyl) | 3 | 0.057 | | |

-continued

| Table No. | Expl. No. | MDL No. | X | O—A—NR₃R₄ | NR₃R₄ | Position of —O—A— NR₃R₄ | D₄ RBA $K_i$ (μM) | D₄ RBA % Inhib. @ 1 μM | Antagonism of MK801 Stereotypy % Inhib. @ 20 mg/kg (route) |
|---|---|---|---|---|---|---|---|---|---|
| 26 | 42 | 813055 | O | OH R-Configuration | —NH—CH₂—(3-pyridyl) | 3 | 0.121 | | |
| 27 | 43 | 813056 | O | OH R-Configuration | —NH—CH₂—CH(OH)—Ph | 3 | 0.131 | | 75 (sc) |
| 28 | 44 | 813082 | O | OH R-Configuration | piperazinyl-(2-F-phenyl) | 3 | 0.022 | | |
| 29 | 45 | 813083 | O | OH R-Configuration | piperazinyl-(4-F-phenyl) | 3 | 0.085 | | |
| 30 | 46 | 813084 | O | OH R-Configuration | piperazinyl-(2-Cl-phenyl) | 3 | 0.029 | | |
| 31 | 47 | 813085 | O | OH R-Configuration | piperazinyl-(3-Cl-phenyl) | 3 | 0.069 | | |
| 32 | 48 | 813086 | O | OH R-Configuration | piperazinyl-(4-OCH₃-phenyl) | 3 | 0.057 | | |

-continued
| Table No. | Expl. No. | MDL No. | X | 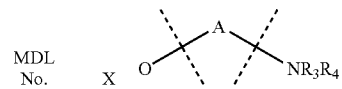 | NR₃R₄ | Position of —O—A— NR₃R₄ | D₄ RBA K$_i$ (μM) | D₄ RBA % Inhib. @ 1 μM | Antagonism of MK801 Stereotypy % Inhib. @ 20 mg/kg (route) |
|---|---|---|---|---|---|---|---|---|---|
| 33 | 49 | 813087 | O | 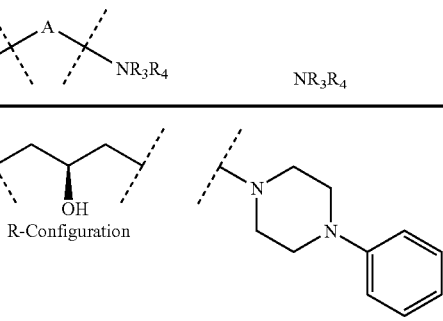<br>R-Configuration | 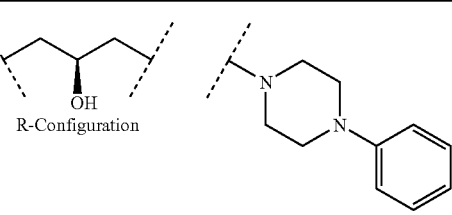 | 3 | 0.020 | | |
| 34 | 50 | 813088 | O | 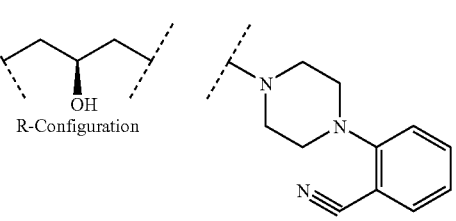<br>R-Configuration | 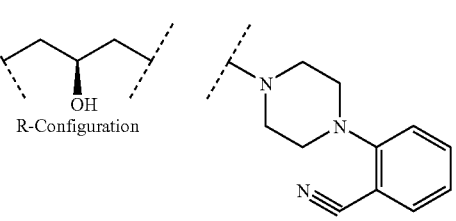 | 3 | 0.003 | | |
| 35 | 51 | 813089 | O | 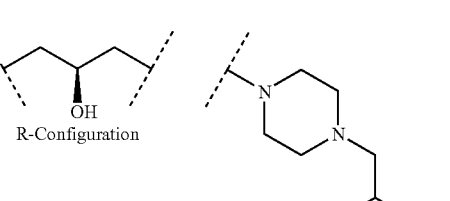<br>R-Configuration | 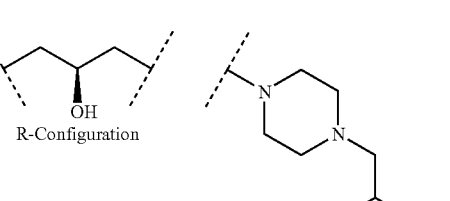 | 3 | | | 57 |
| 36 | 52 | 813090 | O | <br>R-Configuration | 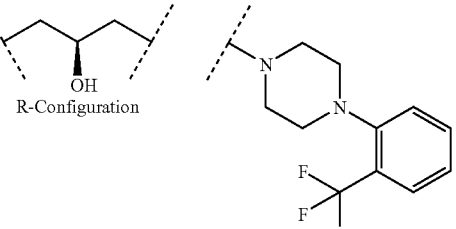 | 3 | 0.084 | | |
| 37 | 53 | 813100 | O | <br>R-Configuration | 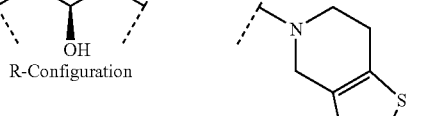 | 3 | 0.067 | | |
| 38 | 54 | 813107 | O | 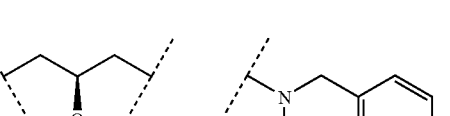<br>R-Configuration | 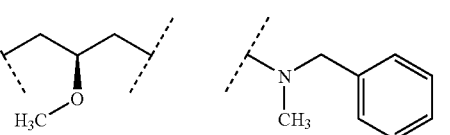 | 3 | 0.177 | | |

-continued

| Table No. | Expl. No. | MDL No. | X | A | NR₃R₄ | Position of —O—A— NR₃R₄ | D₄ RBA K$_i$ (μM) | D₄ RBA % Inhib. @ 1 μM | Antagonism of MK801 Stereotypy % Inhib. @ 20 mg/kg (route) |
|---|---|---|---|---|---|---|---|---|---|
| 39 | 55 | 813108 | O | H₃C—O, R-Configuration | N(H)-benzyl | 3 | 0.026 | | |
| 40 | 23 | 813117 | O | OH, R-Configuration | N(H)-CH₂-naphthyl | 4 | 0.175 | | |
| 41 | 24 | 813127 | O | OH, R-Configuration | N(H)-CH₂-(3-thienyl) | 4 | | 62 | |
| 42 | 25 | 813128 | O | OH, R-Configuration | N(H)-CH₂-(2-furyl) | 4 | | 44 | |
| 43 | 26 | 813129 | O | OH, R-Configuration | N(H)-CH₂-(2-thienyl) | 4 | 0.171 | | |
| 44 | 61 | 813152 | O | OH, R-Configuration | 1,2,3,4-tetrahydroisoquinolin-2-yl | 4 | | 64 | |
| 45 | 62 | 813153 | O | OH, R-Configuration | 4-(2-methoxyphenyl)piperazin-1-yl | 4 | 0.080 | | |
| 46 | 63 | 813154 | O | OH, R-Configuration | 4,5,6,7-tetrahydrothieno[3,2-c]pyridin-5-yl | 4 | | 73 | |

-continued

| Table No. | Expl. No. | MDL No. | X | —O—A—NR₃R₄ | NR₃R₄ | Position of —O—A—NR₃R₄ | D₄ RBA K$_i$ (µM) | D₄ RBA % Inhib. @ 1 µM | Antagonism of MK801 Stereotypy % Inhib. @ 20 mg/kg (route) |
|---|---|---|---|---|---|---|---|---|---|
| 47 | 64 | 813157 | O | OH, R-Configuration | piperazinyl-(2-cyanophenyl) | 4 | 0.055 | | |
| 48 | 65 | 813158 | O | OH, R-Configuration | 4-(6-fluorobenzisoxazol-3-yl)piperidinyl | 4 | | 57 | |
| 49 | 69 (Free base of ex 102) | 813267 | O | H₃C, OH, S-Configuration | NH-CH₂-(4-fluorophenyl) | 3 | | 100 | 37.5 (po) |
| 50 | 70 | 813268 | O | H₃C, OH, S-Configuration | NH-CH₂-(2-fluorophenyl) | 3 | | 98 | 50 (po) |
| 51 | 71 | 813269 | O | H₃C, OH, S-Configuration | NH-CH₂-(3-fluorophenyl) | 3 | | 99 | 37.5 (po) |
| 52 | 72 | 813270 | O | H₃C, OH, S-Configuration | NH-CH₂-(4-chlorophenyl) | 3 | | 98 | 37.5 (po) |
| 53 | 73 | 813271 | O | H₃C, OH, S-Configuration | NH-CH₂-(2-chlorophenyl) | 3 | | 96 | 50 (po) |
| 54 | 74 (Base) HCL salt is ex 103 | 813272 | O | H₃C, OH, S-Configuration | NH-CH₂-(3,4-dichlorophenyl) | 3 | 0.013 | | 62.5 (po) |

-continued

| Table No. | Expl. No. | MDL No. | X | (O-A-NR₃R₄ group) | NR₃R₄ | Position of —O—A— NR₃R₄ | D₄ RBA K$_i$ (μM) | D₄ RBA % Inhib. @ 1 μM | Antagonism of MK801 Stereotypy % Inhib. @ 20 mg/kg (route) |
|---|---|---|---|---|---|---|---|---|---|
| 55 | 75 | 813273 | O | H₃C, OH S-Configuration | —NH—CH(CH₃)—Ph R-Configuration | 3 | | 72 | |
| 56 | 76 | 813274 | O | H₃C, OH S-Configuration | —NH—CH(CH₃)—Ph S-Configuration | 3 | | 93 | |
| 57 | 77 | 813275 | O | H₃C, OH S-Configuration | —NH—CH₂-(1-naphthyl) | 3 | | 96 | |
| 58 | 78 | 813276 | O | H₃C, OH S-Configuration | —NH—CH₂-(4-CH₃-C₆H₄) | 3 | | 100 | 37.5 (po) |
| 59 | 79 | 813277 | O | H₃C, OH S-Configuration | —NH—CH₂-(4-OCH₃-C₆H₄) | 3 | | 96 | 50 (po) |
| 60 | 80 | 813278 | O | H₃C, OH S-Configuration | —NH—CH₂-(2-OCH₃-C₆H₄) | 3 | | 99 | 25 (po) |
| 61 | 81 | 813279 | O | H₃C, OH S-Configuration | —NH—CH₂-(2-furyl) | 3 | | 95 | |
| 62 | 82 | 813280 | O | H₃C, OH S-Configuration | —NH—CH₂-(2-thienyl) | 3 | 0.014 | | |

-continued

| Table No. | Expl. No. | MDL No. | X | A | NR₃R₄ | Position of —O—A— NR₃R₄ | D₄ RBA K$_i$ (μM) | D₄ RBA % Inhib. @ 1 μM | Antagonism of MK801 Stereotypy % Inhib. @ 20 mg/kg (route) |
|---|---|---|---|---|---|---|---|---|---|
| 63 | 83 | 813281 | O | H₃C, OH S-Configuration | thiophen-3-ylmethylamino | 3 | | 98 | 50 (po) |
| 64 | 84 | 813282 | O | H₃C, OH S-Configuration | pyridin-3-ylmethylamino | 3 | | 93 | |
| 65 | 85 | 813283 | O | H₃C, OH S-Configuration | pyridin-2-ylmethylamino | 3 | | 91 | |
| 66 | 86 | 813284 | O | H₃C, OH S-Configuration | N-methyl-N-benzylamino | 3 | 0.090 | | |
| 67 | 87 | 813288 | O | H₃C, OH S-Configuration | 4-(2-methoxyphenyl)piperazin-1-yl | 3 | 0.019 | | |
| 68 | 88 | 813289 | O | H₃C, OH S-Configuration | 4-(2-cyanophenyl)piperazin-1-yl | 3 | 0.029 | | |
| 69 | 89 | 813291 | O | H₃C, OH S-Configuration | 4-(3-chlorophenoxy)piperidin-1-yl | 3 | 0.144 | | |

-continued

| Table No. | Expl. No. | MDL No. | X | O—A—NR₃R₄ | NR₃R₄ | Position of —O—A—NR₃R₄ | D₄ RBA K$_i$ (μM) | D₄ RBA % Inhib. @ 1 μM | Antagonism of MK801 Stereotypy % Inhib. @ 20 mg/kg (route) |
|---|---|---|---|---|---|---|---|---|---|
| 70 | 90 | 813292 | O | H₃C, OH S-Configuration | piperidinyl-6-fluoro-benzisoxazole | 3 | 0.017 | | |
| 71 | 11 | 813301 | O | OH R-Configuration | piperazinyl-6-fluoro-1H-indazole | 3 | 0.006 | | |
| 72 | 12 | 813302 | O | OH R-Configuration | piperazinyl-5-methoxy-1H-indazole | 3 | | 77 | |
| 73 | 13 | 813303 | O | OH R-Configuration | piperidinyl-6-fluoro-benzisoxazole | 3 | 0.004 | | |
| 74 | 14 | 813304 | O | OH R-Configuration | piperidinyl-6-chloro-benzisoxazole | 3 | 0.014 | | |
| 75 | 15 | 813305 | O | OH R-Configuration | azabicyclyl-benzisoxazole | 3 | 0.057 | | |

-continued

| Table No. | Expl. No. | MDL No. | X | —O—A—NR₃R₄ | NR₃R₄ | Position of —O—A— NR₃R₄ | D₄ RBA K$_i$ (μM) | D₄ RBA % Inhib. @ 1 μM | Antagonism of MK801 Stereotypy % Inhib. @ 20 mg/kg (route) |
|---|---|---|---|---|---|---|---|---|---|
| 76 | 16 | 813306 | O | OH R-Configuration | piperazinyl-benzisothiazole | 3 | 0.006 | | |
| 77 | 17 | 813307 | O | OH R-Configuration | 6-F-benzisothiazolyl-piperidine | 3 | 0.002 | | |
| 78 | 18 | 813308 | O | OH R-Configuration | 6-F-benzothiophenyl-piperazine | 3 | 0.030 | | |
| 79 | 19 | 813309 | O | OH R-Configuration | pyrimidinyl-piperazine | 3 | 0.024 | | 62.5 (po) |
| 80 | 20 | 813310 | O | OH R-Configuration | pyridinyl-piperazine | 3 | 0.020 | | |
| 81 | 21 | 813312 | O | OH R-Configuration | benzyl-piperidine | 3 | 0.070 | | |
| 82 | 22 | 813313 | O | OH R-Configuration | pyridinyl-methylamine | 3 | | 54 | |

-continued
| Table No. | Expl. No. | MDL No. | X | O-A-NR₃R₄ | NR₃R₄ | Position of —O—A— NR₃R₄ | D₄ RBA K$_i$ (μM) | D₄ RBA % Inhib. @ 1 μM | Antagonism of MK801 Stereotypy % Inhib. @ 20 mg/kg (route) |
|---|---|---|---|---|---|---|---|---|---|
| 83 | 91 | 813669 | O |  OH -Configuration | 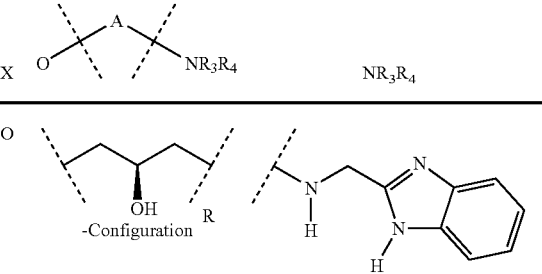 | 3 | | 89 | |
| 84 | 92 | 813670 | O | 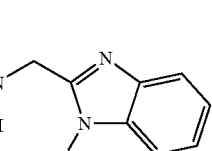 OH R-Configuration | 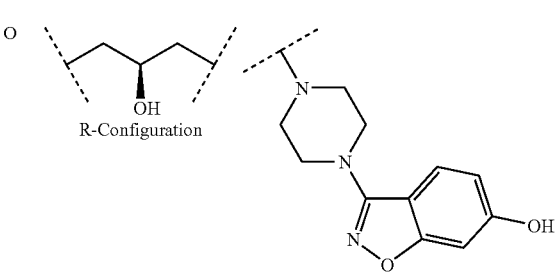 | 3 | | 83 | |
| 85 | 93 | 813674 | O | 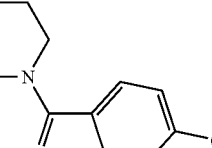 OH R-Configuration | 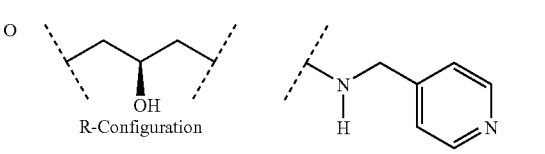 | 3 | | 41 | |
| 86 | 94 | 813675 | O | 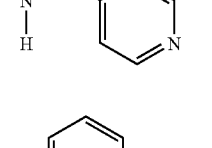 OH R-Configuration | 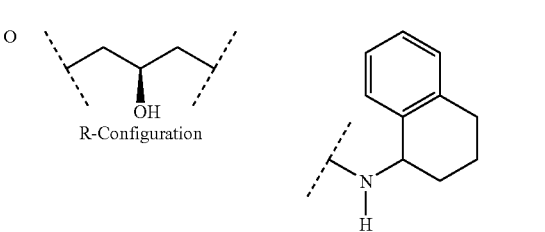 | 3 | | 92 | |
| 87 | 95 | 813676 | O | 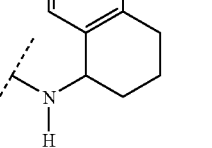 OH R-Configuration | 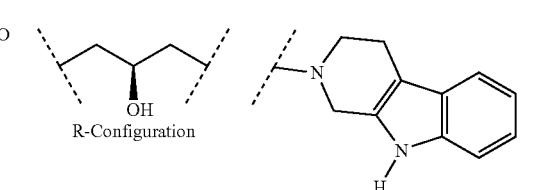 | 3 | | 80 | |
| 88 | 96 | 813677 | O | 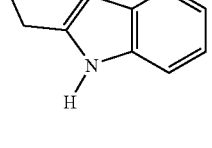 OH R-Configuration | 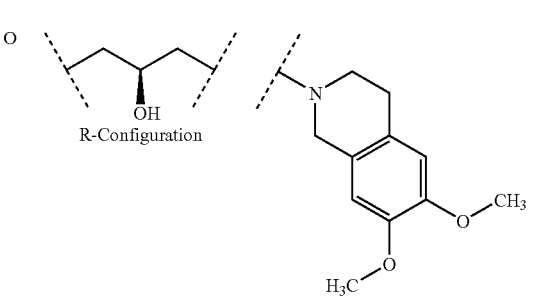 | 3 | | 44 | |

-continued

| Table No. | Expl. No. | MDL No. | X | O—A—NR₃R₄ | NR₃R₄ | Position of —O—A— NR₃R₄ | D₄ RBA K$_i$ (μM) | D₄ RBA % Inhib. @ 1 μM | Antagonism of MK801 Stereotypy % Inhib. @ 20 mg/kg (route) |
|---|---|---|---|---|---|---|---|---|---|
| 89 | 97 | 813678 | O | OH, R-Configuration | piperazine-N-(4-methoxyphenyl)-2-methyl | 3 | | 70 | |
| 90 | 98 | 813679 | O | OH, R-Configuration | 4-(4-chlorophenyl)-4-hydroxypiperidine | 3 | | 59 | |
| 91 | 99 (base) HCl salt | 814157 (base) 814-157A (HCl) | O | OH, R-Configuration | NH-indan-2-yl | 3 | 0.013 (base) 0.017* (HCl) | | |
| 92 | 100 | 814160 | O | OH, R-Configuration | NH-CH₂-cyclohexyl | 3 | | 94 | |
| 93 | 101 | 814161 | O | OH, R-Configuration | NH-indan-1-yl | 3 | 0.016 | | |
| 94 | 102 (HCl) Free base is ex 69 | 814196 | O | H₃C, OH, S-Configuration | NH-CH₂-(4-fluorophenyl) | 3 | 0.0077 | | |
| 95 | 103 (HCl) Free base is ex 74 | 814197 | O | H₃C, OH, S-Configuration | NH-CH₂-(3,4-dichlorophenyl) | 3 | 0.025 | | |
| 96 | 104 | 814198 | O | H₃C, OH, S-Configuration | NH-CH₂-(3,4-difluorophenyl) | 3 | 0.018 | | |

-continued
| Table No. | Expl. No. | MDL No. | X | O—A—NR₃R₄ | NR₃R₄ | Position of —O—A— NR₃R₄ | D₄ RBA K_i (μM) | D₄ RBA % Inhib. @ 1 μM | Antagonism of MK801 Stereotypy % Inhib. @ 20 mg/kg (route) |
|---|---|---|---|---|---|---|---|---|---|
| 97 | 105 | 814310 | O | 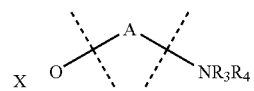 R-Configuration |  | 3 | | 95 | |
| 98 | 106 | 814316 | O | 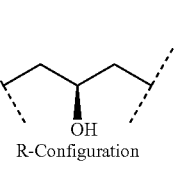 R-Configuration | 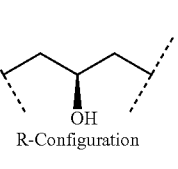 | 3 | | 85 | |
| 99 | 107 | 814911 | N—CH₃ | 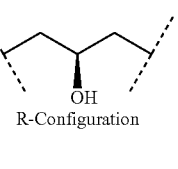 R-Configuration | 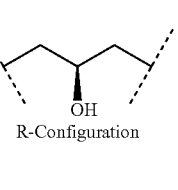 | 3 | | 95 | |
| 100 | 108 | 814913 | N—CH₃ | R-Configuration | | 3 | | 90 | |
| 101 | 109 | 814914 | N—CH₃ | R-Configuration | 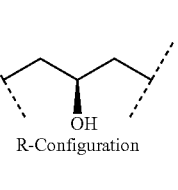 | 3 | | 89 | |
| 102 | 110 | 814915 | N—CH₃ | R-Configuration | 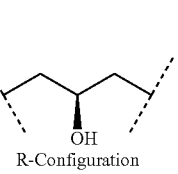 | 3 | | 97 | |

| Table No. | Expl. No. | MDL No. | X | 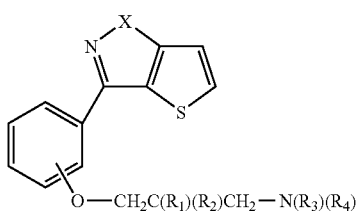 | NR₃R₄ | Position of —O—A— NR₃R₄ | D₄ RBA Kᵢ (μM) | D₄ RBA % Inhib. @ 1 μM | Antagonism of MK801 Stereotypy % Inhib. @ 20 mg/kg (route) |
|---|---|---|---|---|---|---|---|---|---|
| 103 | 111 | 814916 | N—CH₃ | | 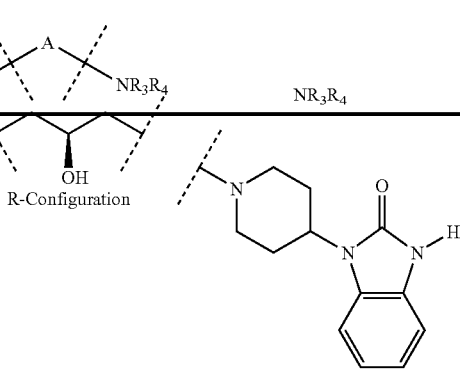 | 3 | | 91 | |

Compounds were tested as either the free base or the salt form corresponding to their synthetic description example number unless otherwise noted in the table.
RBA = receptor binding assay.

What is claimed is:

1. A compound of Formula I:

Formula I $$\text{(structure shown)}$$

a pharmaceutically acceptable salt or stereoisomer thereof, wherein
- X is N(CH₃) or O;
- R₁ is OH or C₁₋₆ alkoxy;
- R₂ is H or C₁₋₆ alkyl;
- R₃ is (CH₂)ₙ Q, CH₂CH(OH)Q, CH(CH₃)Q, 1,2,3,4-tetrahydronaphthyl, indanyl, or adamantyl, wherein
  Q is thienyl or furanyl and
  Q is optionally substituted with one or two moieties independently selected from halo, C₁₋₆ alkyl, C₁₋₆ alkoxy, hydroxy, S(O)H₂NH₂, trifluormethyl, or cyano, and
  n is 1 or 2; and
- R₄ is H or C₁₋₆ alkyl.

2. A compound according to claim 1 wherein Q is thienyl.

3. The compound according to claim 2 which is (2R)-2-methyl-1-(3-thieno[2,3-d]isoxazol-3-yl-phenoxy)-3-[thienophen-2-ylmethyl)-amino-propan-2-ol.

4. The compound according to claim 2 which is (2S)-1-(2-thienylmethylamino)-2-methyl-3-[3-thieno[2,3-d]isoxazol-3-yl-phenoxy]propan-2-ol.

5. The compound according to claim 2 which is (2S)-1-(3-thienylmethylamino)-2-methyl-3-[3-thieno[2,3-d]isoxazol-3-yl-phenoxy]propan-2-ol.

6. A compound according to claim 2 wherein
R₁ is OH;
R₂ is H;
R₃ is (CH₂)ₙ Q; and
n is 1.

7. The compound according to claim 6 wherein Q is thienyl.

8. The compound according to claim 7 which is (2R)-1-(4-thieno[2,3-d]isoxazol-3-yl-phenoxy)-3-[(thiophen-3-yl-methyl)-amino]-propan-2-ol.

9. The compound of claim 7 which is (2R)-1-(4-thieno[2,3-d]isoxazol-3-yl-phenoxy)-3-[(thiophen-2-ylmethyl)-amino]-propan-2-ol.

10. The compound of claim 7 which is (2R)-1-(3-thieno[2,3-d]isoxazol-3-yl-phenoxy)-3-[(thiophen-2-ylmethyl)amino]propan-2-ol.

11. The compound of claim 7 which is (2R)-1-(3-thieno[2,3-d]isoxazol-3-yl-phenoxy)-3-[(thiophen-3-ylmethyl)amino]propan-2-ol.

12. A compound according to claim 1 wherein Q is furanyl.

13. The compound of claim 12 which is (2R)-1-[(furan-2-ylmethyl)-amino]-2-methyl-3-(3-thieno[2,3-d]isoxazol-3-yl-phenoxy)-propan-2-ol.

14. The compound of claim 12 which is (2R)-1-[(furan-2-ylmethyl)amino]-3-(3-thieno[2,3-d]isoxazol-3-yl-phenoxy)-propan-2-ol.

15. The compound of claim 12 which is (2R)-1-[(furan-2-ylmethyl)-amino]-3-(4-thieno[2,3-d]isoxazol-3-yl-phenoxy)propan-2-ol.

16. The compound of claim 12 which is (2S)-1-[(furan-2-ylmethyl)amino]-2-methyl-3-(3-thieno[2,3-d]isoxazol-3-yl-phenoxy)propan-2-ol.

17. A compound according to claim 1 wherein R₃ is indanyl.

18. The compound of claim 17 which is (2R)-1-(indan-1-ylamino)-3-(3-thieno[2,3-d]isoxazol-3-yl-phenoxy)-propan-2-ol.

19. The compound of claim 17 which is (2R)-1-(indan-2-ylamino)-3-(3-thieno[2,3-d]isoxazol-3-yl-phenoxy)-propan-2-ol.

20. A compound according to claim 1, wherein R₃ is adamantyl.

21. The compound of claim 20 which is (2R)-1-(adamantan-1-ylamino)-3-(3-thieno[2,3-d]isoxazol-3-yl-phenoxy)-propan-2-ol.

22. A compound according to claim 1, wherein R₃ is 1,2,3,4-tetrahydronaphthyl.

23. The compound of claim 22 which is (2R)-1-(1,2,3,4-tetrahydronaphthalen-1-ylamino)-3-[3-thieno[2,3-d]isoxazol-3-yl)phenoxy]propan-2-ol.

24. A composition comprising a compound according to claim 1 in admixture with an inert carrier.

25. The composition according to claim 24 wherein said inert carrier is a pharmaceutical carrier.

26. A method of making a compound of formula I

I a pharmaceutically acceptable salt or stereoisomer thereof, wherein
X is $N(CH_3)$ or O;
$R_1$ is OH or $C_{1-6}$ alkoxy;
$R_2$ is H or $C_{1-6}$ alkyl;
$R_3$ is $(CH_2)_n$ Q, $CH_2CH(OH)Q$, $CH(CH_3)Q$, 1,2,3,4-tetrahydronaphthyl, indanyl, or adamantyl, wherein
Q is thienyl or furanyl, and
Q is optionally substituted with one or two moieties independently selected from halo, $C_{1-6}$ alkyl, $C_{1-6}$ alkoxy, hydroxy, $S(O)_2NH_2$, trifluoromethyl, or cyano, and
n is 1 or 2; and
$R_4$ is H or $C_{1-6}$ alkyl;
comprising the step of coupling a reagent of formula II

II wherein X and $R_2$ are as defined in formula I;
with a reagent of formula III

III wherein $R_3$ and $R_4$ are as defined in formula I;
to provide the compound of formula I.

27. A method of making a compound of formula I

I a pharmaceutically acceptable salt or stereoisomer thereof, wherein
X is $N(CH_3)$ or O;
$R_1$ is OH or $C_{1-6}$ alkoxy;
$R_2$ is H or $C_{1-6}$ alkyl;
$R_3$ is $(CH_2)_n$ Q, $CH_2CH(OH)Q$, $CH(CH_3)Q$, 1,2,3,4-tetrahydronaphthyl, indanyl, or adamantyl, wherein
Q is thienyl or furanyl, and
Q is optionally substituted with one or two moieties independently selected from halo, $C_{1-6}$ alkyl, $C_{1-6}$ alkoxy, hydroxy, $S(O)_2NH_2$, trifluoromethyl, or cyano, and
n is 1 or 2; and
$R_4$ is H or $C_{1-6}$ alkyl;
comprising the step of coupling a compound of formula II

II wherein X and $R_2$ are as defined in formula I; and
$R_5$ is $CH_3$, $CF_3$, F, p-bromobenzene, p-nitrobenzene, or p-methylbenzene;
with a reagent of formula m wherein $R_3$ and $R_4$ are as defined in formula I;
to provide the compound of formula I.

28. A method of making a compound of formula I

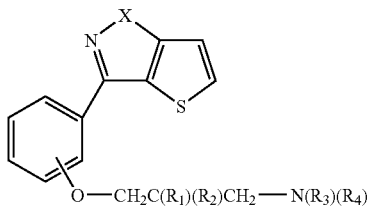

a pharmaceutically acceptable salt or stereoisomer thereof, wherein

X is N(CH$_3$) or O;

R$_1$ is OH or C$_{1-6}$ alkoxy;

R$_2$ is H or C$_{1-6}$ alkyl;

R$_3$ is (CH$_2$)$_n$ Q, CH$_2$CH(OH)Q, CH(CH$_3$)Q, 1,2,3,4-tetrahydronaphthyl, indanyl, or adamantyl, wherein Q is thienyl or furanyl, and Q is optionally substituted with one or two moieties independently selected from halo, C$_{1-6}$ alkyl, C$_{1-6}$ alkoxy, hydroxy, S(O)$_2$NH$_2$, trifluoromethyl, or cyano, and n is 1 or 2; and R$_4$ is H or C$_{1-6}$ alkyl;

comprising the step of coupling a reagent of formula II

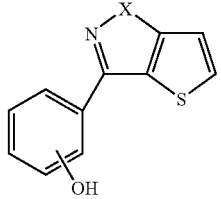

wherein X is as defined in formula I;

with a reagent of formula III

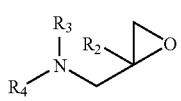

wherein R$_2$, R$_3$, and R$_4$ are as defined in formula I;

to provide the compound of formula I.

* * * * *